United States Patent
Lakowicz et al.

(10) Patent No.: US 9,897,598 B2
(45) Date of Patent: *Feb. 20, 2018

(54) TAMM STRUCTURES FOR ENHANCED FLUORESCENCE BASED SENSING, IMAGING AND ASSAYS

(71) Applicants: Joseph R. Lakowicz, Ellicott City, MD (US); Ramachandram Badugu, Ellicott City, MD (US)

(72) Inventors: Joseph R. Lakowicz, Ellicott City, MD (US); Ramachandram Badugu, Ellicott City, MD (US)

(73) Assignee: THE UNIVERSITY OF MARYLAND, BALTIMORE, Baltimore, MD (US)

( * ) Notice: Subject to any disclaimer, the term of this patent is extended or adjusted under 35 U.S.C. 154(b) by 169 days.

This patent is subject to a terminal disclaimer.

(21) Appl. No.: 14/718,479

(22) Filed: May 21, 2015

(65) Prior Publication Data
US 2015/0338402 A1 Nov. 26, 2015

Related U.S. Application Data

(60) Provisional application No. 62/001,655, filed on May 22, 2014.

(51) Int. Cl.
| G01N 33/551 | (2006.01) |
| G01N 33/543 | (2006.01) |
| G01N 21/64 | (2006.01) |

(52) U.S. Cl.
CPC ..... *G01N 33/54373* (2013.01); *G01N 21/648* (2013.01); *G01N 21/6428* (2013.01); *G01N 21/6456* (2013.01); *G01N 2021/6439* (2013.01)

(58) Field of Classification Search
None
See application file for complete search history.

(56) References Cited

U.S. PATENT DOCUMENTS

2012/0258549 A1* 10/2012 Lu .................. G01N 21/6428
436/501

OTHER PUBLICATIONS

Li, W., et al., "Highly enhanced fluorescence of fluorophores inside a metallic nanocavity," Chemical Communications, Apr. 12, 2011, pp. 5834-5836, vol. 47, No. 20, Publisher: The Royal Society of Chemistry, Published in: http://pubs.rsc.org/en/content/articleland-ing/2011/cc/c1cc11002k#!divAbstract.
(Continued)

*Primary Examiner* — Chris L Chin
(74) *Attorney, Agent, or Firm* — Eugene J. Molinelli; Beusse Wolter Sanks & Maire

(57) ABSTRACT

Techniques for enhanced fluorescence include a Tamm substrate for a target optical frequency comprising a metal nanoscale layer deposited on a Bragg grating. The Bragg grating includes multiple dielectric layers including multiple high index of refraction layers alternating with multiple low index of refraction layers. The dielectric layers are parallel to the metal nanoscale layer; and, the thickness of each dielectric layer is about a fourth of a wavelength of the target optical frequency in the layer. The metal nanoscale layer is configured to host a fluorophore such that an S polarized emission from the fluorophore at the target optical frequency propagates out of the substrate perpendicular to the plurality of dielectric layers.

26 Claims, 24 Drawing Sheets

(56) References Cited

OTHER PUBLICATIONS

Meiss, J., et al., "Highly efficient semitransparent tandem organic solar cells with complementary absorber materials," Applied Physics Letters, Jul. 25, 2011, pp. 0433011-0433013, vol. 99, No. 4, Publisher: American Institute of Physics, Published in: http://scitation.aip.org/content/aip/journal/apl/99/4/10.1063/1.3610551.

Mertens, H. et al., "Plasmon-enhanced luminescence near noble-metal nanospheres: Comparison of exact theory and an improved Gersten and Nitzan model," Physical Review B, Sep. 21, 2007, pp. 1151231-12, vol. 76, No. 11-15, Publisher: American Physical Society, Published in: http://journals.aps.org/prb/abstract/10.1103/PhysRevB.76.115123.

Metzker, M., "Sequencing technologies—the next generation," Nature Reviews Genetics, Dec. 8, 2009, pp. 31-46, vol. 11, Publisher: Macmillan Publishers Limited, Published in: http://www.nature.com/nrg/journal/v11/n1/abs/nrg2626.html.

Nabika, H., et al., "Toward Plasmon-Induced Photoexcitation of Molecules," The Journal of Physical Chemistry Letters, Aug. 2, 2010, pp. 2470-2487, vol. 1, No. 16, Publisher: American Chemical Society, Published in: http://pubs.acs.org/doi/abs/10.1021/jz100914r.

Nikolaev, I., et al., "Fluorescence Lifetime of Emitters with Broad Homogeneous Linewidths Modified in Opal Photonic Crystals," The Journal of Physical Chemistry C, Jan. 28, 2008, pp. 7250-7254, vol. 112, No. 18, Publisher: American Chemical Society, Published in: http://pubs.acs.org/doi/abs/10.1021/jp7111439.

Norton, S., et al., "Plasmonics Quenching and Enhancement of a Fluorescing Molecule Outside and Inside a Silver Metallic Nanoshell," IEEE Transactions on Nanotechnology, 2011, pp. 1264-1274, vol. 10, No. 6, Publisher: IEEE.

Pedersen, M., et al., "Slow-light enhanced optical detection in liquid-infiltrated photonic crystals," Opt. Quant. Electron, Oct. 17, 2007, pp. 903-011, No. 39, Publisher: Springer, Published in: http://arxiv.org/abs/0710.3653v1.

Sasin, M., et al., "Tamm plasmon polaritons: Slow and spatially compact light," Applied Physics Letters, Jun. 26, 2008, pp. 2511121-2511123, vol. 92, No. 25, Publisher: American Institute of Physics, Published in: http://scitation.aip.org/content/aip/journal/apl/92/25/10.1063/1.2952486.

Scalora, M., et al., "Transparent, metallo-dielectric, one-dimensional, photonic band-gap structures," Journal of Applied Physics, Mar. 1, 1998, pp. 2377-2383, vol. 83, No. 5, Publisher: American Institute of Physics, Published in: http://scitation.aip.org/content/aip/journal/jap/83/5/10.1063/1.366996.

Schuller, J., et al., "Plasmonics for extreme light concentration and manipulation," Nature Materials, Feb. 19, 2010, pp. 193-204, vol. 9, Publisher: Macmillan Publishers Limited, Published in: http://www.nature.com/nmat/journal/v9/n3/abs/nmat2630.html.

Shalabney, A., et al., "Surface plasmon resonance from metallic columnar thin films," Photonics and~Nanostructures—Fundamentals and Applications, May 18, 2009, pp. 176-185, vol. 7, No. 4, Publisher: Elsevier B.V., Published in: http://www.sciencedirect.com/science/article/pii/S1569441009000303.

Stockman, M., "Nanoplasmonics: past, present, and glimpse into future," Optics Express, Oct. 24, 2011, pp. 22029-22106, vol. 19, No. 22, Publisher: OSA Publishing, Published in: https://www.osapublishing.org/oe/abstract.cfm?uri=oe-19-22-22029.

Sun, G. et al., "Practical enhancement of photoluminescence by metal nanoparticles," Applied Physics Letters, Mar. 9, 2009, pp. 1011031-1011033, vol. 94, No. 10, Publisher: American Institute of Physics, Published in: http://scitation.aip.org/content/aip/journal/apl/94/10/10.1063/1.3097025.

Sun, G. et al., "Impact of high-order surface plasmon modes of metal nanoparticles on enhancement of optical emission," Applied Physics Letters, Oct. 27, 2009, pp. 1711031-1711033, vol. 95, No. 17, Publisher: American Institute of Physics, Published in: http://scitation.aip.org/content/aip/journal/apl/95/17/10.1063/1.3250160.

Tam, F., et al., "Plasmonic Enhancement of Molecular Fluorescence," Nano Letters, Jan. 27, 2007, pp. 496-501, vol. 7, No. 2, Publisher: American Chemical Society, Published in: http://pubs.acs.org/doi/abs/10.1021/nl062901x.

Thevenaz, L., et al., "Enhancing the light-matter interaction using slow light:towards the concept of dense light," Advances in Slow and Fast Light V, Feb. 9, 2012, pp. 82731-D1-82731-D8, vol. 8273, Publisher: SPIE, Published in: http://proceedings.spiedigitallibrary.org/proceeding.aspx?articleid=1281311.

Tian, M., et al., "Plasmonic Bragg reflectors based on metal-embedded MIM structure," Optics Communications, Aug. 9, 2012, pp. 5122-5127, vol. 285, No. 24, Publisher: Elsevier B.V., Published in: http://www.sciencedirect.com/science/article/pii/S0030401812007675.

Tsang, S., et al., "Observation of Tamm plasmon polaritons in visible regime from ZnO/Al2O3 distributed Bragg reflector Ag interface," Optics Communications, Dec. 22, 2010, pp. 1890-1892, vol. 284, No. 7, Publisher: Elsevier B.V., Published in: http://www.sciencedirect.com/science/article/pii/S0030401810013416.

Vukovic, S. M., "Plasmonic Bragg Reflector and Tamm Plasmon Polaritons in Metal-Dielectric Superlattices," ACTA PHYSICA POLONICA A, Proceedings of the International School and Conference on Photonics, PHOTONICA09, pp. 678-680, vol. 116, No. 4, Published in: http://przyrbwn.icm.edu.pl/APP/PDF/116/a116z470.pdf.

Wang, H., et al., "Photonic Crystal Structures with Tunable Structure Color as Colorimetric Sensors," Sensors, Mar. 28, 2013, pp. 4192-4213, vol. 13, No. 4, Publisher: MDPI, Published in: http://www.mdpi.com/1424-8220/13/4/4192/htm.

Wenger, J., et al., "Nanoaperture-Enhanced Signal-to-Noise Ratio in Fluorescence Correlation Spectroscopy," Analytical Chemistry, Dec. 18, 2008, pp. 834-839, vol. 81, No. 2, Publisher: ACS Publications, Published in: http://pubs.acs.org/doi/full/10.1021/ac8024015.

Xie, F, et al., "A method to assess modifications of fluorophore radiative rate by plasmonic structures," Chemical Physics Letters, Nov. 1, 2008, pp. 186-188, vol. 466, No. 4-6, Publisher: Elsevier B.V., Published in: http://www.sciencedirect.com/science/article/pii/S0009261408014358.

Yablonovitch, E., "Inhibited Spontaneous Emission in Solid-State Physics and Electronics," Physical Review Letters, May 18, 1987, pp. 2059-2062, vol. 58, No. 20, Publisher: The American Physical Society, Published n: http://journals.aps.org/prl/abstract/10.1103/PhysRevLett.58.2059.

Yu, F., et al., "Simultaneous Excitation of Propagating and Localized Surface Plasmon Resonance in Nanoporous Gold Membranes," Analytical Chemistry, Sep. 15, 2006, pp. 7346-7350, vol. 78, No. 20, Publisher: American Chemical Society, Published in: http://pubs.acs.org/doi/abs/10.1021/ac060829h.

Zhang, J., et al., "Dye-Labeled Silver Nanoshell-Bright Particle," The Journal of Physical Chemistry B, May 11, 2006, pp. 8986-8991, vol. 110, No. 18, Publisher: American Chemical Society, Published in: http://pubs.acs.org/doi/abs/10.1021/jp057032z.

Zhang, J., et al., "Single-Molecule Studies on Fluorescently Labeled Silver," J Phys Chem C Nanomater Interfaces, Dec. 11, 2007, pp. 18-26, vol. 112, No. 1, Publisher: American Chemical Society, Published in: http://pubs.acs.org/doi/abs/10.1021/jp074938r.

Zhang, Z., "Generalized Fabrication of Nanoporous Metals (Au, Pd, Pt, Ag, and Cu) through Chemical Dealloying," The Journal of Physical Chemistry C, Jun. 24, 2009, pp. 12629-12636, vol. 113, No. 29, Publisher: American Chemical Society, Published in: http://pubs.acs.org/doi/abs/10.1021/jp811445a.

Zhang, J., et al., "Target molecule imaging on tissue specimens by fluorescent metal nanoprobes," Journal of Biomedical Optics, Oct. 26, 2011, pp. 1160041-1160046, vol. 16, No. 11, Publisher: SPIE, Published in: http:// biomedicaloptics.spiedigitallibrary.org/article.aspx?articleid=1167101.

Zhang, J., et al., "Bimetallic Nanoshells for Metal-Enhanced Fluorescence with Broad Band Fluorophores," The Journal of Physical Chemistry C, Oct. 25, 2012, pp. 24224-24232, vol. 116, No. 45, Publisher: ACS Publications, Published in: http://pubs.acs.org/doi/abs/10.1021/jp3057527.

(56) References Cited

OTHER PUBLICATIONS

Zhou, L., et al. "Enhanced optical transmission through metal-dielectric multilayer gratings," Applied Physics Letters, Jul. 8, 2010, pp. 0119051-0119053, vol. 97, No. 1, Publisher: American Institute of Physics, Published in: http://scitation.aip.org/content/aip/journal/apl/97/1/10.1063/1.3458702.

Zhou, H., et al., "Multiple optical Tamm states at a metal-dielectric mirror interface," Optics Letters, Dec. 15, 2010, pp. 4112-4114, vol. 35, No. 24, Publisher: Optical Society of America, Published in: https://www.osapublishing.org/ol/abstract.cfm?uri=ol-35-24-4112.

Abdulhalim, I., et al., "Porosity Effect on Surface Plasmon Resonance from Metallic Sculptured Thin Films," Jun. 18, 2008, pp. 1-5, Conference vol. 7041, Publisher: SPIE, Published in: http://arxiv.org/abs/0806.3035v1.

Akbay, N., et al., "Distance-Dependent Metal-Enhanced Intrinsic Fluorescence of Proteins Using Polyelectrolyte Layer-by-Layer Assembly and Aluminum Nanoparticles," The Journal of Physical Chemistry, Apr. 23, 2013, pp. 10766-10773, vol. 116, Publisher: ACS Publications, Published in: http://pubs.acs.org/doi/abs/10.1021/jp2122714.

Anger, P., et al., "Enhancement and Quenching of Single-Molecule Fluorescence," Physical Review Letters, Mar. 24, 2006, pp. 1130021-1130024, vol. 96, No. 11, Publisher: The American Physical Society, Published in: https://www.researchgate.net/publication/7173795_Enhancement_and_Quenching_of_Single-Molecule_Fluorescence.

Aouani, H., et al., "Bright Unidirectional Fluorescence Emission of Molecules in a Nanoaperture with Plasmonic Corrugations," Nano Letters, Jan. 19, 2011, pp. 637-644, vol. 11, Publisher: ACS Publications, Published in: http://pubs.acs.org/doi/abs/10.1021/nl103738d.

Badugu, R., et al., "Radiative decay engineering 6: Fluorescence on one-dimensional photonic crystals," Analytical Biochemistry, Nov. 1, 2013, pp. 83-96, vol. 442, Publisher: Elsevier Inc., Published in: http://www.sciencedirect.com/science/article/pii/S0003269713003394.

Badugu, R., et al., "Radiative decay engineering 7: Tamm state-coupled emission using a hybrid plasmonic-photonic structure," Analytical Biochemistry, Jan. 15, 2014, pp. 1-13, vol. 445, Publisher: Elsevier Inc., Published in: http://www.sciencedirect.com/science/article/pii/S0003269713004879.

Ballarini, M., et al., "Bloch surface waves-controlled emission of organic dyes grafted on a one-dimensional photonic crystal," Applied Physics Letters, Jul. 27, 2011, pp. 0433021-0433023, vol. 99, No. 4, Publisher: American Institute of Physics, Published in: http://scitation.aip.org/content/aip/journal/apl/99/4/10.1063/1.3616144.

Battal, E., et al., "Metal-dielectric-metal plasmonic resonators for active beam steering in the infrared," Optics Letters, Mar. 14, 2013, pp. 983-985, vol. 38, No. 6, Published in: https://www.osapublishing.org/ol/abstract.cfm?uri=ol-38-6-983.

Brand, S. et al., "Optical Tamm states above the bulk plasma frequency at a Bragg stack/metal interface," Physical Review B, Feb. 17, 2009, pp. 0854161-0854164, vol. 79, No. 8, Publisher: The American Physical Society, Published in: http://journals.aps.org/prb/abstract/10.1103/PhysRevB.79.085416.

Chang, Y., et al., "Enhancement of photoluminescence of different quantum dots by Ag@SiO2 core-shell nanoparticles," Materials Research Bulletin, Feb. 27, 2013, pp. 2076-2078, vol. 48, No. 6, Publisher: Elsevier Ltd., Published in: http://www.sciencedirect.com/science/article/pii/S0025540813001177.

Chen, Y., et al., "Dependence of Fluorescence Intensity on the Spectral Overlap between Fluorophores and Plasmon Resonant Single Silver Nanoparticles," Nano Letters, Feb. 2, 2007, pp. 690-696, vol. 7, No. 3, Publisher: American Chemical Society, Published in: http://pubs.acs.org/doi/abs/10.1021/nl062795z.

Chen, Z., et al., "Study of optical Tamm states based on the phase properties of one-dimensional photonic crystals," Optics Express, Sep. 5, 2012, pp. 21618-21626, vol. 20, No. 19, Publisher: Optical Society of America, Published in: https://www.osapublishing.org/oe/abstract.cfm?uri=oe-20-19-21618.

Choudhury, S., et al., "Steering Fluorescence Emission with Metal-Dielectric-Metal Structures of Au, Ag and Al," J Phys Chem C Nanometer Interfaces, 2013, pp. 15798-15807, vol. 117, No. 30, Publisher: ACS Publications, Published in: http://pubs.acs.org/doi/abs/10.1021/jp4051066.

Choudhury, S., et al., "Tuning Fluorescence Direction with Plasmonic Metal-Dielectric-Metal Substrates," The Journal of Physical Chemistry Letters, 2013, pp. 227-232, vol. 4, No. 1, Publisher: ACS Publications, Published in: http://pubs.acs.org/doi/abs/10.1021/jz301867b.

Chowdhury, M., et al., "Systematic Computational Study of the Effect of Silver Nanoparticle Dimers on the Coupled Emission from Nearby Fluorophores," The Journal of Physical Chemistry, Jul. 9, 2008, pp. 11236-11249, vol. 112, No. 30, Publisher: American Chemical Society, Published in: http://pubs.acs.org/doi/abs/10.1021/jp802414k.

D'Agostino, S., et al., "Dipole-excited surface plasmons in metallic nanoparticles: Engineering decay dynamics within the discrete-dipole approximation," Physical Review B, May 15, 2013, pp. 2054131-20541313, vol. 87, No. 20, Publisher: American Physical Society, Published in: http:journals.aps.org/prb/abstract/10.1103/PhysRevB.87.205413.

Demchenko, A., "Nanoparticles and nanocomposites for fluorescence sensing and imaging," Methods Appl. Fluoresc., May 1, 2013, pp. 1-28, vol. 1, No. 2, Publisher: IOP Publishing Ltd., Published in: stacks.iop.org/MAF/1/022001.

Ding, Y., et al., "Nanoporous Metals with Controlled Multimodal Pore Size Distribution," Journal of the American Chemical Society, Mar. 5, 2003, pp. 7772-7773, vol. 125, No. 26, Publisher: American Chemical Society, Published in: http://pubs.acs.org/doi/abs/10.1021/ja035318g.

Dionne, J., et al., "Plasmonics: Metal-worthy methods and materials in nanophotonics," MRSBulletin, Aug. 1, 2012, pp. 717-724, vol. 37, No. 08, Publisher: Materials Research Society, Published in: http://journals.cambridge.org/action/displayAbstract?fromPage=online&aid=8669483&fileId=S0883769412001716.

Du, G., et al., "Tamm plasmon polaritons in composite structures composed of the metal film and truncated photonic crystals," Applied Physics A, Oct. 25, 2012, pp. 907-911, vol. 109, No. 4, Publisher: Springer-Verlag, Published in: http://link.springer.com/article/10.1007/s00339-012-7358-8.

Eid, J., et al., "Real-Time DNA Sequencing from Single Polymerase Molecules," Science, Jan. 2, 2009, pp. 133-138, vol. 323, No. 5910, Publisher: Science AAS, Published in: http://science.sciencemag.org/content/323/5910/133.short.

Erlebacher, J., et al., Evolution of nanoporosity in dealloying, Nature, Mar. 22, 2001, pp. 450-453, vol. 410, Publisher: Macmillan Magazines Ltd., Published in: http://www.nature.com/nature/journal/v410/n6827/abs/410450a0.html.

Fang, Y., et al., "Tamm states of one-dimensional metal-dielectric photonic crystal," IET Optoelectronics, Feb. 1, 2013, pp. 9-13, vol. 7, No. 1, Publisher: The Institution of Engineering and Technology, Published in: http://eeexplore.ieee.org/xpl/login.jsp?tp=&arnumber=6490092&url=http%3A%2F%2Fieeexplore.ieee.org%2Fxpls%2Fabs_all.jsp%3Farnumber%3D6490092.

Feng, S., et al., "Transparent photonic band in metallodielectric nanostructures," Phys. Rev. B, Aug. 15, 2005, pp. 1-25, vol. 72, No. 8, Publisher: Phys. Rev. B, Published in: http://arxiv.org/abs/physics/0507155v1.

Fort, E., et al., "Surface enhanced fluorescence," Journal of Physics D: Applied Physics, Dec. 17, 2007, pp. 1-31, vol. 41, No. 013001, Publisher: IOP Publishing Ltd., Published in: http://iopscience.iop.org/article/10.1088/0022-3727/41/1/013001/meta;jsessionid=C9C29FEDC76077BFEA65E44A1CCA729B.c2.iopscience.cld.iop.org.

Fu, Y., et al., "Large enhancement of single molecule fluorescence by coupling to hollow silver nanoshells," Chem Commun (Camb.), Oct. 9, 2012, pp. 9726-9728, vol. 48, No. 78, Publisher: The Royal Society of Chemistry, Published in: http://pubs.rsc.org/en/content/articlelanding/2012/cc/c2cc34025a#!divAbstract.

(56) References Cited

OTHER PUBLICATIONS

Fu, Y., et al., "Modification of single molecule fluorescence near metallic nanostructures," Laser & Photonics Reviews, Oct. 27, 2008, pp. 221-232, vol. 3, No. 1-2, Publisher: Wiley, Published in: http://onlinelibrary.wiley.com/doi/10.1002/lpor.200810035/abstract.

Gaspar-Armenta, J., et al., "Photonic surface-wave excitation: photonic crystal-metal interface," Journal of the Optical Society of America B, Nov. 1, 2013, pp. 2349-2354, vol. 20, No. 11, Publisher: Optical Society of America, Published in: https://www.osapublishing.org/josab/abstract.cfm?uri=josab-20-11-2349.

Genet, C. et al., "Light in tiny holes," Nature, Jan. 4, 2007, pp. 39-46, vol. 445, Publisher: Nature Publishing Group, Published in: http://www.nature.com/nature/journal/v445/n7123/abs/nature05350.html.

Gryczynski, I., et al., "Effects of Sample Thickness on the Optical Properties of Surface Plasmon-Coupled Emission," the Journal of Physical Chemistry B, Jul. 16, 2004, pp. 12073-12083, vol. 108, No. 32, Publisher: American Chemical Society, Published in: http://pubs.acs.org/doi/abs/10.1021/jp0312619.

Iorsh, I., Al., "Spontaneous emission enhancement in metal-dielectric metamaterials," Physics Letters A, Jan. 2, 2012, pp. 185-187, vol. 376, No. 3, Publisher: Elsevier B.V., Published in: http://www.sciencedirect.com/science/article/pii/S0375960111013053.

Jain, P., et al., "Plasmonic coupling in noble metal nanostructures," Chemical Physics Letters, Mar. 5, 2010, pp. 153-164, vol. 487, No. 4-6, Publisher: Elsevier B.V., Published in: http://www.sciencedirect.com/science/article/pii/S0009261410001193.

Jang, M., et al., "Plasmonic Rainbow Trapping Structures for Light Localization and Spectrum Splitting," Physical Review Letters, Nov. 11, 2011, pp. 207401-207405, vol. 107, No. 20, Publisher: American Physical Society, Published in: http://journals.aps.org/prl/abstract/10.1103/PhysRevLett.107.207401.

John, S., "Strong Localization of Photons in Certain Disordered Dielectric Superlattices," Physical Review Letters, Jun. 8, 1987, pp. 2486-2489, vol. 58, No. 23, Publisher: APS Physics, Published in: http://journals.aps.org/prl/abstract/10.1103/PhysRevLett.58.2486.

Johnson, P. B. et al., "Optical Constants of the Noble Metals," Physical Review B, 1972, pp. 4370-4379, vol. 6, No. 12, Publisher: The American Physical Society, Published in: http://journals.aps.org/prb/abstract/10.1103/PhysRevB.6.4370.

Jun, Y.C. et al., "Nonresonant enhancement of spontaneous emission in metal-dielectric-metal plasmon wave guide structures," Physical Review B, Oct. 28, 2008, pp. 153111-153114, vol. 78, No. 15, Publisher: The American Physical Society, Published in: http://journals.aps.org/prb/abstract/10.1103/PhysRevB.78.153111.

Jun, Y., et al., "Plasmonic beaming and active control over fluorescent emission," Nature Communications, Apr. 19, 2011, pp. 1-6, vol. 2, Article No. 283, Publisher: Macmillan Publishers Limited, Published in: http://www.nature.com/ncomms/journal/v2/n4/abs/ncomms1286.html.

Kaliteevski, M., et al., "Tamm plasmon-polaritons: Possible electromagnetic states at the interface of a metal and a dielectric Bragg mirror," Physical Review B, Oct. 15, 2007, pp. 1654151-1654155, vol. 76, No. 16, Publisher: The American Physical Society, Published in: http://journals.aps.org/prb/abstract/10.1103/PhysRevB.76.165415.

Kavokin, A., et al., "Optical Tamm states for the fabrication of polariton lasers," Applied Physics Letters, Dec. 20, 2005, pp. 2611051-2611053, vol. 87, Publisher: American Institute of Physics, Published in: http://scitation.aip.org/content/aip/journal/apl/87/26/10.1063/1.2136414.

Kavokin, A., et al., "Lossless interface modes at the boundary between two periodic dielectric structures," Physical Review B, Dec. 5, 2005, pp. 2231021-2231024, vol. 72, No. 23-15, Publisher: The American Physical Society, Published in: http://journals.aps.org/prb/abstract/10.1103/PhysRevB.72.233102.

King, N., et al., "Angle- and Spectral-Dependent Light Scattering from Plasmonic Nanocups," ACS NANO, Jul. 15, 2011, pp. 7254-7262, vol. 5, No. 9, Publisher: American Chemical Society, Published in: http://pubs.acs.org/doi/abs/10.1021/nn202086u.

Kinkhabwala, A., et al., "Large single-molecule fluorescence enhancements produced by a bowtie nanoantenna," Nature Photonics, Oct. 18, 2009, pp. 654-657, vol. 3, Publisher: Nature Publishing Group, Published in: http://www.nature.com/nphoton/journal/v3/n11/full/nphoton.2009.187.html.

Kroekenstoel, E., et al., "Enhanced spontaneous emission rate in annular plasmonic nanocavities," Applied Physics Letters, Dec. 31, 2009, pp. 2631061-2631063, vol. 95, No. 26, Publisher: American Institute of Physics, Published in: http://scitation.aip.org/content/aip/journal/apl/95/26/10.1063/1.3276566.

Kubo, S., et al., "Anisotropic Accelerated Emission of the Chromophores in Photonic Crystals Consisting of a Polystyrene Opal Structure," The Journal of Physical Chemistry C, Jun. 4, 2009, pp. 11704-11711, vol. 113, No. 27, Publisher: American Chemical Society, Published in: http://pubs.acs.org/doi/abs/10.1021/jp901743r.

Kurt, P., et al., "Structural color via layer-by-layer deposition: layered nanoparticle arrays with near-UV and visible reflectivity bands," Journal of Materials Chemistry, Oct. 15, 2009, pp. 8920-8927, vol. 19, No. 47, Publisher: The Royal Society of Chemistry, Published in: http://pubs.rsc.org/en/content/articlelanding/2009/jm/b912211g#!divAbstract.

Lakowicz, J., et al., "Radiative Decay Engineering: Biophysical and Biomedical Applications," Analytical Biochemistry, Oct. 5, 2001, pp. 1-24, vol. 298, No. 1, Publisher: Academic Press, Published in: http://www.sciencedirect.com/science/article/pii/S0003269701953771.

Lakowicz, J., et al., "Radioactive Decay Engineering 2. Effects of Silver Island Films on Fluorescence Intensity, Lifetimes, and Resonance Energy Transfer," Analytical Biochemistry, Feb. 15, 2002, pp. 261-277, vol. 301, No. 2, Publisher: Elsevier Science (USA), Published in: http://www.sciencedirect.com/science/article/pii/S0003269701955034.

Lakowicz, J., "Radiative decay engineering 3. Surface plasmon-coupled directional emission," Analytical Biochemistry, Jan. 15, 2004, pp. 153-169, vol. 324, No. 2, Publisher: Elsevier Inc., Published in: http://www.sciencedirect.com/science/article/pii/S000326970300647X.

Lakowicz, J., "Radiative decay engineering 5: metal-enhanced fluorescence and plasmon emission," Analytical Biochemistry, Feb. 15, 2005, pp. 171-194, vol. 337, No. 2, Publisher: Elsevier, Published in: http://www.sciencedirect.com/science/article/pii/S0003269704009303.

Lakowicz, J., "Plasmonics in Biology and Plasmon-Controlled Fluorescence," Plasmonics, Mar. 1, 2006, pp. 5-33, vol. 1, No. 1, Publisher: Springer Science+Business Media, Inc., Published in: http://link.springer.com/article/10.1007/s11468-005-9002-3.

\* cited by examiner

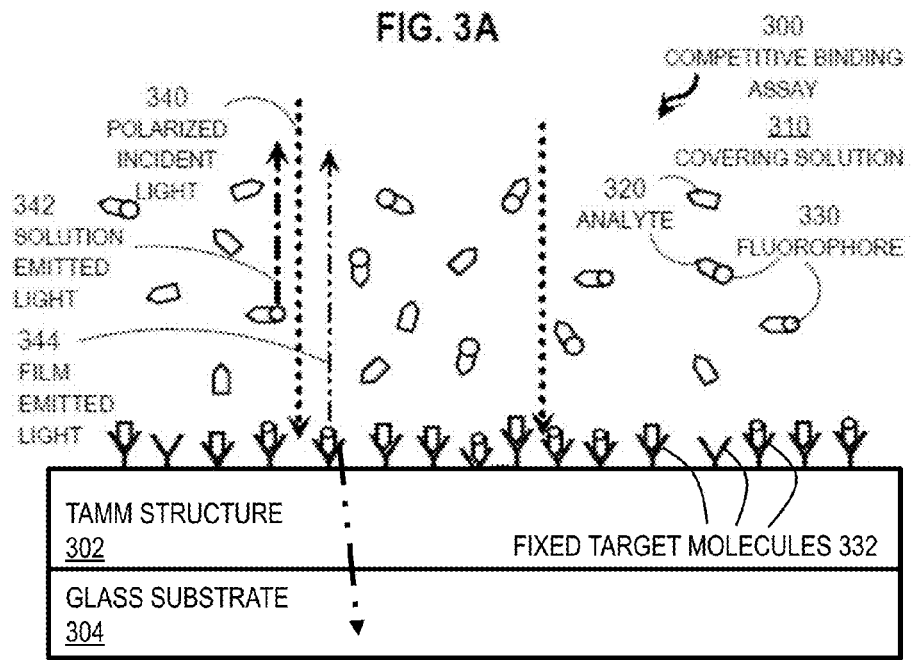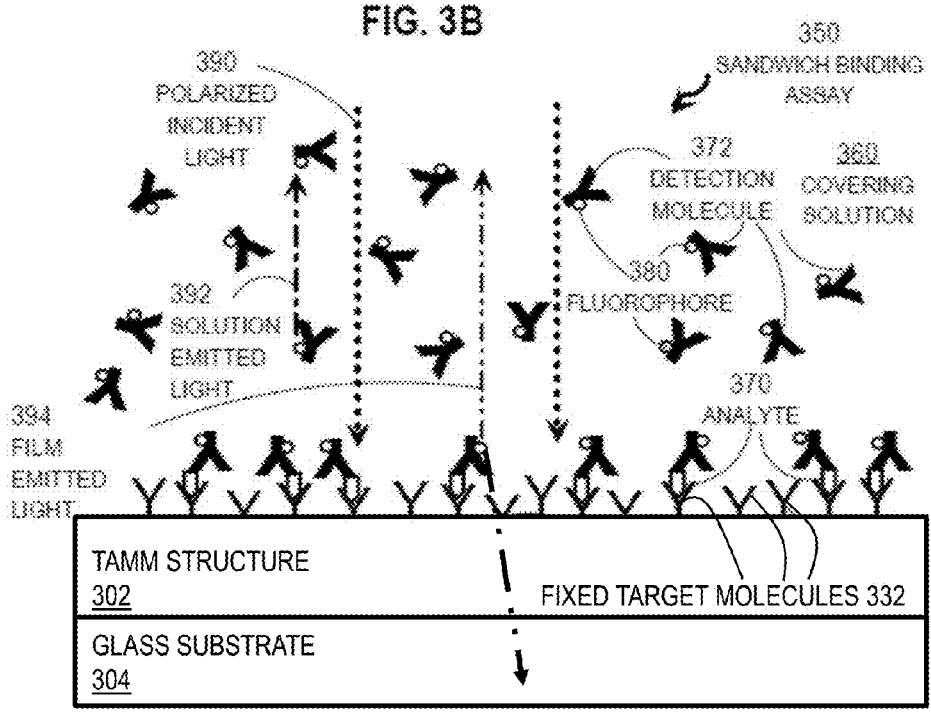

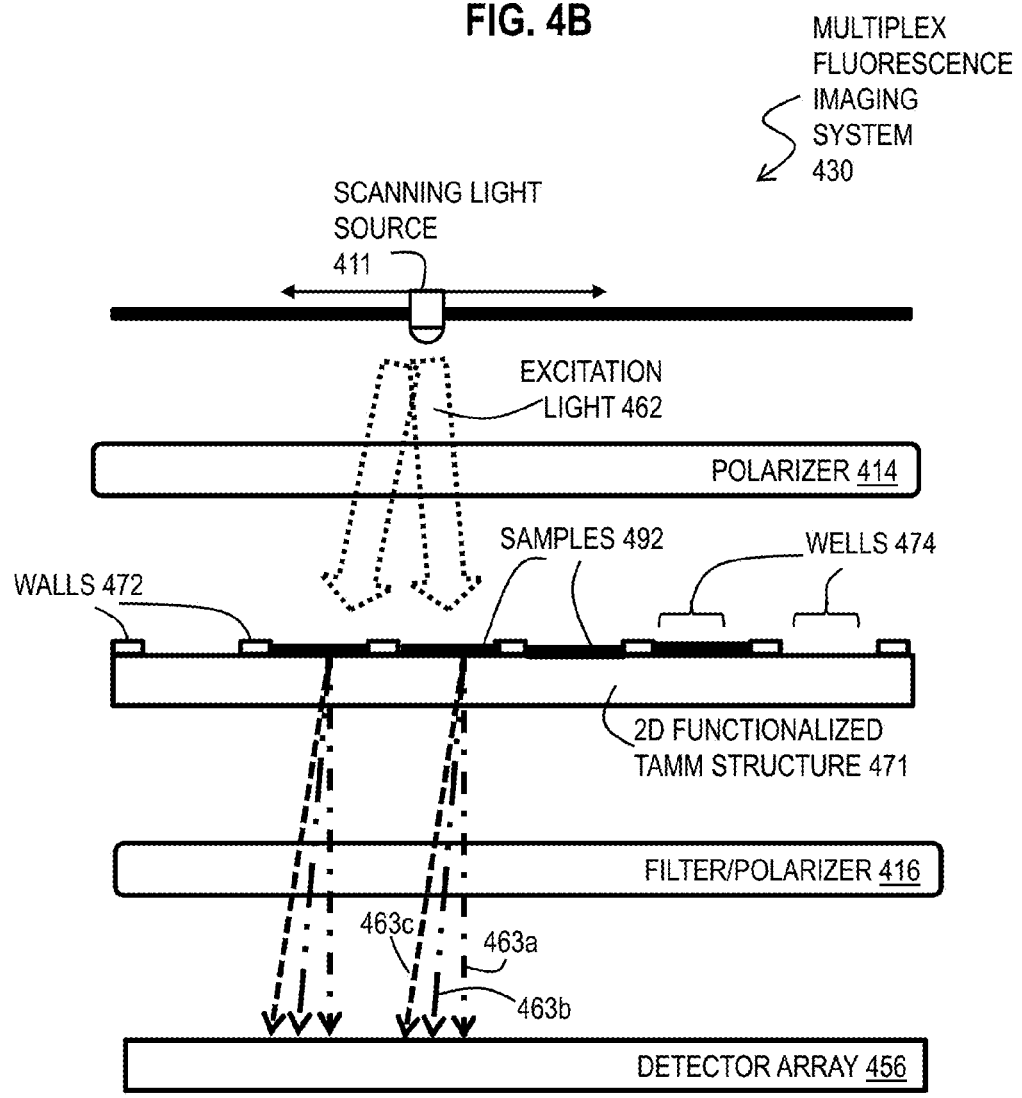

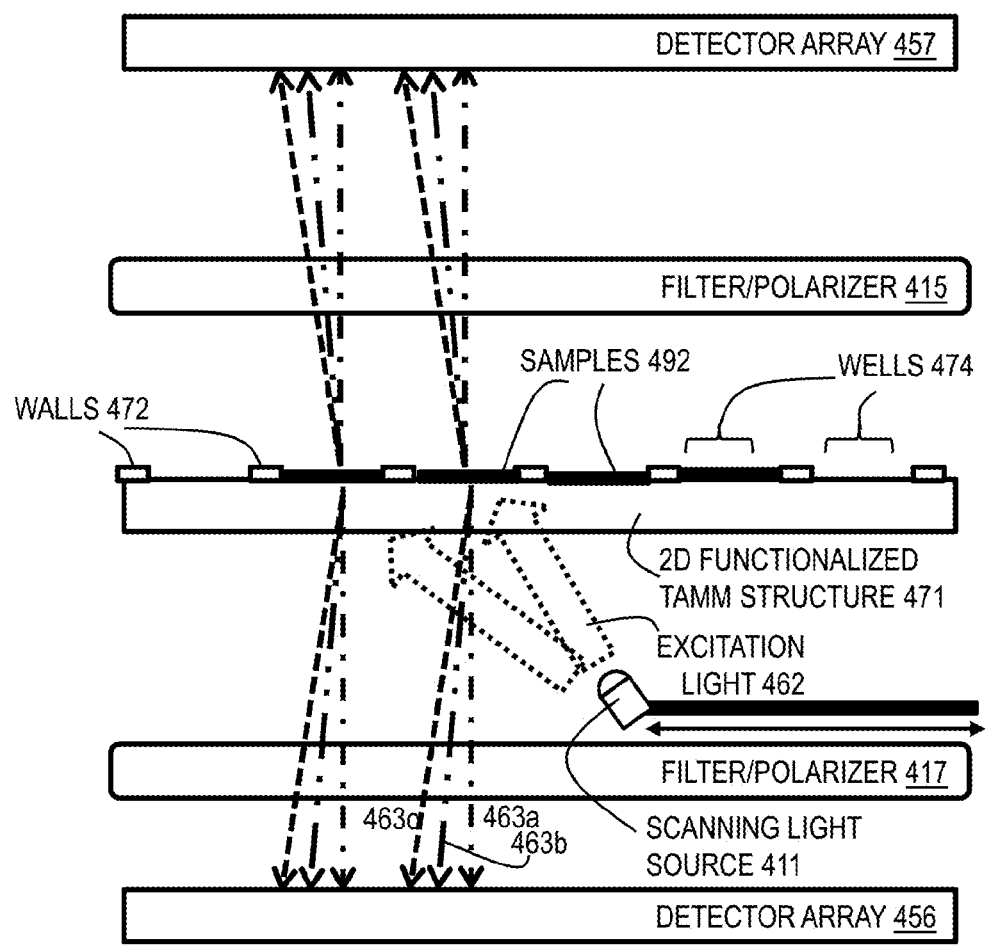

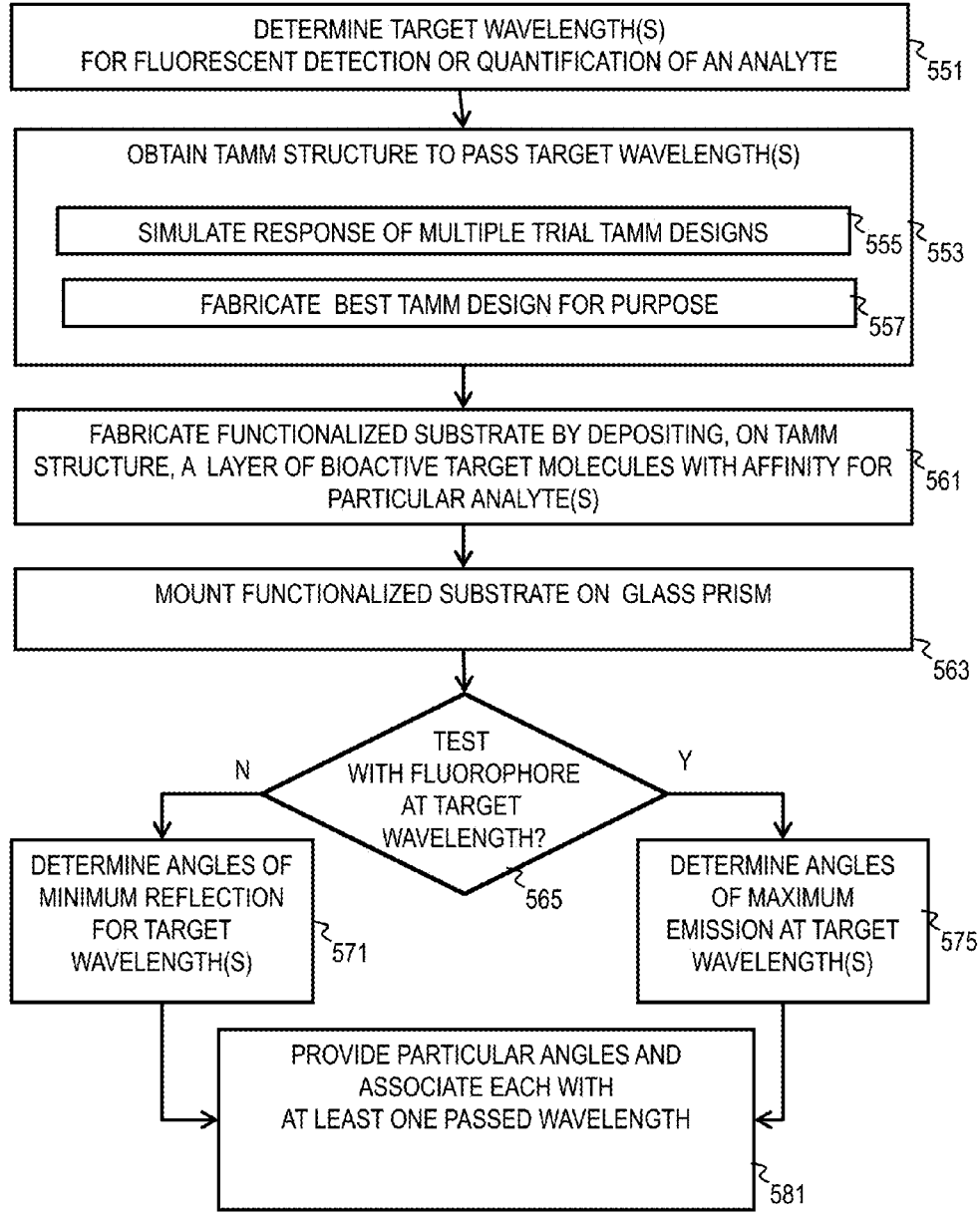

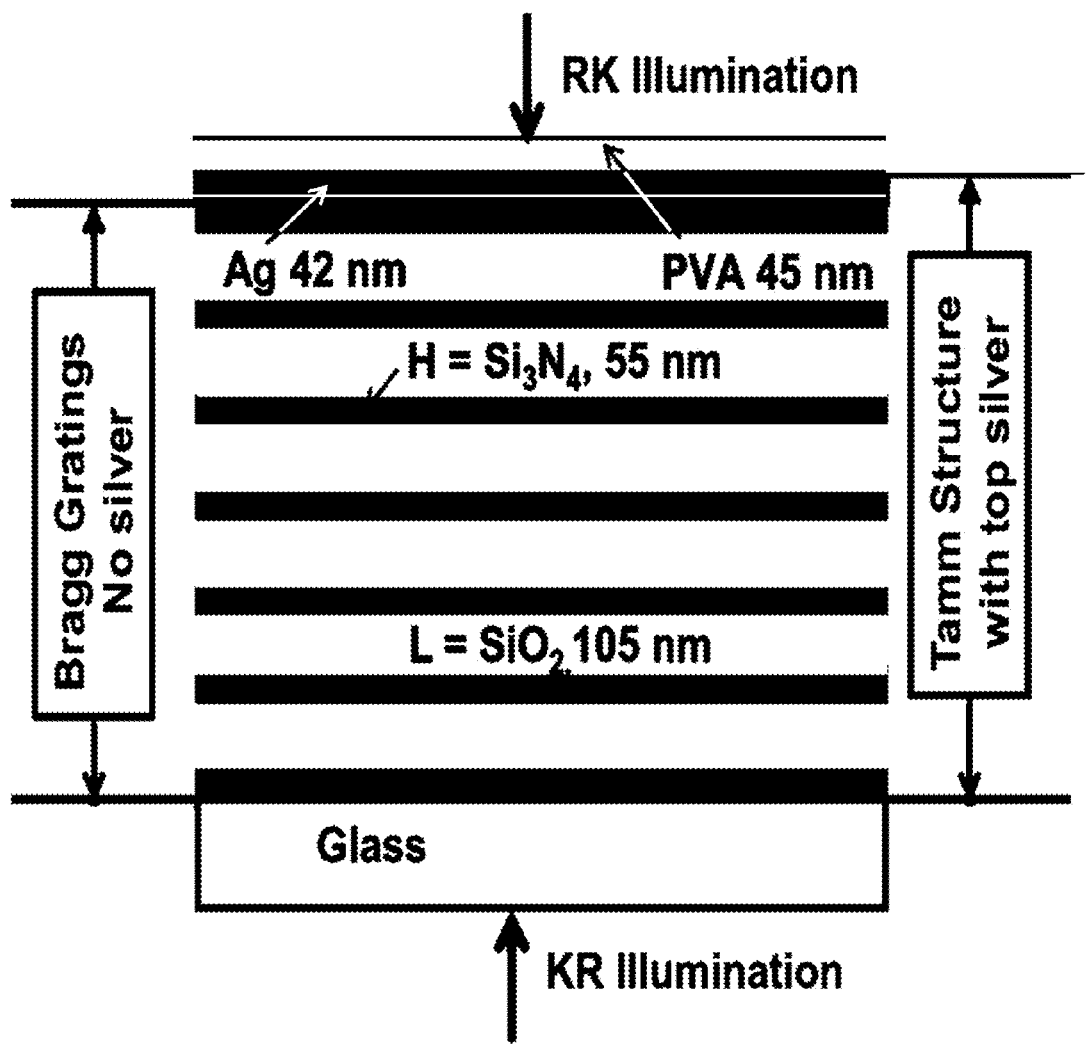

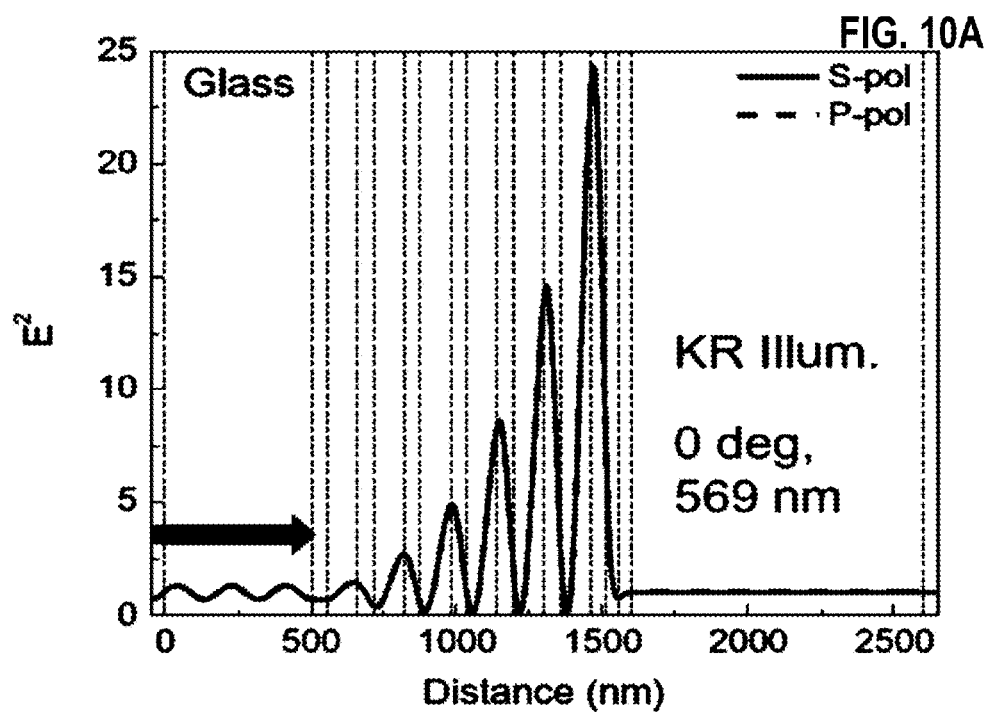
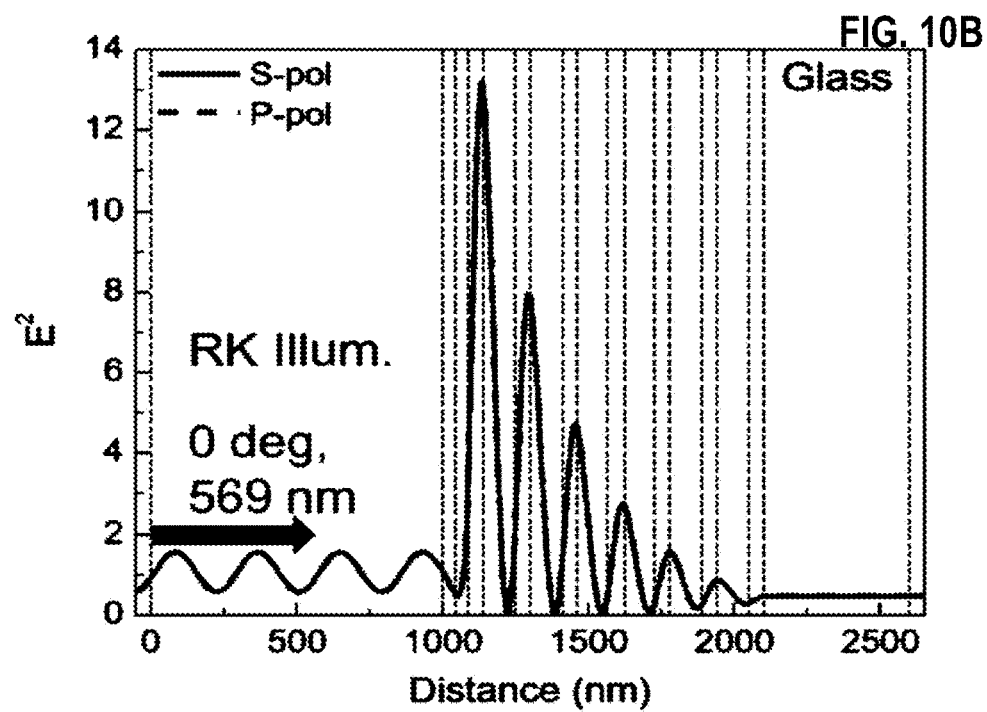

TAMM STRUCTURES FOR ENHANCED FLUORESCENCE BASED SENSING, IMAGING AND ASSAYS

CROSS-REFERENCE TO RELATED APPLICATIONS

This application claims benefit of Provisional Appln. 62/001,655, filed May 22, 2014, the entire contents of which are hereby incorporated by reference as if fully set forth herein, under 35 U.S.C. § 119.

STATEMENT OF GOVERNMENTAL INTEREST

This invention was made with government support under Grant Numbers HG002655, EB006521, and HG005090 awarded by the National Institutes of Health. The government has certain rights in the invention.

BACKGROUND

In affinity assays, a known quantity of a labeled probe competes with or binds to an unknown quantity of unlabeled analyte at binding sites on a target molecule for which the analyte has an affinity. The labeled probe that is bound to the target molecule presents a different measurable phenomenon than the labeled probe that is unbound. Calibration curves relate the presence or quantity of the analyte to the relative amount of bound to unbound labeled probe. The calibration curves are generated by measuring the relative amounts of bound and unbound labeled probe in the presence of known quantities of analyte. In sandwich binding assays, the probe binds to the analyte that is bound to the target molecule. In immunoassays, the analyte is an antigen and the target molecule is an antibody.

In some approaches, the target molecule is affixed to a substrate with properties that causes the emissions from the label to be distinguishable from emissions from a label that is not bound to the target so that the label is displaced farther from the substrate.

During the past decade, there has been a growing interest in plasmonics and in the near-field interactions of fluorophores with metallic structures. Metallic surfaces and particles display surface plasmons, which can result in enhanced and selective excitation of nearby fluorophores. A plasmon is an oscillation of free electron density in a metal particle which can form waves on metal surfaces with the same electric fields and frequencies but shorter wavelengths than electromagnetic waves. In addition, these nearby excited state fluorophores can interact with the photonic mode density (PMD) created by the plasmons, which increases the emission rates and decreases the lifetimes. The PMD is also referred to as the density of states (DoS). The spatial distribution of light from the fluorophore can be changed from the usual omnidirectional distribution to a more narrow spatial distribution, which is determined by wave vector matching at the metallic surfaces. This phenomenon is called surface plasmon-coupled emission (SPCE), and provides an opportunity to increase the brightness of fluorophores by coupling both excitation and emission to surface plasmons, which can result in metal-enhanced fluorescence (MEF).

The use of metals with fluorescence does have some disadvantages. For metal-enhanced fluorescence (MEF), the metal must display a plasmon resonance at wavelengths where its intrinsic absorption is low. This limits the practical metals to Ag, Au, and Al, with a few other metals in occasional use for MEF. There is an optimal distance for metal enhancement near 10 nm from the metal surface because fluorophores at closer distances are often quenched. Metals are lossy and quickly dissipate the optical energy. As a result, MEF often occurs with an increased excitation-relaxation cycling rate. Furthermore, the excitation and emission angles are far from normal, making use for imaging applications problematic.

SUMMARY

It has been determined that improved techniques are desirable for measuring fluorescent emission in biological detection, imaging and assays. Techniques are provided for using a TAMM structure as a substrate for enhanced fluorescence based sensing, imaging and assays that alleviate one or more deficiencies of prior art approaches. Note in the following that S polarized light has an electric field that is both perpendicular to the direction of propagation and parallel to a surface of a substrate; while P polarized light is perpendicular to both the direction of propagation and to the S polarized electric field, which involves a component perpendicular to the surface of the substrate at off-normal angles of propagation.

In a first set of embodiments, a Tamm substrate for a target optical frequency comprises a metal nanoscale layer deposited on a Bragg grating. The Bragg grating includes multiple dielectric layers including multiple high index of refraction layers alternating with multiple low index of refraction layers. The dielectric layers are parallel to the metal nanoscale layer; and, the thickness of each dielectric layer is about a fourth of a wavelength of the target optical frequency in the layer. The metal nanoscale layer is configured to host a fluorophore such that an S polarized emission from the fluorophore at the target optical frequency propagates out of the substrate perpendicular to the plurality of dielectric layers.

In some embodiments of the first set, the metal nanoscale layer comprises a nanoporous metal film with a pore size large enough to accommodate a molecular complex that includes the fluorophore, or the metal nanoscale layer includes nanoscale holes that expose an adjacent dielectric layer of the plurality of dielectric layer, each hole large enough to accommodate a molecular complex that includes the fluorophore. Nanoporous metal films have pores with a dimensions in a range from 1 to 1000 nanometers (nm, 1 nm=$10^{-9}$ meters).

In some embodiments of the first set, a first dielectric layer adjacent to the metal nanoscale layer is a high index of refraction layer. For emissions from the fluorophore hosted by the metal nanoscale layer and excited by incident light, there is an emission intensity maximum centered at a non-zero angle independent of the direction of the incident light for a different optical frequency than the target optical frequency.

In some embodiments of the first set, the metal nanoscale layer is functionalized with a bioactive target molecule that has an affinity for a particular analyte. In some of these embodiments, the fluorophore is complexed with the bioactive target molecule during a detection or assay or imaging of the particular analyte.

In a second set of embodiments, a fluorescence affinity assay kit for determining the quantity of a particular analyte includes the Tamm substrate, a solution and a reagent. The solution includes a bioactive target molecule that has affinity for a particular analyte, wherein the target molecule includes a ligand for affixing to the substrate. The reagent includes at least one set of substantively identical detection molecules that each include the fluorophore. The detection molecule has affinity for the particular analyte.

In some embodiments of the second set, the reagent also includes a different detection molecule for a different analyte with a different fluorophore that fluoresces at a different optical frequency from the target optical frequency, The substrate produces an emission intensity maximum centered at a non-zero angle independent of the direction of the incident light for the different optical frequency.

In a third set of embodiments, a system includes a source of incident light, the Tamm substrate, an optical coupler and a detector. The substrate is configured to be placed in contact with a mixture of a sample and a reagent. The reagent includes a detection molecule for the particular analyte with a fluorophore that fluoresces sufficiently near the target optical frequency to produce a S polarized emission that propagates out of the substrate. The optical coupler is configured to direct incident light onto the substrate; and, the detector is configured to measure fluorescent emissions from the substrate.

In some embodiments of the third set, the detector comprises a photo array to record an image of the fluorescent emissions from the substrate. In some embodiments of the third set, the substrate produces an emission intensity maximum centered at a different non-zero angle independent of the direction of the incident light for each different optical frequency from the target optical frequency. In these embodiments, the detector is configured to detect fluorescent emissions at a plurality of different angles from the substrate. In some embodiments of the third set, the system includes a polarizer disposed in an optical path between the substrate and the detector, wherein the polarizer passes only S polarized light.

In a fourth set of embodiments, a method includes providing a functionalized substrate for a target optical frequency made up of the Tamm substrate functionalized with a bioactive target molecule that has an affinity for a particular analyte. The method also includes providing a reagent comprising a detection molecule for the particular analyte, wherein the detection molecule includes a fluorophore that fluoresces at the target optical frequency. The method further includes determining a calibration curve that relates detection or quantity of the particular analyte to at least one of intensity or direction or polarization of fluorescent emissions at the functionalized substrate in response to incident light for a plurality of known concentrations of the particular analyte mixed with the reagent. The method still further includes contacting a sample and the reagent to the functionalized substrate. Yet further, the method includes, obtaining measurements of at least one of intensity or direction or polarization of fluorescent emissions at the functionalized substrate in contact with the sample and reagent in response to the incident light. Still further, the method includes determining a presence or quantity of the particular analyte in the sample from the calibration curve and the measurements.

In some embodiments of the fourth set, the reagent further comprising a different detection molecule for a different analyte, wherein the different detection molecule includes a different fluorophore that fluoresces at a different optical frequency from the target optical frequency and the substrate produces an emission intensity maximum centered at a non-zero angle independent of the direction of the incident light for the different optical frequency.

In other sets of embodiments, an apparatus or a non-transitory computer-readable medium is configured to perform one or more steps of the above method.

Still other aspects, features, and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The present invention is illustrated by way of example, and not by way of limitation, in the figures of the accompanying drawings, in which like reference numerals refer to similar elements, and in which:

FIG. 3A is a block diagram that illustrates an example enhanced competitive binding assay during operation, according to an embodiment;

FIG. 3B is a block diagram that illustrates an example enhanced sandwich binding assay during operation, according to an embodiment;

FIG. 4B and FIG. 4C are block diagrams that illustrates example enhanced fluorescence multiplexed imaging systems using a Tamm structure, according to various embodiments;

FIG. 5A and FIG. 5B are flow charts that illustrate an example method to perform an enhanced fluorescence assay using a Tamm structure, according to an embodiment;

FIG. 7 is a block diagram that illustrates an example Tamm structure, according to an embodiment;

FIG. 10A and FIG. 10B are graphs that illustrate example computed electric field intensity dependence on position within a Tamm structure, according to various embodiments;

DETAILED DESCRIPTION

Figure 1A:
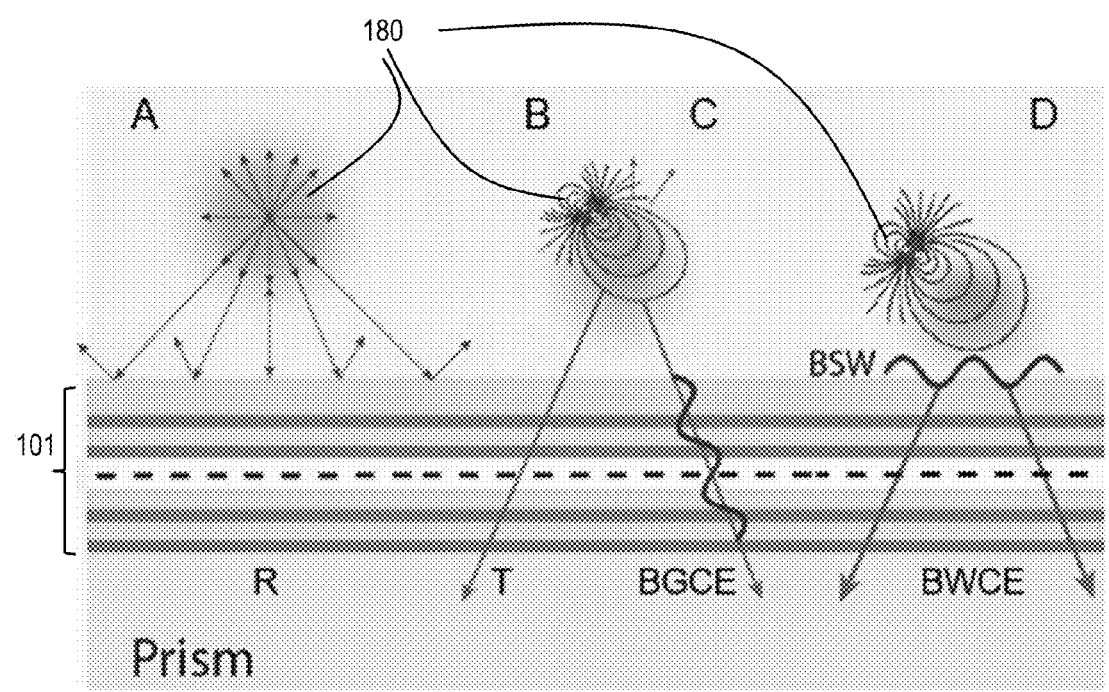
FIG. 1A is a block diagram that illustrates example interactions of a fluorophore with a Bragg grating, also called a one dimensional photonic crystal (1DPC), which is a component of a Tamm structure according to various embodiments.

Techniques are described for enhanced fluorescence based sensing, imaging and assays using one dimensional photonic crystals. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements. Unless otherwise clear from the context, a numerical value presented herein has an implied precision given by the least significant digit. Thus a value 1.1 implies a value from 1.05 to 1.15. The term "about" is used to indicate a broader range centered on the given value, and unless otherwise clear from the context implies a broader range around the least significant digit, such as "about 1.1" implies a range from 1.0 to 1.2. If the least significant digit is unclear, then the term "about" implies a factor of two, e.g., "about X" implies a value in the range from 0.5× to 2×, for example, about 100 implies a value in a range from 50 to 200. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Some embodiments of the invention are described below in the context of fluorescent assays in the presence of a particular Tamm structure. However, the invention is not limited to this context. In other embodiments, the Tamm structure is used in a substrate for simple detection of one or more analytes or for intensity imaging multiple analytes simultaneously on different portions of the substrate, or at different optical frequencies, or some combination, and any Tamm structure may be used in the substrate. Furthermore, any fluorophore may be used to label a detection molecule used to determine binding of analyte to target molecule. In various embodiments, the Tamm structure is used for multiplex or array applications, such as DNA hybridization, gene chips, protein arrays, high-throughput screening, drug discovery and clinical assay. The measurements can be further multiplied by using the wavelength-dependent angles for the coupled emission. The Tamm structure has potential applications in LED technology.

Furthermore, as described herein, the use of Tamm structures implies different index of refraction (n) in different layers. While the optical frequency is constant in each layer, the speed and hence the wavelength is inversely proportional to the index of refraction. Because the optical spectrum is usually described in terms of the optical wavelength in a vacuum (n=1), which is about the same as the wavelength in air (n=1.000293 at a wavelength of 589.29 nanometers), the term "wavelength" is used for convenience to mean the wavelength in air, unless otherwise stated explicitly (such as "the wavelength in a layer of the 1DPC"). Thus the wavelength of incident light is the wavelength in air of the optical frequency of the incident light, which wavelength changes as the incident light penetrates the Tamm structure or other material, such as the sample or glass; and, the wavelength of a fluorescent emission is the wavelength in air of the optical frequency of the emission, which wavelength also changes as the emission penetrates the Tamm structure or other material.

1. Definitions

As used in this description, the following terms have the meanings given here.

| | |
|---|---|
| 1DPC | One dimensional photonic crystal, multiple layers of alternating high and low index of refraction dielectric layers with thicknesses related to wavelength in the layer of a target optical frequency, also called a Bragg grating |
| amino acids | An organic molecule comprising both carboxyl and amino groups that can form peptide bonds with complementary groups on other amino acids. 22 amino acids comprise all the proteins found in most living organisms. |
| analyte | a component of a sample for which a quantity is to be determined, including but not limited to a polymer, a ligand, an antigen, an antibody, a protein, a peptide, DNA, RNA, oligonucleotide, a virus or a bacterium. |
| assay | a method to determine the quantity (e.g., the presence, absence, or concentration) of one or more components called analytes in a test sample. |
| assay kit | a collection of materials to be used in an assay. |
| BG | Bragg grating (see 1DPC) |
| BGCE | Bragg grating coupled emissions, emission from a fluorophore affected by evanescent states in an adjacent Bragg grating |
| BWCE | Boch surface wave coupled emissions, emission from a fluorophore affected by surface waves in an adjacent Bragg grating |
| concentration | a fraction of a sample by weight or volume which is due to a component of the sample. |
| detection molecule | a molecule labeled with a fluorophore that is used to detect binding of an analyte to a target molecule by binding to the analyte or by competing with the analyte for binding sites on the target molecule. Also called a probe-fluorophore conjugate or probe-dye conjugate. |

| | |
|---|---|
| FL | Fluorescein, a fluorophore with peak emission at 520 nm |
| fluorophore | a functional group in a molecule which absorbs electromagnetic waves at a specific wavelength and subsequently emits electromagnetic waves at a different specific wavelength. Fluorophores include, but are not limited to, fluoresceins, eosin, coumarines, rhodamines, cyanines, benzophenoxazines, phycobiliproteins or fluorescent proteins. |
| functionalized substrate | a substrate that is conditioned to perform a particular function by deposition of layers of one or more types of molecules, such as a glass slide coated with bioactive molecules that facilitate fixing of an analyte to the substrate. |
| ligand | a functional group in a molecule which binds to a metal, generally involving formal donation of one or more of its electrons. Metal-ligand bindings range from covalent bonds to electrostatic attraction between ions (ionic bonding). |
| light | electromagnetic (em) waves in a visible portion of the electromagnetic spectrum, which includes wavelengths in air from about 300 to about 800 nanometers (nm, 1 nm = $10^{-9}$ meters). |
| nanoparticles | particles each having a dimension in a size range from about 1 to about 1000 nanometers, nm. 1 nm = $10^{-9}$ meters. |
| NPM | Nanoporous metal, a metal film with pore sizes on the nanoscale (1 to 1000 nm) |
| PBG | Photonic band gap, a band of optical frequencies that will not penetrate in a 1DPC (Bragg grating) and are totally reflected |
| plasmon | an oscillation of free electron density in a metal particle which can form waves on metal surfaces with the same electric fields and frequencies but shorter wavelengths than incident electromagnetic waves. Metal surface plasmons with frequencies in the visible spectrum can interact with light. |
| Plasmonic substrate | A substrate that includes a layer of metal nanoparticles that form plasmons with frequencies in a spectral band of one or more fluorophores |
| probe | a molecule that is used to detect binding of an analyte to a target molecule by binding to the analyte or by competing with the analyte for binding sites on the target molecule (the portion of a detection molecule excluding the fluorophore). Probes include, but are not limited to, a polymer, a ligand, an antigen, an antibody, a protein, an oligomer, a protein, a peptide, DNA, RNA or an oligonucleotide. |
| probe-fluorophore conjugate | A detection molecule. |
| protein | A large molecule made up of a long chain of amino acids. Shorter chains of amino acids are called peptides or protein fragments. |
| reagent | substance or compound consumed during a chemical reaction. |
| Rh6G | Rhodamine 6G, a Rhodamine family fluorophore with a peak emission at 546 nm |
| RhB | Rhodamine B, a fluorophore with a peak emission at 569 nm. |
| S101 | Sulforhodamine 101, a fluorophore with peak emission at 600 nm |
| solution | a liquid mixture. |
| SPCE | Surface plasmon coupled emissions, emission from a fluorophore affected by nanoscale metal film over a dielectric layer |
| SPR | Surface plasmon resonance, a configuration of wavelength and angle that causes light to interact with plasmons |
| substrate | a material on which a process is conducted |
| Tamm structure | A metal film deposited on multiple layers of alternating high and low index of refraction dielectric layers with thicknesses related to wavelength in the layer of a target optical frequency |
| target molecule | a molecule which has an affinity for a particular analyte. Target molecules include, but are not limited to, a polymer, a ligand, an antigen, an antibody, a protein, a peptide, DNA, RNA, an oligonucleotide. Also called a capture molecule. |
| test sample | a sample, such as a biological sample, with an unknown quantity of an analyte |
| TSCE | Tamm state coupled emissions, emission from a fluorophore affected by Tamm states in an adjacent Tamm structure |

2. Overview

Advantages have been discovered in the use of near-field interactions of fluorophores with Tamm structures formed by depositing a nanoscale metal layer on dielectric photonic crystals (PCs). PCs are defined according to their dimensionality. One-dimensional (1D) PCs are made up of multiple layers of dielectrics with different refractive indexes. Well-known examples include Bragg gratings (BGs) or notch filters for optical spectroscopy. PCs have unusual optical properties because they can display photonic band gaps (PBGs), which are optical frequencies (or wavelengths) that cannot propagate in a given structure. As a result, the PBGs give a colored appearance to structures without the presence of chromophores. The local radiative density of states (LRDoS) increases near the edge of a PBG and then becomes smaller and approaches zero at the PBG. This is important for measurements of fluorescence because the rate at which an excited fluorophore loses energy to the PC increases with an increase in the LRDoS.

A one-dimensional photonic crystal (1DPC) is robust and easy to fabricate using only vapor deposition methods, although other methods can also be used. A 1DPC consists of multiple layers of dielectrics with alternating low (L) and high (H) dielectric constants. The dielectric constant κ is equal to the square of the index of refraction, n. These structures can display a partial PBG and become completely reflective for particular wavelengths and incidence angles. However, this complete reflection refers to plane wave light incident from the far field.

Previous studies of fluorophores near metallic structures showed that fluorophores in the near field can interact with metals when plane wave illumination at the same frequency is reflected and the phenomenon is called surface plasmon-coupled emission (SPCE). It was found that fluorophores can also undergo near field interactions and couple with modes of the 1DPC at the same wavelengths (optical frequencies) at which far field illumination results in reflection. These interactions were found to modify the directionality and polarization of the coupled emission. This phenomenon is called herein Bragg grating-coupled emission (BGCE). As described herein, a similar near field effect occurs with Tamm structures, but with very different characteristics.

There are several potential advantages when using dielectric structures, including Tamm structures. Metals are lossy, meaning that they rapidly dissipate energy. Dielectrics dissipate less energy than metals, which can allow sharp resonances and strong local fields. Fluorophores will not be quenched when close to the surface of a dielectric; hence, enhanced emission is possible for the entire evanescent field, not just the region beyond 3 nanometers (nm, 1 nm=10$^{-9}$ meters) from the surface as observed for metal structures. A wide variety of dielectrics are available to cover a wide range of wavelengths, and the optical properties (e.g., n) can scale closely with dimensions. In addition, the substrates are not as fragile as metal surfaces and can be cleaned and used multiple times.

Excited state fluorophores can interact with 1DPCs in several ways. FIG. 1A is a block diagram that illustrates example interactions of a fluorophore 180 with a one dimensional photonic crystal (1DPC) 101, according to various embodiments. If the fluorophore 180 is more than approximately 1 wavelength away (panel A), the energy propagates as free space radiation. If the wavelength overlaps with the PBG, it is reflected (R). This effect was used in several studies as a way to collect a greater fraction of the emission from a fluorophore. Alternatively, if the wavelength is much longer or much shorter than the thickness of the layers (panel B), e.g., by a factor of about four, the light can be transmitted (T). If a quarter of the wavelength is comparable to the layer thickness, and the emitter is within one wavelength of the 1DPC (panel C and panel D), then the emission can display near-field coupling with optical modes of the 1DPC.

One type of optical mode is made up of internal modes of the 1DPC (panel C). At first glance, it seems that this energy would be trapped by total internal reflection (TIR). However, as shown below, the majority of the radiation appears below the substrate as 1DPC coupled emission. This effect might occur because these modes are leaky, which depends on imperfections in the structure. A cone of emission and its angles in the substrate are expected to be dependent on wavelengths so that the 1DPC also provides spectral separation, as shown in some example embodiments below.

Another type of optical mode is made up of surface states on PCs (panel D). These surface states were recognized only recently, and their use in applications is even more recent. In these states, the electromagnetic energy is trapped on the surface. The energy cannot propagate into the sample because of the PBG and cannot radiate away from the surface because of TIR. These states are called Bloch surface waves (BSWs). The BSWs are analogous to surface plasmons, which are also surface-trapped states. Because of the low losses in dielectrics, the BSWs display high-quality factors and very sharp angular resonances. This provides an opportunity for nearby fluorophores to interact with these surface modes and display BSW-coupled emission (BWCE). BSWs provide opportunities both for selective excitation of surface-bound fluorophores and for a sharp angular distribution in the coupled emission. Although not stated explicitly, BSWs may have contributed to recently reported increased rates of excitation. Because of these unusual effects, 1DPCs offer opportunities for new formats for fluorescence detection and sensing.

BGCE and SPCE share at least one disadvantage. In both cases, the emission appears at large angles relative to the surface normal. These angles are above the critical angle (outside the light cone), which in turn requires immersion objectives for efficient collection of the emission. In addition, incident light from the air cannot interact with these resonances. A prism or grating coupler is needed to increase the wave vector of the incident light.

1.1 Tamm Structure Substrate

A structure that contains features of both plasmonic and photonic components is here explored to allow both excitation and emission to occur within the light zone at angles less than the critical angle. In fact, depending on dimensions and wavelengths, the emission can be directed either away from or back through the structure at directions perpendicular to the surface. FIG. 1B through FIG. 1E, are block diagrams that illustrate example interactions of a fluorophore with a Tamm structure, according to various embodiments.

Figure 1B:
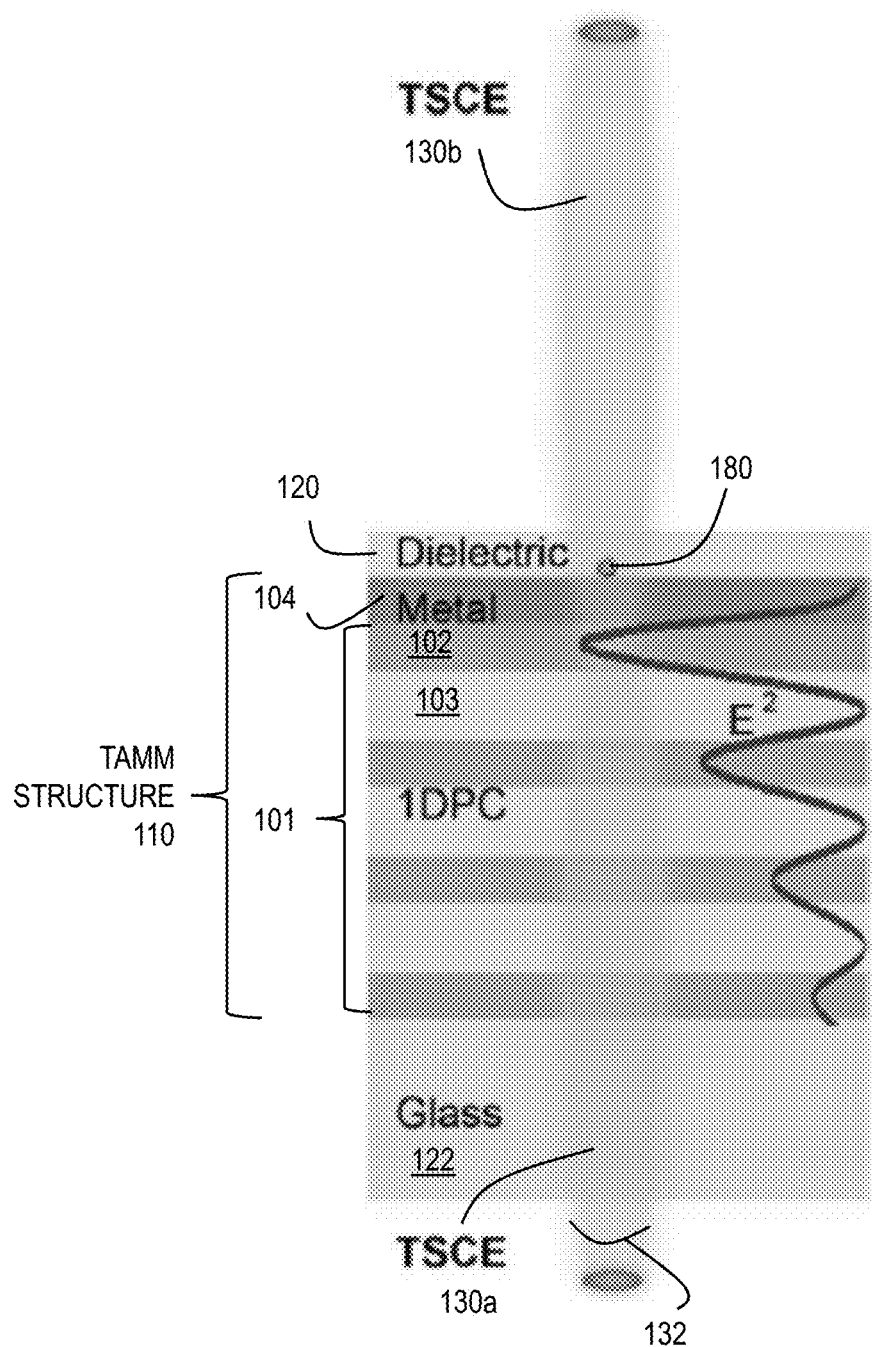
FIG. 1B through FIG. 1E, are block diagrams that illustrate example interactions of a fluorophore with a Tamm structure, according to various embodiments.

FIG. 1B shows the Bragg grating 101 of FIG. 1A, with high index of refraction layers 102 and low index of refraction layers 103 covered by a metal layer 104 to form the Tamm structure 110. The structure is depicted as supported on a glass base 122 but the glass 122 is not part of the Tamm structure 110. A fluorophore 180 positioned above the metal layer 104, such as in a sample layer like dielectric sample layer 120, can be made to couple with the states of the Tamm structure 110 to form electric fields ($E^2$) that leave the structure 110 as light beams that are narrow and perpendicular to the layers of the Tamm structure. In effect, the Tamm structure concentrates and collimates a fluorescence emission that would be omnidirectional in free space. Unlike SPCE and BGCE, the angles of emissions from normal are not large. In some embodiments, as shown in more detail below, there is a separation of wavelength across the angular width 132 of the beam.

In various embodiments, the excitation light for the fluorophore 180 is incident on the sample from either direction and perpendicular to the surface. In contrast to surface plasmon resonance (SPR) or SPCE, neither a prism nor a grating coupler is needed. These unusual possibilities are the result of the relatively unknown phenomenon of optical Tamm states. Tamm states are named after Igor Tamm, who described their existence at the atomic scale and linked them to the periodicity of the atoms in a crystal. It was not until 2005 that similar optical states were shown to exist between two BGs and between a metal film and a BG. Each of the states between two dielectric BGs is usually called an optical Tamm state (OTS). Each of the states between a BG and a metal film is often called Tamm plasmons or Tamm plasmon polaritons to indicate the involvement of electron oscillations. An advantage of a plasmonic Tamm state over OTS is that the OTS requires a prism coupler. A prism is not needed for the structure described herein. As is shown below, the electric fields for the Tamm states are usually localized below the metal film, just below the metal-dielectric interface. For this reason, the states are simply called Tamm states herein in order to avoid specifying the role of the plasmons in the Tamm fields.

Tamm states have unusual properties that can be advantageous for use in sensors and the next generation of fluorescence multiplex arrays and device formats. The creation of surface plasmons on a metal film requires the light to be incident on the sample at the SPR angle ($\theta_{SPR}$). The light must also be incident though a prism and be P polarized. S polarized light does not create plasmons, nor does light incident at any angle from the air side of the sample. The surface plasmons are localized at the metal-air (sample) interface with evanescent fields in both the metal and air (sample) regions. In contrast, Tamm plasmons can be created by perpendicular incident light or at other angles with either S polarized or P polarized incident light. Surface plasmons must have an in-plane (x-axis) component of the wave vector. A Tamm plasmon can be S polarized or P polarized, and the in-plane wave vector can be zero. This absence of in-plane propagation offers the opportunities for "slow light," which can increase the interactions with fluorophores.

Tamm plasmons do have a disadvantage, which is that the modes are under the metal film (see the electric field peaks in FIG. 1B). Because of this field location, one might predict that the Tamm plasmons would be unable to interact with fluorophores above the metal. It is shown herein that fluorophores above the metal surface can couple with the Tamm plasmons to yield Tamm plasmon-coupled emission perpendicular to the sample plane. It is believed that the combination of plasmonic and photonic components in a single structure offers new opportunities for novel device formats for applications of fluorescence to the biosciences.

These Tamm structures can provide for control of light and fluorescence at nanoscale dimensions. Multiple layers of metals and dielectrics that can also provide directional emission normal to the surfaces were recently described. A structure displaying a Tamm state is described that can be accessible within the light cone or even with incidence normal to the surface. Unambiguous evidence was found for TSCE normal to the surface and at small angles away from the normal axis.

Although an experimental Tamm structure displayed emission normal to the surfaces, the intensities were not as high as were observed previously with SPCE. It was reasoned that the less intense TSCE is due to the Tamm electric fields being localized under the top metal layer, and mostly in the top dielectric layer, and also to the leaky nature of the Tamm state in both directions. Thus, in some embodiments, several structural adjustments are made to increase the TSCE intensity, as depicted in FIG. 1C through FIG. 1E.

Figure 1C:
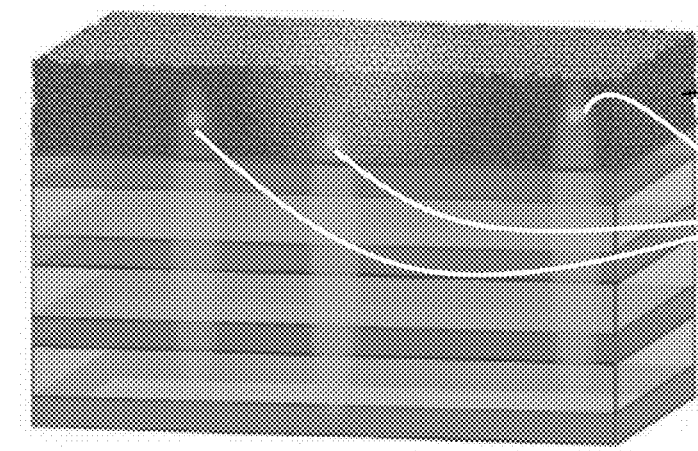

FIG. 1C shows a BG with a nanoporous metal film 105a approximately 100 nm thick, which is roughly twice the thickness used for SPR and SPCE. Nanoporous films have pores with dimensions on the nanoscale (1 nm to 1000 nm). Nanoporous films of Al, Ag, and Au can be readily formed by electrochemical or etching procedures. The pore size in nanoporous metals (NPMs) can easily be larger than typical biomolecules labeled with fluorophores 180, so that the biomolecules can diffuse to the interface with the adjacent dielectric layer and have the fluorophores be exposed to the Tamm field. It is known that typical angle-dependent SPRs can be observed with void volumes as large as 50% of the NPMs. Hence, it seems likely that the Tamm states will continue to exist for a BG coated with an NPM film.

Figure 1D:
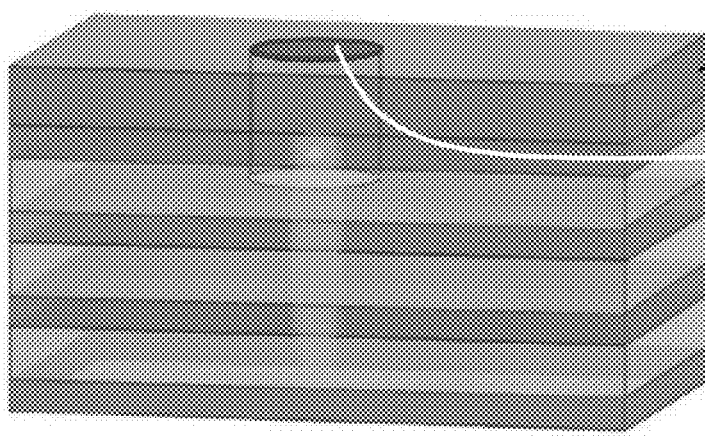

In another embodiment, nanoholes that go through the top metal film 105b and possibly into the underlying BG are included in the Tamm structure, as depicted in FIG. 1D. A nanohole is a hole with dimensions in the nanoscale (1 nm to 1000 nm) and is represented schematically as nanohole 106a. However, typical nanoholes are approximately 100 to 200 nm in diameter, and these sizes result in enhanced fluorescence. In some embodiments, such nanohole Tamm structures are used in single-strand DNA sequencing. In this application, the sample is illuminated from the bottom through an underpinning glass slide. The metal films for sequencing are usually approximately 200 nm thick because such a thickness is useful to suppress emission from the sample side of the metal film that contains high concentrations of labeled nucleotides. A thicker metal film does not disrupt the Tamm state. In fact, simulations have shown that, compared with the 42-nm Ag film used in the example embodiment described below, the Tamm field intensities increase more than 3-fold if the metal thickness is increased to 125 nm or 900 nm.

Figure 1E:
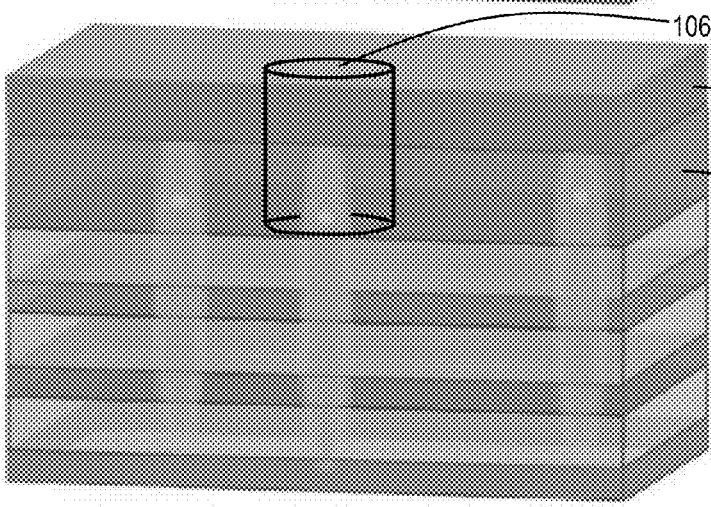

In another embodiment depicted in FIG. 1E, the thickness of the top dielectric layer 108 is increased to make more room for the labelled biomolecules from the sample that have entered through the nanoholes 106b or nanoporous metal film 105a. This increase is possible because Tamm states were shown to exist with the top dielectric being up to 2 microns thick (1 micron=1 micrometer, μm, =$10^{-6}$ meters).

For all three structures shown in FIG. 1C through FIG. 1E, it is expected that some of the TSCE is also directed out the top of the structures. These considerations suggest that Tamm states can exist in a variety of metals. BG structures can be modified for a variety of sensing applications.

Figure 2:
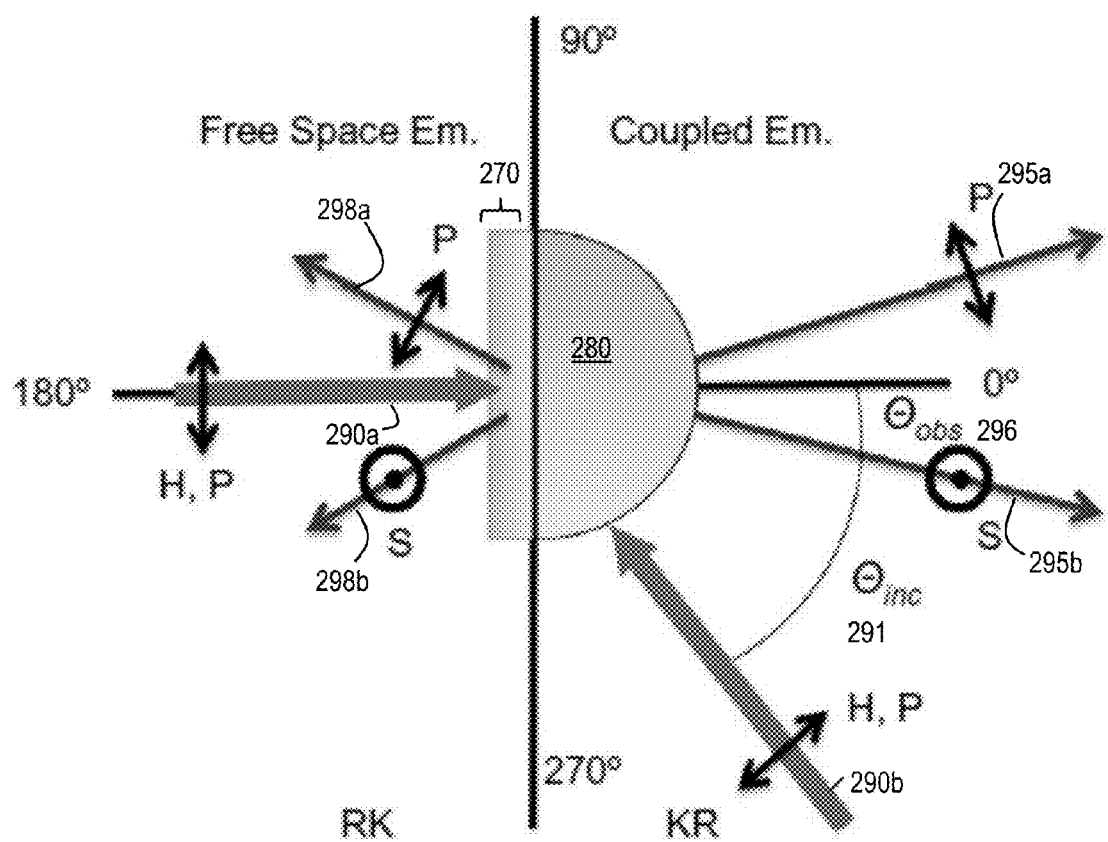
FIG. 2 is a block diagram that illustrates an example coordinate system for describing emissions from fluorophores on a Tamm structure when excited by incident light, according to various embodiments.

FIG. 2 is a block diagram that illustrates an example coordinate system for describing emission cone from fluorophores on a 1DPC when excited by incident light, according to various embodiments. The geometry and polarization conditions of the measurements are depicted in FIG. 2. An arbitrarily chosen vertical axis in the laboratory corresponds to the out-of-plane axis in FIG. 2. A rectangular Tamm substrate 270 is placed on a hemi-cylindrical prism 280 with an index matching fluid and cylindrical axis parallel to the vertical axis (out of the page). This prism is not necessary with a Tamm state, but was retained to obtain results comparable with previous measurements on metal films and 1DPCs, and to avoid changes in angle of the incident light or the emission.

Two modes of excitation were used. Excitation light 290b incident on fluorophores after passing through the Tamm substrate 270 is called the Kretschmann (KR) configuration, and in some embodiments is incident above θc to allow selective excitation of fluorophores adjacent to the top surface of the Tamm substrate 270 opposite the surface of the Tamm substrate 270 that abuts the glass prism 280. In some embodiments, the substrate is also, or instead, excited with illumination 290a that does not first pass through the Tamm substrate 270, which is called the reverse Kretschmann (RK) configuration. In this case, fluorophores are excited through the entire thickness of the sample by light that has not passed through the Tamm substrate 270, and the incident light is reflected by the Tamm substrate 270 as reflected light (not shown). The emissions from the excited fluorophores can be observed from either side of the substrate 270. Emission measured through the Tamm substrate 270 is referred to as coupled emission or KR emission and depicted as P polarized 295a and S polarized 295b in different direction for convenience (collectively referenced herein after as coupled emissions 295); and, the emission that does not pass through Tamm structure 270, is called free space emission or RK emission and depicted as P polarized light 298a and S polarized light 298b in different direction for convenience (collectively referenced herein after as free space emissions 298). The emission through the Tamm substrate 270 is expected to be polarized due to coupling to various modes in the Tamm substrate 270. An angle of 0 degrees (°) is perpendicular to the KR side of the sample on the Tamm substrate. An angle of 180° is perpendicular to the RK or air side of the sample on the Tamm substrate.

When describing Bragg grating (BG) structures, the S- and P-polarizations are defined relative to the planar surfaces of the substrate—S being parallel to those surfaces and P being perpendicular to the S direction. (Note that both S and P are perpendicular to the direction of propagation of the emission). Hence, the E-field for S-polarized light is parallel to the surfaces, and P-polarized light has its E-field across the interfaces. Because the out-of-plane axis is the laboratory vertical axis, S is referred to as vertically (V) polarized and P is referred to as horizontally (H) polarized. In the RK configuration, illumination was normal to the sample plane (from direction 180 degrees), but the same definitions for V and H were used to indicate the incident polarization relative to the observation polarization. Here vertical can be any direction relative to the direction of gravity. In some embodiments, the structure is used to analyze a liquid sample, and it is convenient for the direction from 180 degrees to be in the direction of gravitational acceleration.

As shown herein, these properties can be used to design a new family of sensors, assays or imagers for direct quantification of analytes, at even very small concentrations, such as associated with cytokine secretion from a single cell, and in real-time.

1.2 Tamm Structure Competitive Binding Assay

In some embodiments, the functionalized Tamm substrate 270 is used in a Tamm structure competitive binding assay. FIG. 3A is a block diagram that illustrates an example Tamm structure competitive binding assay 300 during operation, according to an embodiment. FIG. 3A depicts a portion of a functionalized substrate, including a glass substrate prism 304 and Tamm structure 302. The functionalized substrate of FIG. 3A also includes fixed target molecules 332 for a particular analyte as the fixed bioactive molecules.

The functionalized substrate is in contact with a covering solution 310. The covering solution 310 is a mixture of a test sample and a detection molecule reagent. The test sample includes analyte molecules 320 that do not contain a fluorophore. The reagent includes detection molecules comprising analyte molecules 320 labeled with a fluorophore 330. In other embodiments, the detection molecule comprises a fluorophore and a molecule that is different from the analyte, but competes with the analyte for binding sites on the target molecules 332.

As shown in FIG. 3A, the labeled and unlabeled analyte molecules 320 compete for binding sites on the fixed target molecules 332, and eventually reach a steady state equilibrium. The combination of the functionalized substrate and covering solution in steady state is called a product of the assay.

The product of the assay is exposed to incident light 340 with an optical frequency that excites fluorescence of the fluorophore 330 and selected to couple with the modes of the Tamm structure. In the illustrated example, the functionalized substrate and covering solution are exposed to linearly polarized incident light 340 indicated by dotted arrows.

The labeled analyte molecules are excited by the incident light and fluoresce, emitting light at a different specific wavelength. The fluorophore labels on analyte molecules that are free in cover solution 310 are typically not within one wavelength of the Tamm structure 302 and their emitted light 340 passes directly out of the solution away from the Tamm structure or is reflected without penetrating the Tamm structure, as depicted in FIG. 1A panel A. For example, a labeled analyte in solution emits solution emitted light 342 indicated by a single dot dash arrow. In contrast, the fluorophore labels on analyte molecules that are bound to fixed target molecules 332 are within one wavelength of the Tamm structure, if the sizes of the target molecules, analytes and fluorophores 330 and target optical frequency are appropriately chosen. These emissions will couple with the Tamm structure and be observed at the predetermined angles associated with the target optical frequency for the Tamm structure. The compared reflected and coupled emissions can be used to determine the concentration of the analyte in the sample.

In some embodiments, the Tamm structure is illuminated from below and excites a BSW that only excites the fluorophores 330 bound to the fixed target molecules 332. Again, these emissions will couple with the Tamm structure and be observed at the predetermined angles associated with the target optical frequency for the Tamm structure. The coupled emission intensity can be used to determine the concentration of the analyte in the sample.

The angular distribution of the emitted light is measured using an apparatus like apparatus 400 depicted in FIG. 4. The object 490 is the product of the assay, i.e., the functionalized substrate contacting the covering solution 310. A calibration curve constructed based on measurements made with known concentrations of the analyte can be used to determine the ratio of bound to free labeled analytes for a measured intensity value. Other calibration curves, as is well known in the art, are used to determine a resulting analyte associated with such a ratio of bound to free labeled analyte. The resulting analyte is used to determine the quantity (e.g., the presence, absence or concentration) of analyte in the test sample.

1.3 Tamm Structure Sandwich Binding Assay

In some embodiments, the functionalized Tamm substrate 270 is used in a Tamm structure sandwich binding assay. FIG. 3B is a block diagram that illustrates an example Tamm structure sandwich binding assay 350 during operation, according to an embodiment. FIG. 3B depicts a portion of a functionalized substrate, including the glass prism 304 and Tamm structure 302. The functionalized substrate also includes fixed target molecules 332 for a particular analyte as the fixed bioactive molecules.

The functionalized substrate is in contact with a covering solution 360. The covering solution 360 is a result of a three step process. First the functionalized substrate is contacted to a test sample that includes analyte molecules 370 that are not labeled with a fluorophore. The contact is maintained for sufficient time under conditions that allow the amount of analyte binding to the fixed target molecules 332 to be proportional to the amount of analyte in the test sample. Such times and conditions are easily determined by routine experimentation. Next, the functionalized substrate is washed to remove excess unbound analyte from the test sample. Then the functionalized substrate with bound analyte is contacted to a solution of reagent. The reagent includes detection molecules 372. Each detection molecule 370 includes a fluorophore 380 and a molecule that binds to the analyte 370 at a site on the analyte different from the site that binds the analyte to the fixed target molecule 332. The combination of the functionalized substrata, sandwiched analyte and covering solution in steady state is called a product of the assay. The sizes of the fixed target molecules 332, analyte 370, detection molecule 372 and fluorophore 380, and the target optical frequency are selected so that emissions are within one wavelength of the Tamm structure.

The product of the assay is exposed to linearly polarized incident light at a specific wavelength that excites fluorescence of the fluorophore 380. In the illustrated example, the functionalized substrate and covering solution are exposed to polarized incident light 390 indicated by dotted arrows.

The fluorophores in the detection molecules are excited by the incident light and fluoresce, emitting light at the target optical frequency. The fluorophores on detection molecules that are free in cover solution 360 emit light more than one wavelength from the Tamm structure. For example, a detection molecule in solution emits solution emitted light 392 indicated by a single dot dash arrow. In contrast, the fluorophores on detection molecules that are bound to the analyte that is in turn bound to the fixed target molecules 332 emit light that couples to the modes of the Tamm structure. For example, detection molecules bound to analytes bound to fixed target molecules 332 emit film emitted light 394 indicated by a double dot dash arrow. The collection of these emissions indicates the amount of bound analyte.

Any molecule may be deposited in the bioactive molecule layer. The properties of the functionalized substrate are affected by the bioactive molecule deposited in layer. The molecule should include a functional group to affix the molecule to the substrate, such as a ligand to affix the molecule to a dielectric. The molecule should also be able to bind to a particular analyte of interest. Such a molecule is also called a target molecule for an assay for the analyte. In illustrated embodiments, all the molecules deposited in the layer are substantively identical. In other embodiments, functionalized substrates are designed for multiple analytes and multiple populations of different target molecules are used in the same substrate for corresponding different analytes. Binding events of the different analytes would be marked by fluorophores in corresponding different detection molecules emitting at different optical wavelengths. In various embodiments, target molecules that are deposited in the layer include, but are not limited to a polymer, a ligand, an antigen, an antibody, a protein, a peptide, DNA, RNA, or an oligonucleotide.

The functionalized substrate may be designed for any analyte to bind to an appropriately chosen target molecule. In various embodiments, the analyte includes, but is not limited to, a polymer, a ligand, an antigen, an antibody, a protein, a peptide, DNA, RNA, any form of RNA, an oligonucleotide, a virus, a bacterium or a cell.

1.4 Tamm Structure Fluorescence Measurement System

Figure 4A:
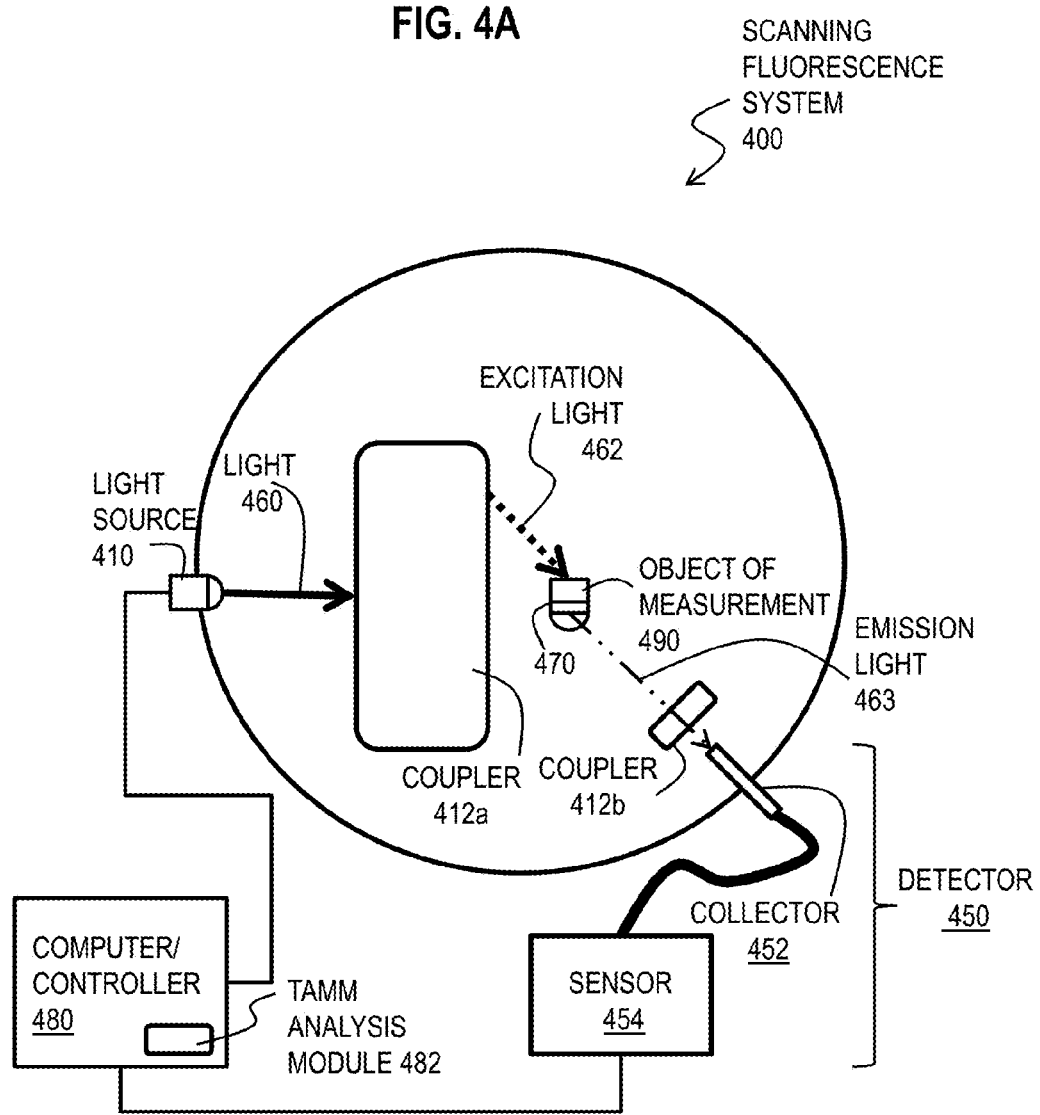
FIG. 4A is a block diagram that illustrates an example enhanced fluorescence measurement system using a Tamm structure, according to an embodiment.

FIG. 4A is a block diagram that illustrates an example enhanced fluorescence measurement system 400 using a Tamm structure, according to an embodiment. Although an object of measurement 490 is depicted in FIG. 4A, the object 490 is not part of apparatus 400, but is operated upon by apparatus 400. In some embodiments, the object 490 is a product formed during an assay described above.

The system includes a source of incident light 410, a functionalized substrate 470, one or more optical couplers 412a and 412b, collectively called optical couplers 412, and a detector 450. The functionalized substrate 470 is configured to be placed in contact with a mixture of a sample and a reagent as an object of measurement 490. The functionalized substrate 470 includes a one dimensional photonic crystal for a target optical frequency and a bioactive target molecule that has an affinity for a particular analyte. The reagent includes a detection molecule for the particular analyte (the detection molecule includes a fluorophore that emits at the target optical frequency and binds to the analyte or the target molecule or both). The optical coupler is configured to direct incident light onto the functionalized substrate 470; and the detector 450 is configured to measure fluorescent emissions from the functionalized substrate 470. In the illustrated embodiment, the detector includes an optical fiber collector 452 and an optical sensor 454, such as a photomultiplier tube or spectral analyzer.

The optical couplers 412 includes one or more of any item that passes or affects an optical beam including any combination of components known in the art that are used to direct an optical beam, such as free space, vacuum, lenses, minors, beam splitters, wave plates and optical fibers, diffraction gratings, circulators, and prisms.

In various embodiments, the light source 410 or the optical coupler 412a or both are configured to be rotated to direct the incident light at one or more angles of incidence to the functionalized layer either by passing through the Tamm structure, e.g., through the glass prism, or directly to the functionalized layer without passing through the Tamm structure. In some embodiments, the detector 450 or coupler 412b or both are configured to be rotated to collect emitted light at one or more angles either by passing through the Tamm structure, e.g., through the glass prism, or directly from the functionalized layer without passing through the Tamm structure.

In some embodiments, the detector is configured for collecting fluorescent emissions in a collection cone that includes an angle of an emission intensity maximum that is independent of a direction of the incident light impinging on the substrate. In some of these embodiments, the coupler 412b includes a polarizer to pass only polarized light to the detector 450. In several of these embodiments, the emission intensity maximum is associated with a Tamm state coupled emission (TSCE) or a Surface Plasmon coupled emission (SPCE) or both.

In some embodiments, the functionalized substrate or coupler 412a includes a glass prism abutting a surface of the one dimensional photonic crystal opposite a functionalized surface with the bioactive target molecule. In some of these embodiments, the optical coupler 412a is configured to direct the incident light to impinge on a surface of the one dimensional photonic crystal through the glass prism and at an angle of minimum observed external reflection. In some of these embodiments, the optical coupler further comprises a polarizer configured to polarize the incident light in a direction parallel to the plurality of dielectric layers.

In some embodiments, the system includes a computer system or other controller configured with a Tamm structure analysis module 482 configured to operate the light source or couplers 412 or detector 450 to collect data to form one or more calibration curves, or to use the calibration curves to perform an assay on the analyte based on the collected emissions.

Although processes, equipment, and data structures are depicted in FIG. 4 as integral blocks in a particular arrangement for purposes of illustration, in other embodiments one or more processes or data structures, or portions thereof, are arranged in a different manner, on the same or different hosts, in one or more databases, or are omitted, or one or more different processes or data structures are included on the same or different hosts.

FIG. 4B and FIG. 4C are block diagrams that illustrates example enhanced fluorescence multiplexed imaging systems using a Tamm structure, according to various embodiments. In these embodiments one or more of the coupler 412a, object of measurement 490, substrate 470, coupler 490 and detector of system 400 are replaced with the corresponding objects depicted in FIG. 4B or FIG. 4C.

In these embodiments the components of system 400 are adjusted for multiplexed, fluorescence imaging, called herein a multiplex fluorescence imaging system, according to an embodiment. The systems are multiplexed because they simultaneously measure the fluorescence emission from multiple different fluorophores that fluoresce at different optical frequencies. The different optical frequencies exit the Tamm structure at different angles, as is demonstrated in more detail below. The systems are imaging because they separately measure the fluorescent emissions from multiple different locations in a two dimensional array of positions. The emissions from different locations are separated on the image because the emissions exit the Tamm structure at small angles close to normal (perpendicular to the layers of the Tamm structure). No lens or collimator is required because the Tamm structure itself sets the angles of the emissions based on the optical frequencies, and the emission angles are insensitive to the angle of incident excitation light.

FIG. 4B is a block diagram of an example multiplex fluorescence imaging system 430, according to one embodiment. The system includes a scanning light source 411, a two dimensional (2D) functionalized Tamm structure 471, and a detector array. The scanning light source 411 can scan by linear displacement in one or two dimensions, or by rotating in one or two dimensions, or using an optical coupler that steps or rotates in one or two dimensions, or some combination. Because the angle of excitation does not affect the angles of emission, the rotating light source is a useful option. In some embodiments, a light source simultaneously illuminates the entire area of the Tamm structure 471 and a scanning light source 411 can be replaced by such a light source.

The 2D functionalized Tamm structure 471 is a 1D Tamm structure (which layering in only one direction) on which the functionalization on the surface of the Tamm structure varies in two dimensions, such as in a microarray of affixed probe molecules used in some bio-sensing assays. In the illustrated embodiment, showing one cross section of the Tamm structure, walls 472 separate wells 474 on the functionalized surface of the Tamm structure. In some embodiments, the functionalizations in several wells are the same, but different samples 492 are contacted in different wells. In some embodiments, the functionalization is different in different wells, and the same sample 492 is contacted in several wells to test for several analytes. In some embodiments a combination of different functionalizations and different samples 492 are used to cover the area of the Tamm structure. It is assumed for purposes of illustration that the functionalization is the same in all wells 474, and that different samples 492 are tested in different wells. The 2D functionalized Tamm structure 471 provides for the imaging applications of the system 430.

For multiplexing, it is further assumed that each sample from a subject is mixed with a reagent that includes three different detection molecules, with different fluorophores for different analytes, For purposes of illustration, it is assumed that three different detection molecules are used with fluorophores that emit at three different optical frequencies.

FIG. 4B depicts a system 430 that illuminates the samples in wells 474 with RK (free space) excitation light 462. The TSCE at the target frequency of the Tamm structure, e.g., emitted by a first of the three fluorophores, exits the Tamm structure 471 as a ray 463a in the normal direction (angle 0°) represented by a single-dot-dash arrow. The TSCE at a different optical frequency (e.g., a higher optical frequency with a shorter wavelength), e.g., emitted by a second of the three fluorophores, exits the Tamm structure 471 as a ray 463b at a small angle (e.g., about 10°) represented by a double-dot-dash arrow. The TSCE at a third optical frequency (e.g., an even higher optical frequency with an even shorter wavelength), e.g., emitted by a third of the three fluorophores, exits the Tamm structure 471 as a ray 463c at a different small angle (e.g., about 20°) represented by a short-dash arrow. Only the coupled (KR) emissions are depicted to avoid cluttering the diagram. It is noted that similar rays at the same angles relative to normal exit the structure 471 in the upward RK (free space) direction.

In FIG. 4B a single detector array 456, such as a charge coupled device (CCD), is configured to detect the intensity of each of the rays 463a, 463b, 463c from each of the wells 474 in one or more pixel sensing elements of the array. Each well may appear in an image constructed form the signals at the detector array as a central portion at the target optical frequency surrounded by successive rings at the other optical frequencies. In some embodiments, the pixels are shaped, or numerically summed, to integrate the intensity in each ring.

In some embodiments, only one polarization is of interest, such as S polarized light to distinguish the TSCE from the SPCE that is P polarized as described below. In such embodiments, a polarizer is included in the optical path between the Tamm structure 471 and the detector, e.g., in optical coupler 112b of FIG. 4A. In some embodiments, a filter is also included in the optical coupler 112b to filter out the excitation light 462. In the illustrated embodiment, the optical coupler 112b includes filter/polarizer 416. In some embodiments, only polarized light is desired to excite the fluorophores and a polarizer 414 is included in the optical path from light source to 2D functionalized Tamm structure 471, such as in optical coupler 112a depicted in FIG. 4A.

FIG. 4C depicts a system 431 that illuminates the samples in wells 474 with KR (coupled) excitation light 462. In addition, FIG. 4C depicts a second detector array 457 to detect the free space (RK) emissions also. The scanning light source 411, 2D functionalized Tamm structure 471, detector 456, and rays 463a, 463b, 463c are as described above. However, in this embodiment, the scanning light source 411 is configured to excite the fluorophores in the coupled mode through the Tamm structure 471, that is, with coupled or KR excitation light. Here a polarizer/filter 417 is placed so as not to fall in the path between the light source 411 and the Tamm structure 471. In addition another filter/polarizer 415 is placed between the Tamm structure 471 and the second detector array 457 to select TSCE and to block scattered excitation light 462. In some embodiments, a polarizer (not shown) is included in the optical path between the light source and the Tamm structure 471.

1.5 Tamm Structure Fluorescence Measurement Method

Figure 5A:
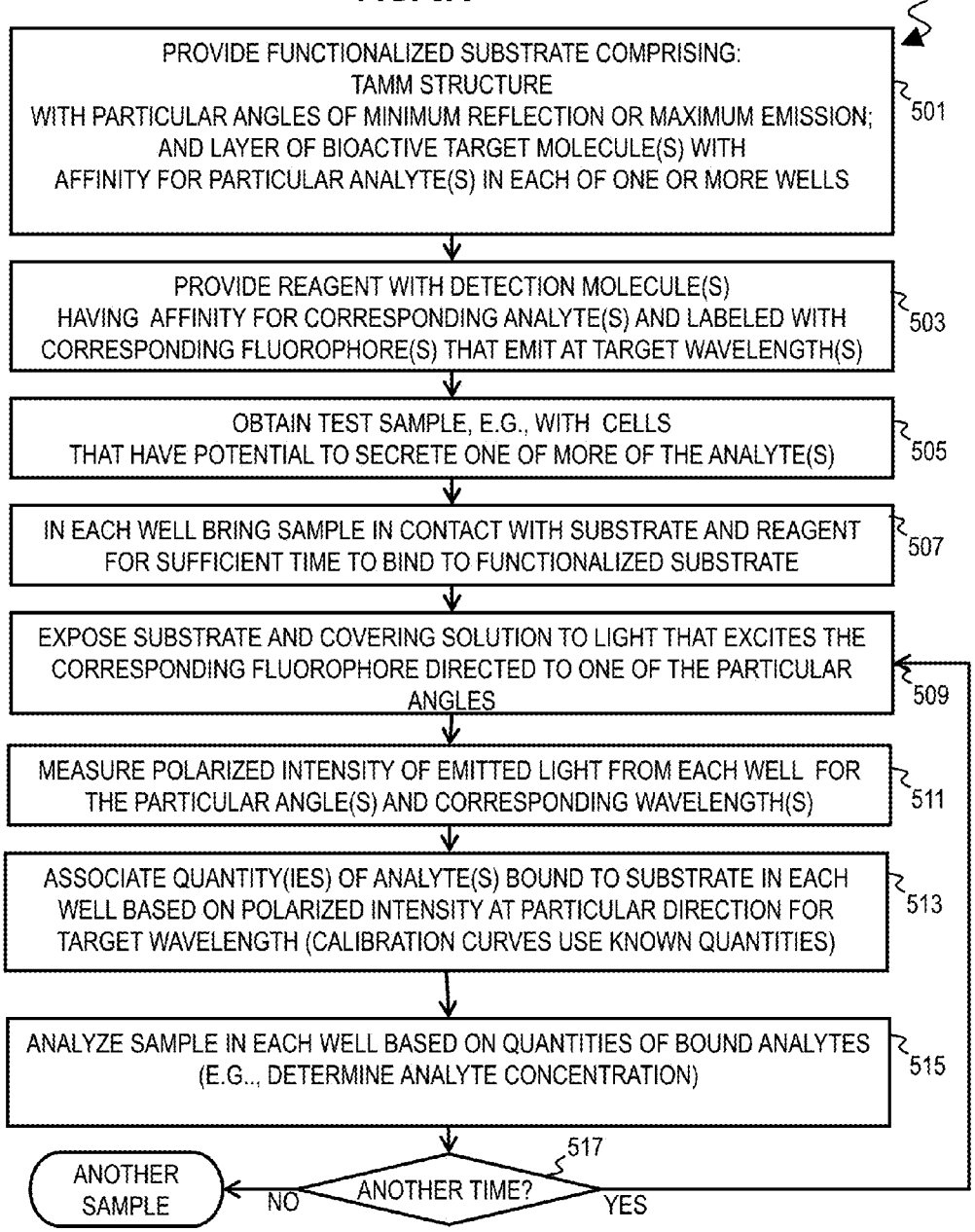

FIG. 5A and FIG. 5B are flow charts that illustrate an example method 500 to perform an enhanced fluorescence assay using a Tamm structure, according to an embodiment. Although steps are depicted in FIG. 5A and FIG. 5B as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

In step 501, a functionalized substrate is provided. In an illustrated embodiment, the functionalized substrate includes a Tamm structure configured to couple with a target optical frequency to be used in an assay. The Tamm structure includes a metal film deposited on multiple dielectric layers including multiple high index of refraction layers alternating with multiple low index of refraction layers. The thickness of each layer is about a quarter of a wavelength of the target optical frequency in the layer. In some embodiments, the thickness of each layer is about three quarters of a wavelength of the target optical frequency in the layer. As a result, the Tamm structure has particular angles of minimum reflection or maximum emission for each of one or more optical frequencies near the target optical frequency. In this embodiment, the functionalized substrate also includes a layer of one or more populations of substantively identical bioactive target molecules that bind to a particular analyte of interest for corresponding one or more analytes of interest. The functionalized substrate can be provided in any manner. In some embodiments the functionalized substrate is provided as depicted in FIG. 5B and described below.

In step 503, a reagent is provided, typically in solution. The solution of reagent includes a known quantity of a detection molecule comprising a probe and a fluorophore. The probe is selected to assay for the particular analyte. The probe is labeled with a particular fluorophore from the particular set of fluorophores with emission wavelengths suitable for Tamm structure interactions. The reagent can be provided in any manner. For example, in some embodiments, the reagent is obtained from a commercial supplier. In some embodiments, the reagent is provided in an assay kit that also includes the Tamm structure and the bioactive molecule in a separate container. In some embodiments the reagent is prepared locally by a user of the assay. In some embodiments, the reagent includes known concentrations of each of several different detection molecules, each with corresponding different fluorophores and each with affinities for corresponding different analytes, e.g., different cytokines secreted from a single cell.

Any molecule may be included as the probe in the detection molecule, such as a polymer, a ligand, an antigen, an antibody, a protein, an oligomer, a protein, a peptide, DNA, RNA or an oligonucleotide. Any fluorophore may be included in the detection molecule, such as fluoresceins, eosin, coumarines, rhodamines, cyanines, benzophenoxazines, phycobiliproteins or fluorescent proteins.

In step 505 a test sample is obtained with a quantity of a particular one or more analytes to be determined by the assay. During a calibration phase used in some embodiments, step 505 includes providing a control sample with known quantities of the one or more particular analytes. For assays that are previously developed, with a known calibration curve, a control sample is not used during step 505. The quantity (such as the presence or concentration) of each of the one or more analytes in the test sample is determined during step 515, described below. Any material may serve as one of the one or more analytes, such as a polymer, a ligand, an antigen, an antibody, a protein, a cytokine, a peptide, DNA, RNA, oligonucleotide, a virus, bacterium, or a cell from a patient.

In step 507, the functionalized substrate is contacted with the test sample and the reagent for sufficient time to produce binding of the one or more different detection molecules to the one or more different analytes or to produce binding of the one or more different analytes to the one or more different fixed bioactive target molecules. To monitor temporal progression of a cell-oriented process, steady state conditions do not need to be reached.

In step 509, the substrate and covering solution resulting from step 615 are exposed to excitation light that excites fluorescence in the one or more particular fluorophores corresponding to the different analytes.

In step 511 the relative intensity of emission electromagnetic waves is measured at the emission wavelength of the fluorophore corresponding to each of the one or more analytes. In some embodiments, the measurement of intensity or polarized intensity or direction or some combination is made relative to a reference, such as a reflected amount or an amount at a particular angle not associated with an emission maximums, or an angle of minimum intensity. In the illustrated embodiment, step 511 overlaps in time step 509, as the substrate and covering solution are excited and fluoresce measured at the same or overlapping times.

In step 513, a particular quantity of analyte bound to one or more areas on the functionalized substrate is associated with the measured value of relative intensity or polarization or direction or some combination. During a calibration phase, the known quantity of analyte in the control sample is associated with the measured values to add points to the calibration curves.

In step 515, one or more analyses of the sample are performed based on the quantities of the bound analytes. For example, one or more functions of an immune system cell are determined by a profile of cytokines secreted during measurement. As another example, a rate of secretion of the analyte by cell is determined based on a difference with a prior or subsequent measurement. In some embodiments, step 515 includes exposing the sample to one or more stimulants, e.g., to induce an immune reaction in a sample that includes one or more cells of an immune system.

In step 517, it is determined whether to make a measurement of the same sample at another time. If so, then control passes back to step 509 to expose the sample again to excitation electromagnetic waves. If not, then another sample, if any, is measured on another substrate, e.g., by returning to step 501 or step 505. In some embodiments, the next measurement is with another known quantity of analyte in another control sample to produce another point for the calibration curve. In a post calibration operational phase, a quantity on the established calibration curve associated with the measured intensity or polarization or direction, or some combination, is determined to be the quantity of the analyte in the test sample. The quantity indicates, for example, the presence, absence or concentration of the analyte.

In FIG. 5B a method 550 is depicted for providing a functionalized substrate. Thus method 550 is one embodiment of step 501. In step 551, it is determined which target optical frequency (and associated wavelength in air) is to be used for fluorescent detection or quantification of one or more analytes in a detector, an assay or imaging system. This information is used to determine which Tamm structures are suitable for use.

In step 553 a Tamm structure is obtained to pass target optical frequency (and associated wavelength in air) in the normal direction (perpendicular to the layers of the Tamm structure, e.g., at 0 degrees). In some embodiments, the substrate is obtained (e.g., from a commercial supplier) with both the Tamm structure and layer of bioactive molecule. In some embodiments, the substrate is obtained with the Tamm structure but without the bioactive layer, and the bioactive layer is deposited during step 561. In some of these embodiments the bioactive molecule is supplied and shipped in a separate container (e.g., to preserve its efficacy) as part of an assay kit, and deposited during step 561 to form the functionalized substrate when desired for use.

In some embodiments, step 553 includes step 555 for simulating the optical frequency and angular response of multiple trial Tamm structure designs using one of the electric field modeling packages available. For example, in the embodiments described below, simulations of transmission and reflectance spectra were performed using several software packages, based on the transfer matrix method, all of which yielded nearly identical results. These packages are BR Project from the Institute of Electronic Materials Technology (Warsaw, Poland) and TFCalc from Software Spectra. As an initial configuration a layer thickness is set to about one quarter to about three quarters of the wavelength of the target optical frequency in the layer, and about ten layers are used to have enough to set up the Tamm modes without having too many which can lead to excessive attenuation of the emitted light.

In some embodiments, step 553 includes step 557 for fabricating the best Tamm structure design determined in step 555. Suitable materials include: silver (purity 99.999%), polyvinyl alcohol (PVA, MW 13,000-23,000), sulforhodamine 101 (S101), rhodamine B (RhB), rhodamine 6G (Rh6G), and fluorescein (FL) were purchased from Sigma-Aldrich of St. Louis, Mo. Glass microscope slides were obtained from VWR of Radnor, Pa. Nanopure deionized water was used for all solution preparations. For example, in some of the embodiments described below a Bragg grating (BG) was made by plasma-enhanced chemical vapor deposition (PECVD) of $SiO_2$ and $Si_3N_4$ on standard microscope slides. Prior to PECVD of the Tamm substrates, the glass slides were cleaned with piranha solution and then with nanopure deionized water and dried with an air stream. This structure consisted of alternating layers of $SiO_2$, with a low (L) refractive index, and $Si_3N_4$, as the high (H) refractive index dielectric. Other embodiments use other dielectrics including tantalum pentaoxide and other appropriate dielectrics suitable for different wavelengths regions of interest, such as the ultraviolet (UV) region of the optical spectrum. Dielectrics with suitable optical parameters are already known. The refractive index of $Si_3N_4$ can be adjusted by the relative amounts of silane and ammonia during deposition. Low-loss dielectric materials provides high-quality factors for resonances, which are expected to provide selective excitation of surface-bound species. The top layer can be silica or alumina, which provides well-known surface chemistry and easy conjugation of biomolecules. These structures do not require top-down nanofabrication methods and can be produced using only vapor deposition. The fabrication of Bragg gratings have also been reported using other methods such as layer-by-layer assembly and spin-coating methods. In the example embodiment described below, the low (L) refractive index dielectric thickness, and the high (H) refractive index dielectric thickness were 55 nm and 105 nm, respectively. The sequence of layers was six cycles of (HL), with an additional 55-nm-thick H layer of $Si_3N_4$ as the top dielectric. Tamm structures typically use the high dielectric constant material for the top dielectric layer.

To form the Tamm structure, the Bragg grating was coated with a 42-nm-thick layer of silver by sputtering or vapor deposition. An Edwards Auto 306 vacuum evaporation chamber was used under high vacuum ($<5\times10^7$ Torr) for the deposition of the silver layer. The deposition rate (~1.0 nm/min) was adjusted by the filament current, and the thickness of the deposited film was measured with a built-in quartz crystal microbalance.

In some embodiments, step 557 include making measurements of the actual layer thicknesses and optical properties and simulating the optical frequency and angular dependence based on the actual layer properties. For example, The actual thickness and optical constants are determined using an N and K model 1200 ellipsometer.

In step 561, a functionalized substrate is provided by depositing on the Tamm structure a layer of one or more different bioactive target molecules with affinity for a particular set of one or more analytes, respectively. Some embodiments include step 563 to mount the functionalized substrate on a glass prism. In the example embodiments, a sample was emulated by coating the Tamm structure with 45 nm of PVA, which contained approximately 1 µM fluorophore. The solution was 1% PVA (MW=16,000-23,000) in water, 3000 rpm, for 1 min, which yielded a thickness of 45 nm. A dielectric spacer was not used between the fluorophore in PVA and the metal surface. Four fluorophores were utilized in the experimental embodiments described below.

To determine the actual optical frequency and angular properties of the fabricated functionalized substrate, steps 565 through 575 are included in some embodiments. In step 565 it is determined whether testing will be done based on emissions from a fluorophore at the target optical frequency. If so, then in step 575 incident angles that produce maximum measured emission intensity at the target optical frequency are determined, as are the angles where the maximum emission is detected. In some embodiments, if these angles differ from the simulated values, one or more parameters of the simulations are adjusted during step 575 to achieve agreement. For example, absorption by one or more layers, modeled as an imaginary part of the index of refraction, is changed to give agreement with the actual angles and intensity of fluorescent emissions. Control then passes to step 581.

If it is determined in step 565 that testing will be not be done based on emissions from a fluorophore at the target optical frequency, then in step 571 incident angles of minimum measured reflection intensity at the target optical frequency are determined as a surrogate for angles of expected maximum emission. In some embodiments, if these angles differ from the simulated values, one or more parameters of the simulations are adjusted during step 571 to achieve agreement. Control then passes to step 581. This is done because light that couples with a Tamm state is expected to cause decreases in reflectivity at certain angles and optical frequencies associated with that state. Those can be discovered by reflectivity measurements, or by absorption measurements as a surrogate for reflection measurements (high absorption for transmitted light associated with high reflectance of the incident light).

In step 581, the particular angles of measured emission maximums, or measured reflection minimum or simulated emission maximum are provided for setting up the predetermined angles of measurement during sensing, assaying or imaging experiments. In some embodiments, step 581 includes simulations to associate one or more angles with modes of Tamm structure interaction, such as TSCE or SPCE.

These Tamm structure functionalized substrates eliminate the need for expensive nanoscale fabrication, provides large surface area to work with, which is suitable for various assay formats, and can be mass-produced at minimum cost. Additional benefits include: the fluorescence emission from different dyes can be conveniently tuned by changing the substrate parameters in a simple and straightforward manner. These substrates can be adapted for multiple uses such as fluorescence studies in multicolor directional fluorescence imaging and/or sensing of multiple probes or for molecule-specific bio-sensing, with a high degree of spatial control over the fluorescence emission. The layer numbers and thicknesses can be modified according to the desired target optical frequency. Tamm structures can become widely used in the biosciences, particularly for high-throughput testing and clinical applications. These uses will be facilitated by the favorable structural and optical properties of Tamm structures.

2. Example Embodiments

Here are described 1DPC substrates that provide fluorescence amplification for surface bound fluorophores within a wavelength of the 1DPC at fixed angles independent of angle of incident excitation light.

Figure 6A:
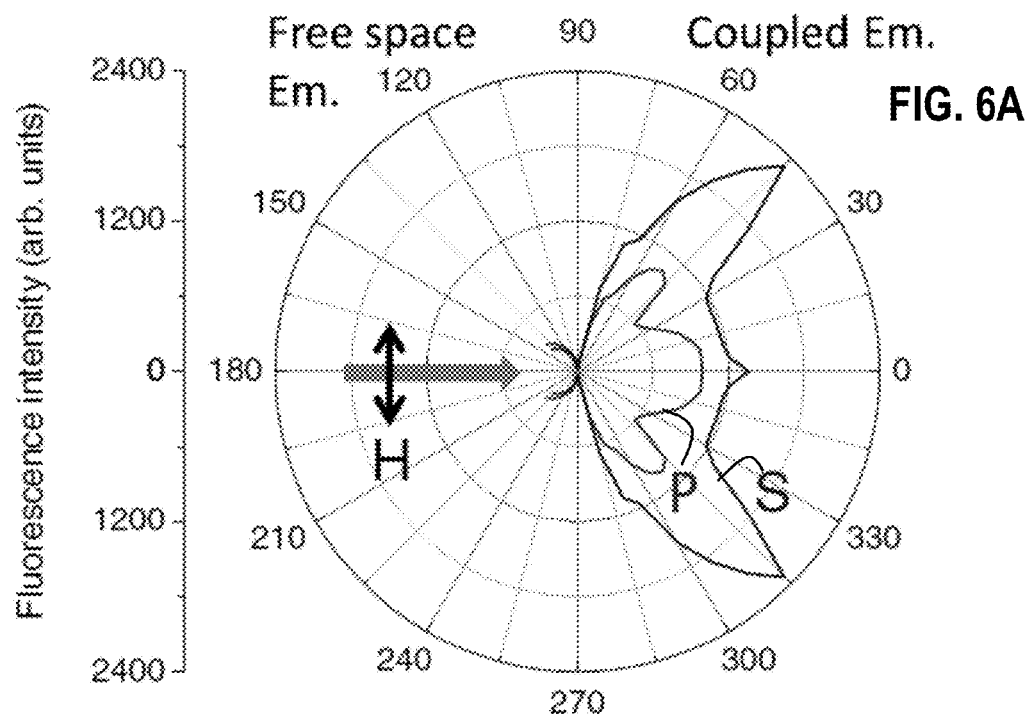
FIG. 6A and FIG. 6B are graphs that illustrate angle and wavelength dependence of fluorescence intensity in control experiments without a Tamm structure.
Figure 6B:
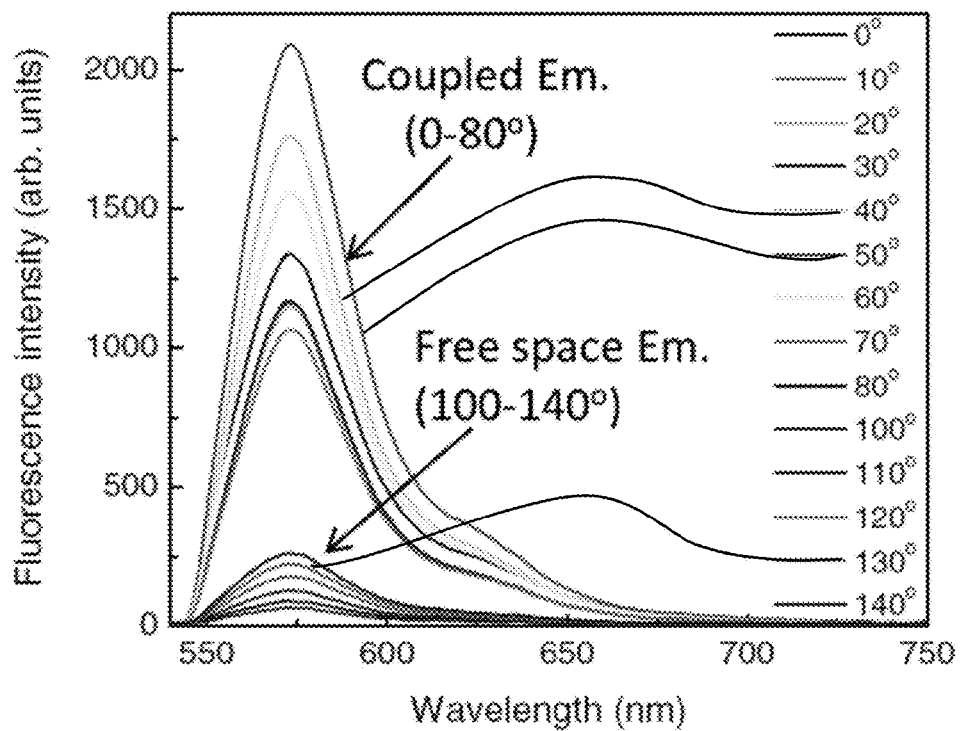

For comparison, a control device was also fabricated using the same fluorescent layer on glass instead of on a Bragg grating. A glass slide was functionalized by subsequently coating with rhodamine B (RhB)-doped polyvinyl alcohol (PVA) in water, 1% PVA (MW=16,000-23,000), 3000 rpm, for 1 min, which yielded a thickness of 45 nm. FIG. 6A and FIG. 6B are graphs that illustrate angle and wavelength dependence of fluorescence intensity in control experiments without a 1DPC. FIG. 6A is a polar graph that illustrates example measured fluorescence intensity as a function of measured angle for illumination by horizontally polarized incident light incident from direction 180 degrees.

The radial distance from the center of the graph indicates the amount of fluorescence according to the scale to the left in arbitrary units. Note that the scale maximum is 2400 units. The emission occurs over a wide range of angles. As expected, the majority of the emission occurs into the slide (coupled emission) due to its higher refractive index than air. FIG. 6B is a graph that illustrates example dependence of fluorescence intensity on optical frequency (expressed as wavelength in air). The horizontal axis indicates wavelength in nanometers, and the vertical axis indicates fluorescence intensity in arbitrary units, with a maximum over 2000. Multiple traces correspond to angles in ten degree increments for coupled emission (0 to 80 degrees) and free space emission (100 to 140 degrees). Consistent with FIG. 6A, the majority of the emission occurs as coupled emissions. No shifts in the emission spectra were observed for any observation angle. In contrast to the results shown below for the 1DPC, it was found that the RhB emission on the glass slide is only partially polarized. The trace for 50 degrees in FIG. 6B shows the maximum intensity, and has a spectral shape that closely represents the emission spectrum of the RhB fluorophore, which is useful for comparison to spectrally filtered emissions described in some embodiments below.

Figure 6C:
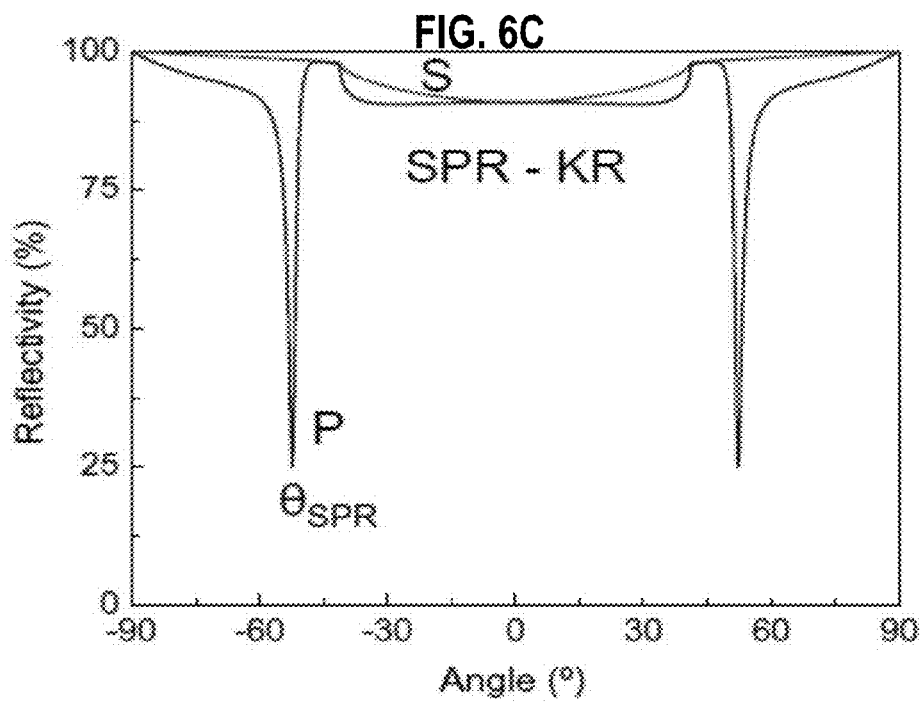
FIG. 6C and FIG. 6D are graphs that illustrate angle and wavelength dependence of fluorescence intensity in plasmon experiments without a Tamm structure.
Figure 6D:
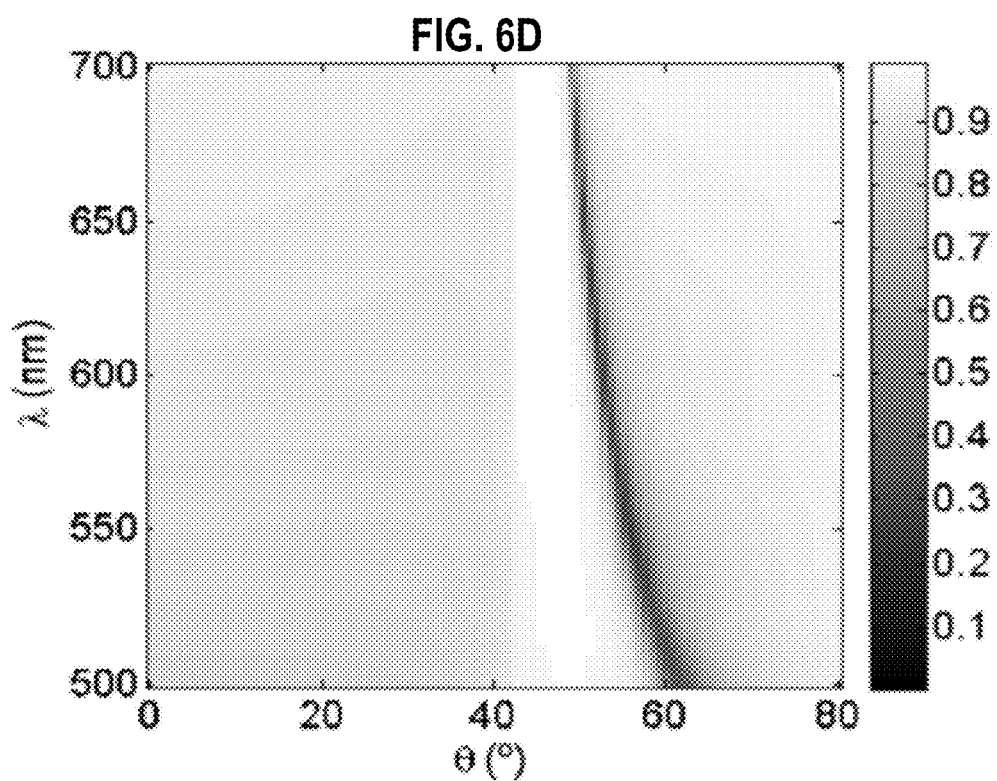

The unique properties of a Tamm state can be seen by comparison with the more familiar properties of surface plasmon resonance (SPR) structure. An SPR structure was constructed of a thin metal film, 42 nm thick, on a glass prism. A top layer of 45-nm-thick PVA is added to be consistent with the experiments using the Tamm structure, described below. The optical properties of the SPR structure are relatively easy to understand. FIG. 6C and FIG. 6D are graphs that illustrate angle and wavelength dependence of fluorescence intensity in plasmon experiments without a Tamm structure. FIG. 6C is a graph that illustrates an example angle-dependent reflectivity at a single wavelength (about 570 nm in air) for KR illumination. In FIG. 6C, the horizontal axis indicates angle of incidence in degrees; and, the vertical axis indicates reflectivity in percent. The S polarized reflectivity is high at all angles; however, the P polarized reflectivity dips deeply at about +/−57°. FIG. 6D is a dispersion graph that illustrates an example angle-dependent reflectivity in the optical wavelength band. The horizontal axis indicates angle of incidence in degrees, the vertical axis indicates wavelength in air in nanometers. The brightness at a point on the graph indicates the reflectivity, with white indicating 100% reflectivity and black indicating 0% reflectivity. FIG. 6C is equivalent to a horizontal line across FIG. 6D at 570 nm.

Surface plasmons cannot be coupled by light incident from the air side (RK illumination). The reflectivity is high at all angles of incidence from the air side for both S and P polarized light. Strong dips in the reflectivity can be seen with KR illumination through the prism, but only with P-polarized light. This is because surface plasmons are P polarized. The dips in reflectivity occur at the surface plasmon angle ($\theta_{SPT}$). Only one dispersion plot is needed for the SPR structure, which is for P polarized KR illumination. There is a single band of decreased reflectivity that shifts slightly with wavelength due to changes in the optical constants.

FIG. 7 is a block diagram that illustrates an example Tamm structure, according to an embodiment. This Bragg grating includes 7 H layers of 55 nm thickness, and 6 L layers of 105 nm thickness, with the top layer a H layer. the metal film is 42 nm of silver. These properties were computed to give a wavelength of 570 nm for the target optical frequency. The Tamm structure was functionalized by subsequently coating with rhodamine B (RhB)-doped polyvinyl alcohol (PVA) in water, 1% PVA (MW=16,000-23,000), 3000 rpm, for 1 min, which yielded a thickness of 45 nm.

FIG. 8A through FIG. 8D are dispersion graphs that illustrate example Tamm structure coupled modes (Tamm states) where computed reflectivity is a minimum for different incident angles and polarizations, according to various embodiments. An insert on each figure indicates the side of incidence (KR or RK), and the polarization (TE equivalent to S polarization, and TM equivalent to P polarization). On each dispersion graph, the Tamm states appear as a dark band near 570 nm wavelength (the wavenumber in air of the target optical frequency) at 0° that shifts to shorter wavelengths at higher angles up to about 30°. Some other states are evident as other lighter bands at higher wavelengths and angles in FIG. 8A through FIG. 8C. For P polarized KR incidence depicted in FIG. 8D, the SPR is evident as a second very dark band near 60° with a slight dependence on wavelength.

Figure 8A:
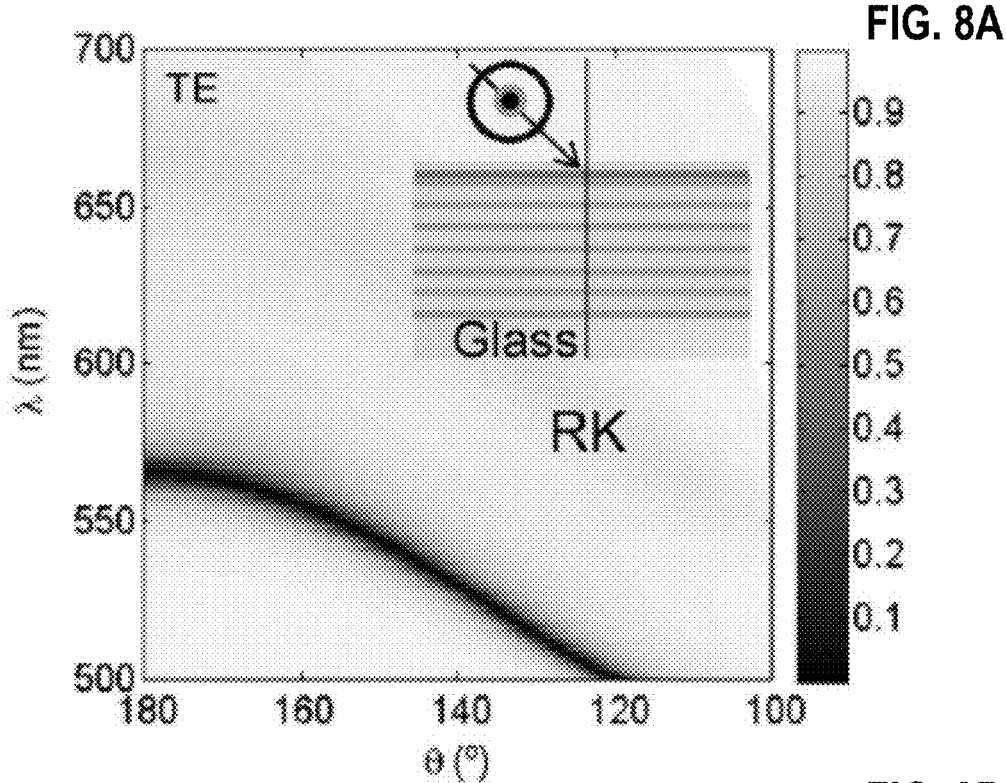
FIG. 8A through FIG. 8D are dispersion graphs that illustrate example Tamm structure coupled modes where computed reflectivity is a minimum for different incident angles and polarizations, according to various embodiments.
Figure 8B:
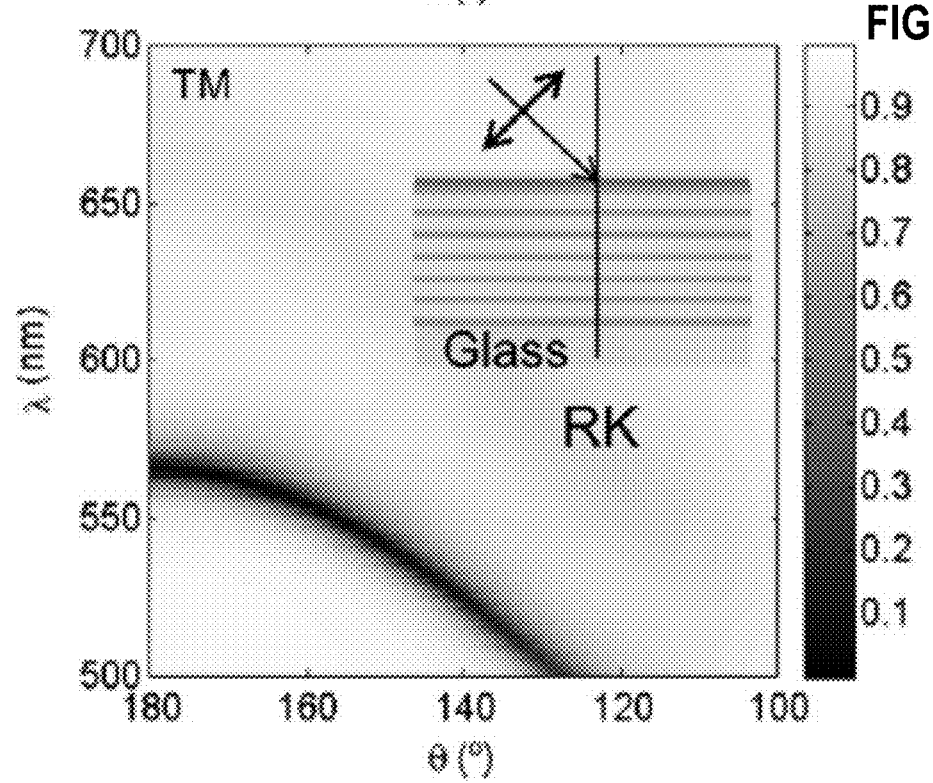
Figure 8C:
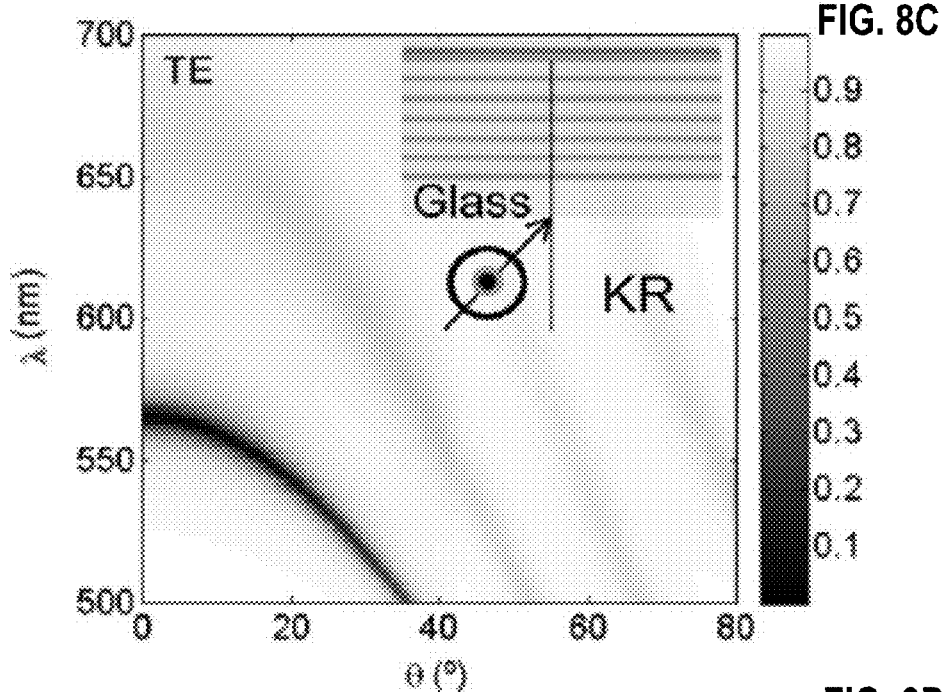
Figure 8D:
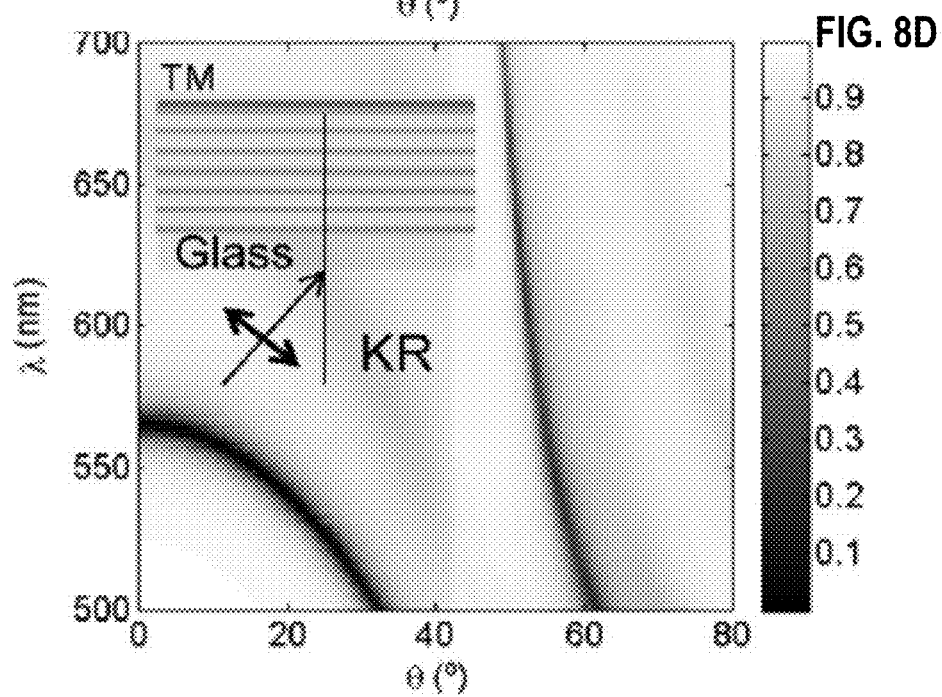
Figure 9A:
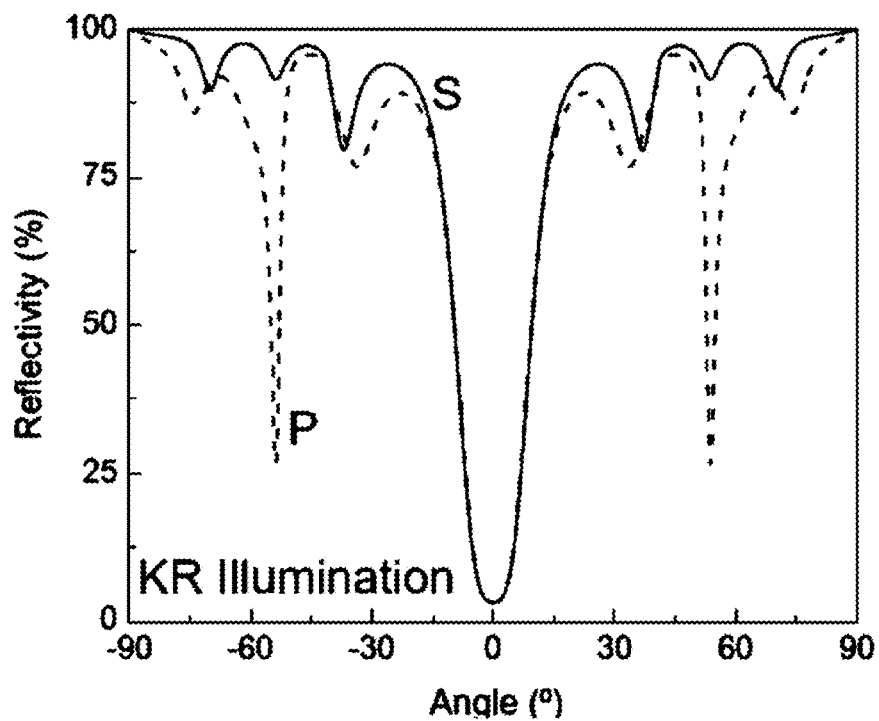
FIG. 9A and FIG. 9B are graphs that illustrate example computed reflectivity dependence on angle, according to various embodiments.
Figure 9B:
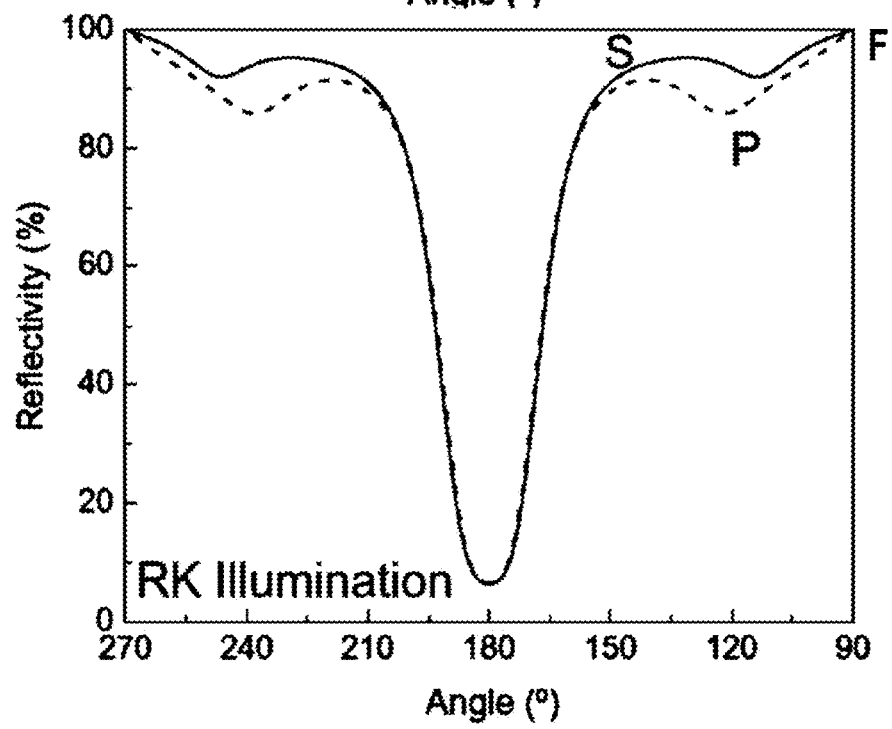

FIG. 9A and FIG. 9B are graphs that illustrate example computed reflectivity dependence on angle, according to various embodiments. These depict particular slices from the dispersion plots in FIG. 8A through 8D. In both, the horizontal axis is angle in degrees; and, the vertical axis is computed reflectivity in percent. FIG. 9A shows for KR illumination a slice at 569 nm for S polarized light (from FIG. 8C) as a solid line and for P polarized light (from FIG. 8D) as a dashed line. FIG. 9B shows for RK illumination a slice at 569 nm for S polarized light (from FIG. 8A) as a solid line and for P polarized light (from FIG. 8B) as a dashed line. The wavelength 569 was chosen because it matches the emission maximum of RhB. The simulations are for the emission maximum, and not the excitation wavelength, because SPCE-like behavior is expected, where the resonance caused drops in reflectivity coincide with the angular distribution of the coupled emission.

In contrast to SPR (FIG. 6C), the Tamm structure displays dips in reflectivity with both KR and RK illuminations. In addition, the reflectivity is near zero at either 0° or 180° incidence, and the drop in reflectivity is seen for both P polarized and S-polarized emissions. The Tamm structure also shows the usual SPRs at 54° with P-polarized KR illumination (FIG. 9A dashed line). These simulations suggest that TSCE may occur perpendicular to the sample plane (near 0° or 180°) and in either the KR or RK direction. In future experiments, the emission could be restricted to the KR direction because it is known that Tamm states can exist even if the halfspace above the BG is completely filled with metal. Excitation and emission perpendicular to the surface is convenient for multiwall plates and protein or DNA array applications, a sutilized in FIG. 4B and FIG. 4C.

FIG. 10A and FIG. 10B are graphs that illustrate example computed electric field intensity dependence on position within a Tamm structure, according to various embodiments. In each, the horizontal axis is distance in nm and the vertical axis is electric field intensity $|E^2|$ relative to intensity without the Tamm structure (dimensionless). FIG. 10 shows KR illumination from the glass side, while FIG. 10B is RK illuminated in the opposite direction from the air side. The graphs are reversed so that the incident light is from the left in both graphs. The 14 layers (one metal and 13 dielectric layers) are also indicated along the horizontal axis of each graph. Incident light is normal to the layers in each case and electric field intensity is computed for the emission wavelength of 569 nm as in FIG. 8A through FIG. 9B.

FIG. 10A and FIG. 10B depict another unique feature of a Tamm state, the location of the optical modes or light-induced fields. For an SPR structure, the field is located at the metal-sample interface on the side distal from the prism. The presence of this evanescent field in the sample allows SPCE to occur. In contrast to an SPR field, the Tamm field is located below the metal film and within the BG region of the sample, as depicted in FIG. 10A and FIG. 10B. The Tamm fields have similar intensities and are in the same location for KR or RK illumination. Tamm states are often described as surface-trapped states, which gives the impression that they are localized precisely at the BG-metal interface. However, this is not the case. For the example embodiment, the Tamm fields are most intense in the top high dielectric layer and, more specifically, closer to the next low dielectric layer. The Tamm fields occur throughout the Tamm structure, which suggests a means for TSCE to occur at 0° down through the sample. Very little of the Tamm field exists on the sample side above the metal, which suggests that there will be weak coupling of fluorophores with the Tamm states. However, previous work showed that fluorophores could display coupling with surface plasmons even when freely propagating light at the same wavelength could not interact with the structures. It was speculated that because the magnitude of the electric field on the fluorophore side of the metal is greater than zero, excited state fluorophores could couple with optical Tamm states, which in turn could result in TSCE.

The preceding simulations suggest that Tamm states could provide emission normal to the sample plane, which is useful for array-based assays with physically separate locations for each analyte, as described above in FIG. 4B and FIG. 4C.

Figure 11A:
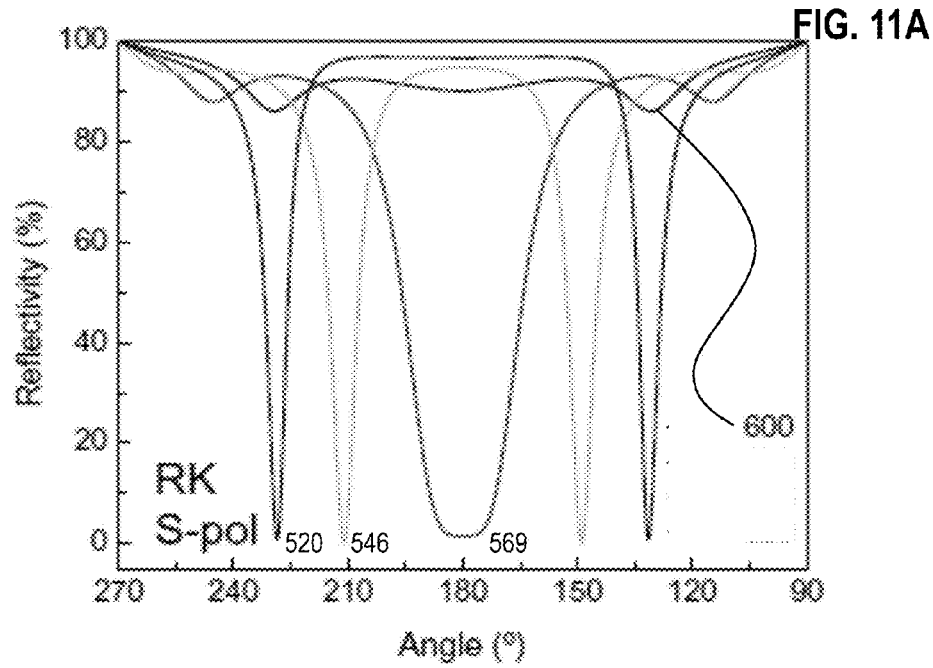
FIG. 11A and FIG. 11B are graphs that illustrate example simulated optical frequency separation by angle for S-polarized emissions (polarized parallel to layers of Tamm structure), according to various embodiments.
Figure 11B:
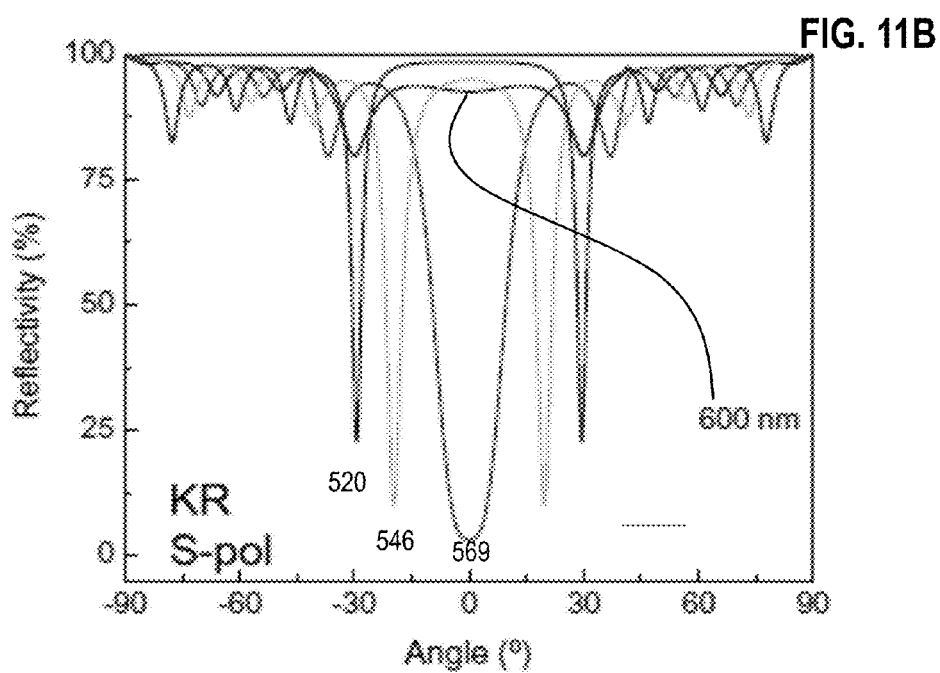

Multiplex assays can also be accomplished using multiple wavelengths. Therefore it was determined whether Tamm states could be used for wavelength separation. FIG. 11A and FIG. 11B are graphs that illustrate example simulated optical frequency separation by angle for S-polarized emissions (polarized parallel to layers of Tamm structure), according to various embodiments. In both plots, the horizontal axis indicates angle in degrees and the vertical axis indicates computed reflectivity in percent. Traces are shown for the wavelengths in air of the fluorescent emission from the four fluorophores at 520 nm, 546 nm, 569 nm and 600 nm, respectively, for S polarized light (similar results were obtained for P polarized light except for the additional P polarized SPR). FIG. 11A shows the results for RK illumination and FIG. 11B for KR illumination.

A reflectivity drop at 0° or 180° incidence is seen only for 569 nm, which was the target wavelength for a Tamm structure that is suitable for RhB. At the two shorter wavelengths (546 nm for Rh6G and 520 nm for FL), the resonances are found at off-axis angles for both KR and RK emission. Surprisingly, the reflectivity is not the same for KR and RK illuminations, and the angular shift is larger for the RK direction than for the KR direction. A Tamm resonance is not seen at 600 nm (SR101), which is consistent with the absence of a Tamm state at 600 nm in the full dispersion diagrams (FIG. 8A through FIG. 8D). The wavelength dispersion of the Tamm structure seen in FIG. 11A and FIG. 11B is larger than that found for the SPR structure (FIG. 6D). These simulations suggest that Tamm structures can provide the function of several separate optical components. The Tamm structure can collect the emission, beam the emission toward a detector with wavelengths separated by angle, and suppress longer wavelength emissions where a Tamm state does not exist. Thus this expected angular separation is utilized in the systems depicted in FIG. 4B and 4C.

Figure 12A:
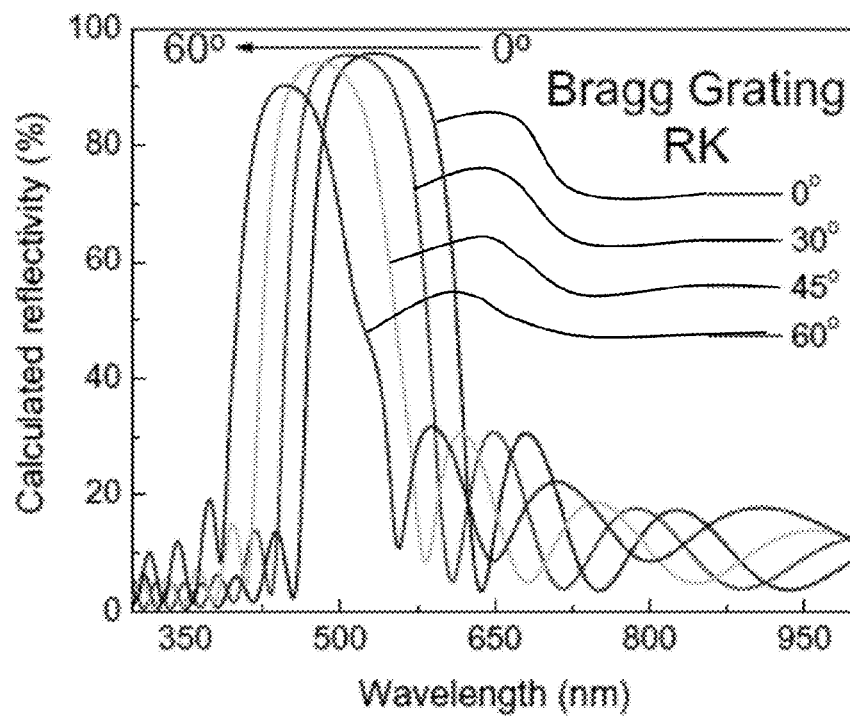
FIG. 12A and FIG. 12B are graphs that illustrate an example simulated frequency separation by angle in reflectance from a Bragg grating and a Tamm structure, respectively, according to an embodiment.
Figure 12B:
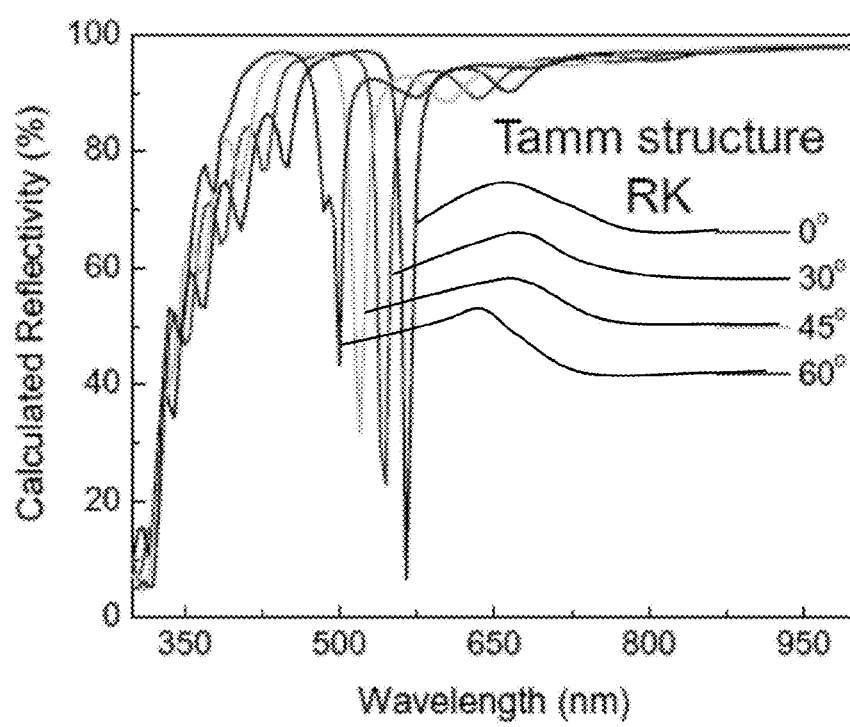

The optical properties of the Tamm structure depend on angle, wavelength, and polarization. It is difficult to measure all of these parameters. In contrast, it is simple to measure absorption or transmission. FIG. 12A and FIG. 12B are graphs that illustrate an example simulated frequency separation by angle in reflectance from a Bragg grating and a Tamm structure, respectively, according to an embodiment. For comparison with the experimental results, the calculated reflectivity spectra are shown for the BG (FIG. 12A) and the Tamm structure (FIG. 12B) with RK illumination. In both graphs the horizontal axis indicates wavelength in air in units of nanometers; and the vertical axis indicates calculated reflectivity in percent. Different traces are shown for 0°, 30°, 45° and 60° angles of incidence. Similar spectra were found for KR illumination.

The BG structure (FIG. 12A) shows a Photonic band gap (PBG) characterized by high reflectivity at 520 nm. This peak shifts to shorter wavelengths at higher angles of incidence. A remarkable change is seen upon the addition of the top silver layer (FIG. 12B). The wide PBG in the BG structure is replaced in the Tamm structure by a wider region of high reflectivity cut by a narrow resonance where the reflectivity dips greatly. These valleys also shift to shorter wavelengths at higher angles of incidence. This result shows that the addition of the silver film increases light transmission by the sample within the PBG and specifically at the Tamm resonance wavelength. A similar effect has been reported on multilayer metal-dielectric structures and described as plasmon-induced transparency. These resonances can be visualized in FIG. 8A through FIG. 8D by tracing a vertical line on those dispersion diagrams.

For experimental verification, four fluorophores were selected: S101 (600 nm), RhB (569 nm), Rh6G (546 nm), and FL (520 nm), where the number in parentheses indicates the wavelength in air of each emission maximum. As is seen below from the simulations and experimental results, the emission maxima of RhB, Rh6G, and FL are within wavelength range of the Tamm states of the experimental Tamm structure. The emission maximum of S101 is outside the wavelength range for the structure to support Tamm states. Angle-dependent fluorescence intensities and emission spectra were collected using the apparatus described in FIG. 4. Excitation was obtained from either a CW 532-nm Nd-YVO4 laser or a 472-nm CW laser diode. The emission was collected using a model SD2000 Ocean Optics spectrometer with a 1-mm-diameter optical fiber (NA 0.22) placed 2 cm from the sample. Polarizers were placed between the sample and fibers as found to be advantageous. For 532 nm excitation, a 550-nm longpass emission filter was used to remove scattered light. A 500-nm longpass filter is employed to reject the scatter from the 470-nm laser excitation. The intensity decays were collected using a TCPSC instrument (PicoQuant, Fluo-Time 100) by employing the pulsed laser diodes from PicoQuant (100 ps, 400 MHz) as the light source.

Figure 13A:
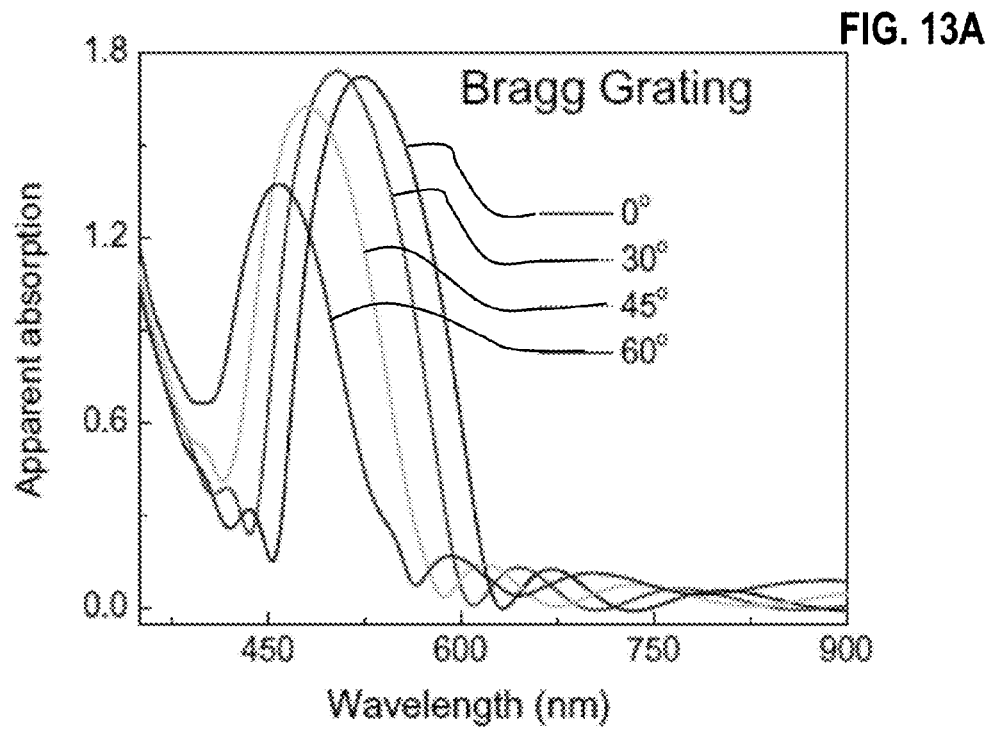
FIG. 13A and FIG. 13B are graphs that illustrate an example measured frequency separation by angle in apparent absorption through a Bragg grating and a Tamm structure, respectively, according to an embodiment.
Figure 13B:
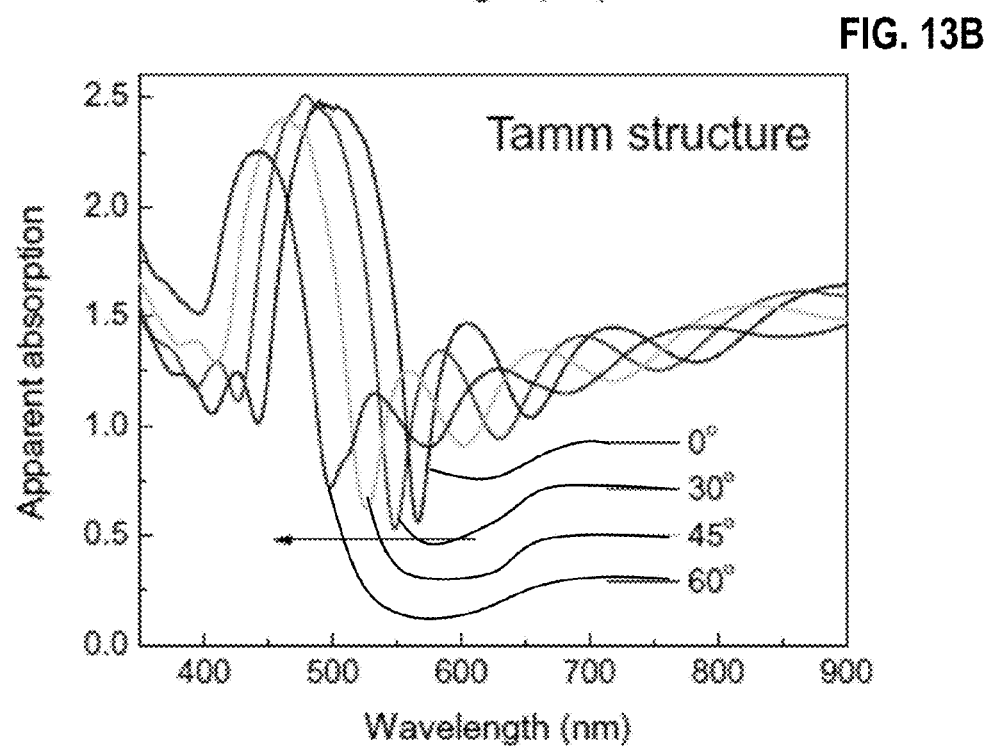

FIG. 13A and FIG. 13B are graphs that illustrate an example measured frequency separation by angle in apparent absorption through a Bragg grating and a Tamm structure, respectively, according to an embodiment. The term "apparent absorption" is used because the measurement does not separate absorption from reflection. In both graphs the horizontal axis indicates wavelength in air in units of nanometers; and the vertical axis indicates apparent absorption (the log of the ratio of incident intensity to transmitted intensity) which is dimensionless. Different traces are shown for 0°, 30°, 45° and 60° angles of incidence and RK illumination. Similar spectra were found for KR illumination.

Prior to the addition of metal, the BG structure (FIG. 13A) shows a PBG in good agreement with the simulated spectra shown in FIG. 12A. The addition of the metal layer resulted in increased transparency near 570 nm. As predicted by the simulations, in the Tamm structure (FIG. 13B) this absorption resonance (dip in absorption) shifts to shorter wavelengths at higher angles of incidence. We assign the dips from 500 to 570 nm to the Tamm states. These spectral shapes are similar to other reported Tamm state spectra. Color photographs (not shown) of the Tamm structure and a plain glass slide coated with 42 nm of silver demonstrate that the silver-coated slide is almost completely opaque at any angle of incidence, which agrees with the high reflectivity. When the same thickness of silver is placed on a BG, the Tamm structure becomes visibly transmissive. The transmitted light shifts from red to green with an increased observation angle, which is consistent with the shifts seen in FIG. 13B. Remarkably, combining two structures—a BG and a silver film, each with low transmission—results in increased transmission at specific wavelengths.

Subsequently, the Tamm structure was tested for coupling of fluorophores with the underlying Tamm state. The Tamm structure was spin-coated with 45 nm of PVA that contained RhB. Emission from the coated Tamm samples could be observed with either KR or RK illumination and different angles of incidence. Except for changes in intensity, similar results were obtained independent of mode of excitation. Using KR illumination at the SPR angle of incidence provided the highest intensities and allowed direct comparison with SPCE. In addition, this mode of excitation provides excitation for fluorophores close to the metal surface, which allows the observation of the fluorophores that are closest to the metal surface. This speculation is supported by the shorter decay times observed for KR excitation, but at this time a contribution of quenching at short distances from the metal cannot be ruled out.

Figure 14A:
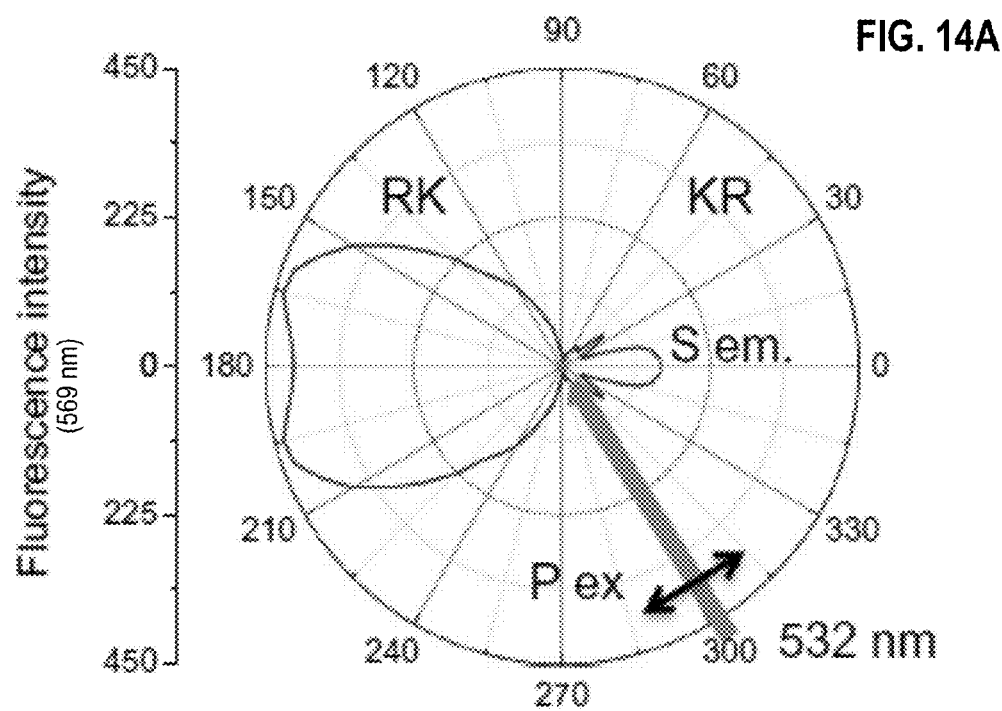
FIG. 14A through FIG. 14C are polar graphs that illustrate example angular dependence of fluorescence intensity for target optical frequency (wavelength in air 569 nm), higher optical frequency (wavelength in air 546 nm) with through-structure (KR) excitation, and the higher optical frequency (wavelength in air 546 nm) with normal free space (RK) excitation, respectively, according to various embodiments.
Figure 14B:
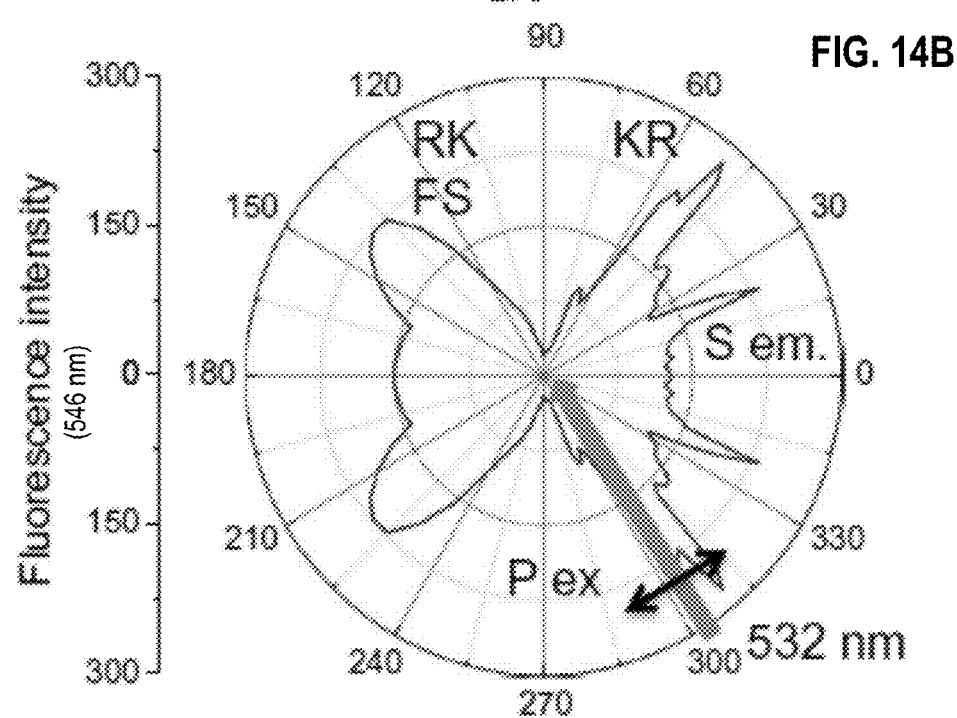
Figure 14C:
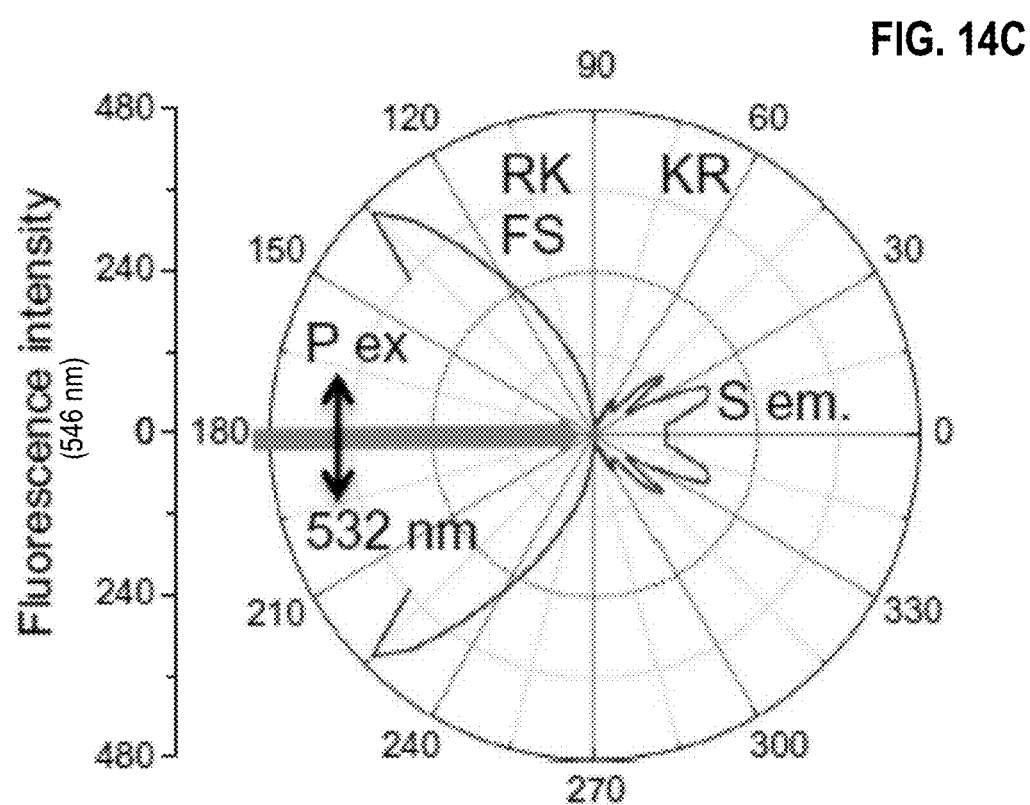

FIG. 14A through FIG. 14C are polar graphs that illustrate example angular dependence of fluorescence intensity for target optical frequency (wavelength in air 569 nm), higher optical frequency (wavelength in air 546 nm) with through-structure (KR) excitation, and the higher optical frequency (wavelength in air 546 nm) with normal free space (RK) excitation, respectively, according to various embodiments. Each plot is a polar graph that illustrates example measured fluorescence intensity as a function of measured angle for illumination by horizontally (P) polarized incident light incident from an indicated direction. Note that the scale maximum varies slightly among the plots from 300 to 480 in arbitrary units. FIG. 14A and FIG. 14B show results using KR illumination at the SPR angle of incidence, about −57° (303°) for the reasons given above: highest intensities, and comparison to known SPCE results.

As shown in FIG. 14A, the S-polarized TSCE occurs at a small range of angles near 0° with greater intensities on the free space side than the coupled side. Similar intensities were found for the P-polarized emission near 0°. The P polarized emission intensities were large near 48°. The angle and polarization of this emission indicates that this is due to coupling to the P polarized surface plasmons.

The P polarized SPCE intensity is much larger than the TSCE intensities. The origin of this difference can be attributed to the electric field intensities and their locations in the respective structures. The Tamm state electric field maxima are inside the structure and show weaker coupling efficiencies with the fluorophores positioned on top of the metal film. The SPRs have high electric field intensity on the metal surface and extend into the sample, resulting in more intense P polarized emission. In addition, as shown below, TSCE shows comparable emission intensities away from the structure (free space emission) and through the structure (coupled emission). In contrast to TSCE, the majority of the SPCE occurs through the structure, with much less free space emission. However, the TSCE in the KR direction still occurs with significant intensity. As is discussed below, it is believed that a significant fraction of the RK emission is also TSCE that is detected away from the top of the structure.

The emission spectra of the TSCE were measured at various angles close to 0°. The emission spectra display small shifts to shorter wavelengths as the observation angle is increased. Similar shifts and intensities were found for both the S polarized and P polarized emissions. The origin of the small spectral shifts and the similar S polarized and P polarized intensities can be understood from the dispersion plots in FIG. 8A through FIG. 8D. Both S polarized and P polarized resonances occur at 569 nm, and there are only small shifts in wavelengths for angles below 20°.

The expected results for the Tamm structure with Rh6G, which has a slightly shorter emission maximum of 546 nm, were also considered. Simulated data for this wavelength shifts the Tamm resonance from 0 to 19°. This result shows that the Tamm resonances are strongly dependent on wavelength, and the Tamm resonance is similar for both S polarization and P polarization. The P polarized reflectivity shows a decrease at 54° that is due to the usual surface plasmons. Even when the wavelength and angle are changed, the Tamm fields are still localized below the metal film in the uppermost dielectric layer. Similar field intensities are found for both S polarized and P polarized illuminations. With illumination at the SPR angle of 54°, S polarized emission does not couple to any specific mode, but a high field is obtained by P polarized light. The SPR field is approximately 5-fold larger than the Tamm field, a result found consistently for a number of wavelengths and angles. Referring back to FIG. 8A through FIG. 8D, it is seen that the Tamm resonances shift away from 0° at shorter wavelengths and only P polarized KR illumination creates surface plasmons.

FIG. 14B shows the angle-dependent emission intensities of Rh6G at 546 nm with KR illumination. For this wavelength, the TSCE direction is no longer perpendicular to the surface but rather occurs at approximately 20° from the normal. This is consistent with the angular shift calculated. FIG. 14B also shows a second peak approximately 47° from the normal. Because this emission is S polarized, it cannot be from coupling to surface plasmons. The origin of this peak can be seen from the dispersion plots in FIG. 8C. Consider a horizontal line starting at 546 nm across the panel. This line intersects the Tamm state at approximately 17° and also dips at 47° and at some larger angles. The intensity peak at 47° is attributed to this latter intersection point. It is noted that the intensity of the 47° peak is higher than that at 17°, but the resonance at 47° appears to be weaker in FIG. 8C.

FIG. 14C compares the Rh6G intensities with RK excitations. There appears to be higher free space emission with RK illumination as compared with KR illumination in FIG. 14B. It is believed that this occurs because RK illumination provides relatively uniform excitation through the PVA layer, whereas KR illumination excites fluorophores closer to the metal that are more strongly coupled to the Tamm state. It is also noticed that the angular distribution of the TSCE is slightly different for KR and RK illuminations. The simulations showed slightly different reflectance spectra for KR and RK incidence, but did not predict the TSCE to depend on the mode of excitation. One possible explanation is that KR excitation creates an excited state dipole population preferentially aligned normal to the surface, and RK illumination results in dipoles mostly parallel to the surfaces.

The emission spectra of Rh6G on the Tamm structures was examined for various angles of observation. The emission spectra were surprisingly complex, showing two main bands near 550 and 650 nm. Similar spectra were found for both S polarized and P polarized emissions, demonstrating that these spectra are for TSCE and not SPCE, which would be P polarized. These spectra can be understood from the dispersion plots in FIG. 8A through FIG. 8D. Consider a vertical line in FIG. 8C starting at 0°. This line intersects a Tamm state at approximately 570 nm and again at approximately 660 nm. These emission maxima are seen in the spectra recorded at 0°. Now consider a vertical line at a larger angle near 20°. The vertical line now intersects the resonances at shorter wavelengths, which are close to the observed emission maxima at this observation angle. The longer wavelength peaks in the emission spectra appear to be coupling the long wavelength side of the Rh6G emission to longer wavelength Tamm states. In contrast to SPCE, TSCE is expected to occur both away from the Tamm structure (RK) and through the Tamm structure (KR).

The emission spectra were examined as seen from the RK direction. These spectra display spectral shifts that depend on the observation angle. The spectral shifts are less dramatic than those seen with KR observation. Examination of the dispersion diagram with RK illumination (FIG. 8A and FIG. 8B) shows that there are fewer resonances for RK illumination than for KR illumination (FIG. 8C and FIG. 8D). Second, with RK illumination, a higher fraction of the emission is expected to be from Rh6G that is not coupled to the structure. The spectral shifts demonstrate that at least some of the RK emission is from coupling to the Tamm state. This suggestion is supported by the RK free space emission spectra of the three probes that overlap the Tamm state (RhB, Rh5G, and FL) and the absence of such spectral shifts for S101, which does not overlap the Tamm state.

It is informative to compare the angular intensity distribution for the four different probes. These distributions with KR illumination show that the angular distributions become wider when changing from RhB (569 nm) to Rh6G (546 nm) to FL (520 nm). TSCE could not be observed for S101 at 600 nm. From S101, KR emission was observed only at high angles and with P polarization. The absence of TSCE from S101 is consistent with the dispersion calculations, which show that a Tamm state does not exist in in the experimental Tamm structure for wavelengths above 570 nm. It was also found that the angular distribution of the RK emission of the three fluorophores, but not S101, depends on the observation angle and also depends on the fluorophore and emission maximum. This result demonstrates that a significant fraction of the RK emission is the result of coupling to the Tamm state.

The fluorescence emission maxima for Rh6G and FL are in excellent agreement with the resonances found from the reflectivity calculations. It is interesting to note that the same emission maxima are noticed at the same observation angle independent of the fluorophore. For instance, an emission maximum is observed at 570 nm for both Rh6G and FL at 0°. Similarly, the same 600-nm emission maximum is observed for both Rh6G and FL at 30°. This result shows that the dependence of wavelength on angle represents the optical properties of the Tamm structure and not the emission spectra of the fluorophores.

3. Computer Hardware Overview

Figure 15:
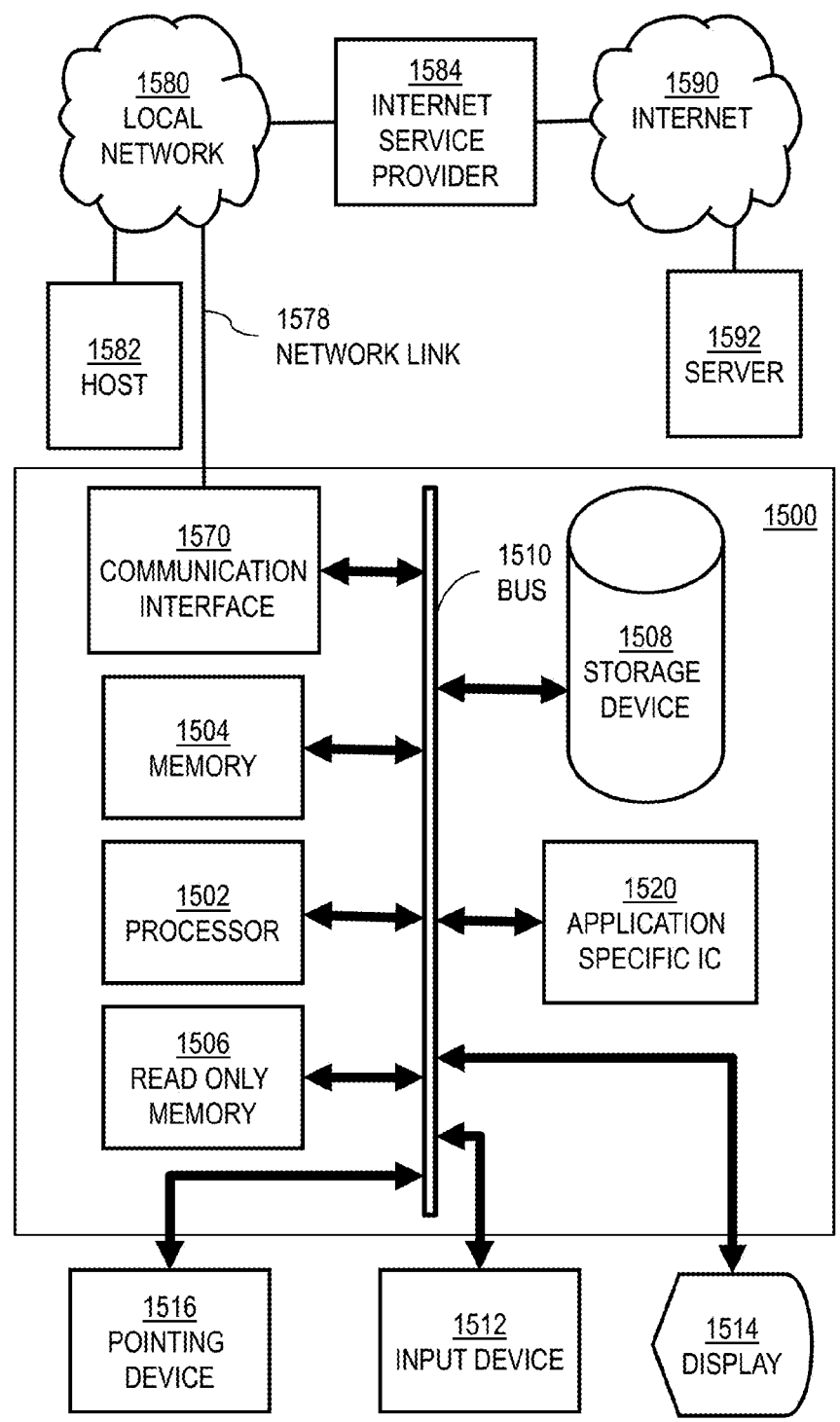
FIG. 15 is a block diagram that illustrates a computer system upon which an embodiment of the invention may be implemented.

FIG. 15 is a block diagram that illustrates a computer system 1500 upon which an embodiment of the invention may be implemented. Computer system 1500 includes a communication mechanism such as a bus 1510 for passing information between other internal and external components of the computer system 1500. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit).). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 1500, or a portion thereof, constitutes a means for performing one or more steps of one or more methods described herein.

A sequence of binary digits constitutes digital data that is used to represent a number or code for a character. A bus 1510 includes many parallel conductors of information so that information is transferred quickly among devices coupled to the bus 1510. One or more processors 1502 for processing information are coupled with the bus 1510. A processor 1502 performs a set of operations on information. The set of operations include bringing information in from the bus 1510 and placing information on the bus 1510. The set of operations also typically include comparing two or more units of information, shifting positions of units of information, and combining two or more units of information, such as by addition or multiplication. A sequence of operations to be executed by the processor 1502 constitutes computer instructions.

Computer system 1500 also includes a memory 1504 coupled to bus 1510. The memory 1504, such as a random access memory (RAM) or other dynamic storage device, stores information including computer instructions. Dynamic memory allows information stored therein to be changed by the computer system 1500. RAM allows a unit of information stored at a location called a memory address to be stored and retrieved independently of information at neighboring addresses. The memory 1504 is also used by the processor 1502 to store temporary values during execution of computer instructions. The computer system 1500 also includes a read only memory (ROM) 1506 or other static storage device coupled to the bus 1510 for storing static information, including instructions, that is not changed by the computer system 1500. Also coupled to bus 1510 is a non-volatile (persistent) storage device 1508, such as a magnetic disk or optical disk, for storing information, including instructions, that persists even when the computer system 1500 is turned off or otherwise loses power.

Information, including instructions, is provided to the bus 1510 for use by the processor from an external input device 1512, such as a keyboard containing alphanumeric keys operated by a human user, or a sensor. A sensor detects conditions in its vicinity and transforms those detections into signals compatible with the signals used to represent information in computer system 1500. Other external devices coupled to bus 1510, used primarily for interacting with humans, include a display device 1514, such as a cathode ray tube (CRT) or a liquid crystal display (LCD), for presenting images, and a pointing device 1516, such as a mouse or a trackball or cursor direction keys, for controlling a position of a small cursor image presented on the display 1514 and issuing commands associated with graphical elements presented on the display 1514.

In the illustrated embodiment, special purpose hardware, such as an application specific integrated circuit (IC) 1520, is coupled to bus 1510. The special purpose hardware is configured to perform operations not performed by processor 1502 quickly enough for special purposes. Examples of application specific ICs include graphics accelerator cards for generating images for display 1514, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 1500 also includes one or more instances of a communications interface 1570 coupled to bus 1510. Communication interface 1570 provides a two-way communication coupling to a variety of external devices that operate with their own processors, such as printers, scanners and external disks. In general the coupling is with a network link 1578 that is connected to a local network 1580 to which a variety of external devices with their own processors are connected. For example, communication interface 1570 may be a parallel port or a serial port or a universal serial bus (USB) port on a personal computer. In some embodiments, communications interface 1570 is an integrated services digital network (ISDN) card or a digital subscriber line (DSL) card or a telephone modem that provides an information communication connection to a corresponding type of telephone line. In some embodiments, a communication interface 1570 is a cable modem that converts signals on bus 1510 into signals for a communication connection over a coaxial cable or into optical signals for a communication connection over a fiber optic cable. As another example, communications interface 1570 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 1570 sends and receives electrical, acoustic or electromagnetic signals, including infrared and optical signals, which carry information streams, such as digital data.

The term computer-readable medium is used herein to refer to any medium that participates in providing information to processor 1502, including instructions for execution. Such a medium may take many forms, including, but not limited to, non-volatile media, volatile media and transmission media. Non-volatile media include, for example, optical or magnetic disks, such as storage device 1508. Volatile media include, for example, dynamic memory 1504. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 1502, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 1502, except for carrier waves and other signals.

Logic encoded in one or more tangible media includes one or both of processor instructions on a computer-readable storage media and special purpose hardware, such as ASIC 1520.

Network link 1578 typically provides information communication through one or more networks to other devices that use or process the information. For example, network link 1578 may provide a connection through local network 1580 to a host computer 1582 or to equipment 1584 operated by an Internet Service Provider (ISP). ISP equipment 1584 in turn provides data communication services through the public, world-wide packet-switching communication network of networks now commonly referred to as the Internet 1590. A computer called a server 1592 connected to the Internet provides a service in response to information received over the Internet. For example, server 1592 provides information representing video data for presentation at display 1514.

The invention is related to the use of computer system 1500 for implementing the techniques described herein. According to one embodiment of the invention, those techniques are performed by computer system 1500 in response to processor 1502 executing one or more sequences of one or more instructions contained in memory 1504. Such instructions, also called software and program code, may be read into memory 1504 from another computer-readable medium such as storage device 1508. Execution of the sequences of instructions contained in memory 1504 causes processor 1502 to perform the method steps described herein. In alternative embodiments, hardware, such as application specific integrated circuit 1520, may be used in place of or in combination with software to implement the invention. Thus, embodiments of the invention are not limited to any specific combination of hardware and software.

The signals transmitted over network link 1578 and other networks through communications interface 1570, carry information to and from computer system 1500. Computer system 1500 can send and receive information, including program code, through the networks 1580, 1590 among others, through network link 1578 and communications interface 1570. In an example using the Internet 1590, a server 1592 transmits program code for a particular application, requested by a message sent from computer 1500, through Internet 1590, ISP equipment 1584, local network 1580 and communications interface 1570. The received code may be executed by processor 1502 as it is received, or may be stored in storage device 1508 or other non-volatile storage for later execution, or both. In this manner, computer system 1500 may obtain application program code in the form of a signal on a carrier wave.

Various forms of computer readable media may be involved in carrying one or more sequence of instructions or data or both to processor 1502 for execution. For example, instructions and data may initially be carried on a magnetic disk of a remote computer such as host 1582. The remote computer loads the instructions and data into its dynamic memory and sends the instructions and data over a telephone line using a modem. A modem local to the computer system 1500 receives the instructions and data on a telephone line and uses an infra-red transmitter to convert the instructions and data to a signal on an infra-red a carrier wave serving as the network link 1578. An infrared detector serving as communications interface 1570 receives the instructions and data carried in the infrared signal and places information representing the instructions and data onto bus 1510. Bus 1510 carries the information to memory 1504 from which processor 1502 retrieves and executes the instructions using some of the data sent with the instructions. The instructions and data received in memory 1504 may optionally be stored on storage device 1508, either before or after execution by the processor 1502.

Figure 16:
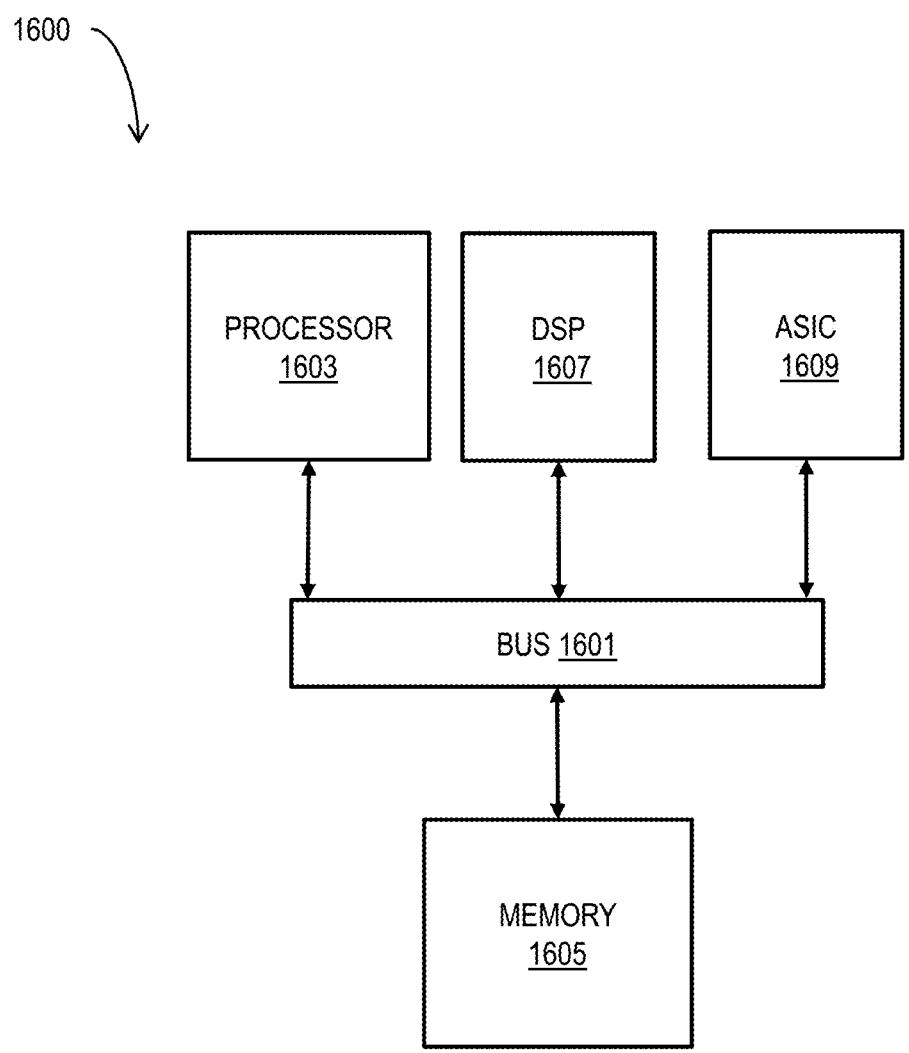
FIG. 16 illustrates a chip set upon which an embodiment of the invention may be implemented.

FIG. 16 illustrates a chip set 1600 upon which an embodiment of the invention may be implemented. Chip set 1600 is programmed to perform one or more steps of a method described herein and includes, for instance, the processor and memory components described with respect to FIG. 15 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 1600, or a portion thereof, constitutes a means for performing one or more steps of a method described herein.

In one embodiment, the chip set 1600 includes a communication mechanism such as a bus 1601 for passing information among the components of the chip set 1600. A processor 1603 has connectivity to the bus 1601 to execute instructions and process information stored in, for example, a memory 1605. The processor 1603 may include one or more processing cores with each core configured to perform independently. A multi-core processor enables multiprocessing within a single physical package. Examples of a multi-core processor include two, four, eight, or greater numbers of processing cores. Alternatively or in addition, the processor 1603 may include one or more microprocessors configured in tandem via the bus 1601 to enable independent execution of instructions, pipelining, and multithreading. The processor 1603 may also be accompanied with one or more specialized components to perform certain processing functions and tasks such as one or more digital signal processors (DSP) 1607, or one or more application-specific integrated circuits (ASIC) 1609. A DSP 1607 typically is configured to process real-world signals (e.g., sound) in real time independently of the processor 1603. Similarly, an ASIC 1609 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 1603 and accompanying components have connectivity to the memory 1605 via the bus 1601. The memory 1605 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 1605 also stores the data associated with or generated by the execution of one or more steps of the methods described herein.

4. Extensions and Modifications

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items. elements or steps. Furthermore, the indefinite article "a" or "an" is meant to indicate one or more of the item, element or step modified by the article.

5. Bibliography

Each of the following citations is hereby incorporated by reference as if fully set forth herein, except as the terminology is inconsistent with the terminology used herein.

[1] J. R. Lakowicz, Radiative decay engineering: biophysical and biomedical applications, Anal. Biochem. 298 (2001) 1-24.

[2] J. R. Lakowicz, Plasmonics in biology and plasmon-controlled fluorescence, Plasmonics 1 (2006) 5-33.

[3] J. R. Lakowicz, Radiative decay engineering 5: metal-enhanced fluorescence and plasmon emission, Anal. Biochem. 337 (2005) 171-194.

[4] A. P. Demchenko, Nanoparticles and nanocomposites for fluorescence sensing and imaging, Methods Appl. Fluoresc. 1 (2013) 022001.

[5] J. R. Lakowicz, Y. Shen, S. D'Auria, J. Malicka, J. Fang, Z. Gryczynski, I. Gryczynski, Radiative decay engineering 2: effects of silver island films on fluorescence intensity, lifetimes, and resonance energy transfer, Anal. Biochem. 301 (2002) 261-277.

[6] J. R. Lakowicz, Radiative decay engineering 3: surface plasmon-coupled directional emission, Anal. Biochem. 324 (2004) 153-169.

[7] I. Gryczynski, J. Malicka, Z. Gryczynski, J. R. Lakowicz, Radiative decay engineering 4: experimental studies of surface plasmon-coupled directional emission, Anal. Biochem. 324 (2004) 170-182.

[8] E. Fort, S. Gressillon, Surface enhanced fluorescence, J. Phys. D 41 (2008) 1-31.

[9] F. Xie, K. Drozdowicz-Tomisa, E. M. Goldys, A method to assess modifications of fluorophore radiative rate by plasmonic structures, Chem. Phys. Lett. 466 (2008) 186-188.

[10] E. J. A. Kroekenstoel, E. Verhagen, R. J. Walters, L. Kuipers, A. Polman, Enhanced spontaneous emission rate in annular plasmonic nanocavities, Appl. Phys. Lett. 95 (2009) 263106.

[11] Y. Fu, J. R. Lakowicz, Modification of single molecule fluorescence near metallic nanostructures, Laser Photonics Rev. 3 (2009) 221-233.

[12] J. Zhang, Y. Fu, M. H. Chowdhury, J. R. Lakowicz, Single-molecule studies on fluorescently labeled silver particles: effects of particle size, J. Phys. Chem. C 112 (2008) 18-26.

[13] P. Anger, P. Bharadwaj, L. Novotny, Enhancement and quenching of singlemolecule fluorescence, Phys. Rev. Lett. 96 (2006) 113002.

[14] A. Kinkhabwala, Z. Yu, S. Fan, Y. Avlasevich, K. Mullen, W. E. Moerner, Large single-molecule fluorescence enhancements produced by a bowtie nanoantenna, Nat. Photonics 3 (2009) 654-657.

[15] F. Tam, G. P. Goodrich, B. R. Johnson, N. J. Halas, Plasmonic enhancement of molecular fluorescence, Nano Lett. 7 (2007) 496-501.

[16] Y. Chen, K. Munechika, D. S. Giner, Dependence of fluorescence intensity on the spectral overlap between fluorophores and plasmon resonant single silver nanoparticles, Nano Lett. 7 (2007) 690-696.

[17] N. Akbay, J. R. Lakowicz, K. Ray, Distance-dependent metal-enhanced intrinsic fluorescence of proteins using polyelectrolyte layer-by-layer assembly and aluminum nanoparticles, J. Phys. Chem. C 116 (2012) 10766-10773.

[18] Y.-H. Chang, Y.-C. Lu, K.-S. Chou, Enhancement of photoluminescence of different quantum dots by Ag@SiO2 core-shell nanoparticles, Mater. Res. Bull. 8 (2013) 2076-2078.

[19] W. Li, J. Zhang, Y. Zhou, P. Zhang, Highly enhanced fluorescence of fluorophores inside a metallic nanocavity, Chem. Commun. 47 (2011) 5834-5836.

[20] J. Zhang, Y. Fu, X. Xu, J. R. Lakowicz, Target molecule imaging on tissue specimens by fluorescent metal nanoprobes, J. Biomed. Optics 16 (2011) 116004.

[21] J. Zhang, Y. Fu, F. Mandavi, Bimetallic nanoshells for metal-enhanced fluorescence with broad band fluorophores, J. Phys. Chem. C 116 (2012) 24224-24232.

[22] J. Zhang, I. Gryczynski, Z. Grycynski, J. R. Lakowicz, Dye-labeled silver nanoshell-bright particle, J. Phys. Chem. B 110 (2006) 8986-8991.

[23] Y. Fu, J. Zhang, J. R. Lakowicz, Large enhancement of single molecule fluorescence by coupling to hollow silver nanoshells, Chem. Commun. 48 (2012) 9726-9728.

[24] S. J. Norton, T. Vo-Dinh, Plasmonics quenching, and enhancement of a fluorescing molecule outside and inside a silver metallic nanoshell, IEEE Trans. Nanotechnol. 10 (2011) 1264-1284.

[25] Y. C. Jun, K. C. Y. Huang, M. L. Brongersma, Plasmonic beaming and active control over fluorescent emission, Nat. Commun. 2 (2011) 283-289.

[26] H. Aouani, O. Mahboub, N. Bonod, E. Devaus, E. Popov, H. Rigneault, T. W. Ebbesen, J. Wenger, Bright unidirectional fluorescence emission of molecules in a nanoaperture with plasmonic corrugations, Nano Lett. 11 (2011) 637-644.

[27] N. S. King, Y. Li, C. Ayala-Orozco, T. Brannan, P. Nordlander, N. J. Halas, Angle- and spectral-dependent light scattering from plasmonic nanocups, ACS Nano 9 (2011) 7254-7262.

[28] G. Sun, J. B. Khurgin, C. C. Yang, Impact of high-order surface plasmon modes of metal nanoparticles on enhancement of optical emission, Appl. Phys. Lett. 956 (2009) 171103.

[29] H. Mertens, A. F. Koenderink, A. Polman, Plasmon-enhanced luminescence near noble-metal nanospheres: comparison of exact theory and an improved Gersten and Nitzan model, Phys. Rev. B 76 (2007) 115123.

[30] G. Sun, J. B. Khurgin, R. A. Soref, Practical enhancement of photoluminescence by metal nanoparticles, Appl. Phys. Lett. 94 (2009) 101103.

[31] Y. C. Jun, R. D. Kekatpure, J. S. White, M. L. Brongersma, Nanoresonant enhancement of spontaneous emission in metal-dielectric metal plasmon waveguide structures, Phys. Rev. B 78 (2008) 153111.

[32] S. D'Agostino, F. D. Sala, L. C. Andreani, Dipole-excited surface plasmons in metallic nanoparticles: Engineering decay dynamics within the discretedipole approximation, Phys. Rev. B 87 (2013) 205413.

[33] F. Xie, K. Drozdowicz-Tomsia, E. M. Goldys, A method to assess modifications of fluorophore radiative rate by plasmonic structures, Chem. Phys. Lett. 466 (2008) 186-188.

[34] M. H. Chowdhury, J. Pond, S. K. Gray, J. R. Lakowicz, Systematic computational study of the effect of silver nanoparticle dimers on the coupled emission from nearby fluorophores, J. Phys. Chem. C 112 (2008) 11236-11249.

[35] H. Nabika, M. Takase, F. Nagasawa, K. Murakoshi, Toward plasmon-induced photoexcitation of molecules, J. Phys. Chem. Lett. 1 (2010) 2470-2487.

[36] J. A. Dionne, H. A. Atwater, Plasmonics: metal-worthy methods and materials in nanophotonics, MRS Bull. 37 (2012) 717-724.

[37] J. A. Schuller, E. S. Barnard, W. Cai, Y. C. Jun, J. S. White, M. L. Brongersma, Plasmonics for extreme light concentration and manipulation, Nat. Mater. 9 (2010) 193-204.

[38] P. K. Jain, M. A. El-Sayed, Plasmonic coupling in noble metal nanostructures, Chem. Phys. Lett. 487 (2010) 153-164.

[39] M. I. Stockman, Nanoplasmonics: past, present, and glimpse into future, Opt. Express 19 (2011) 22029-22106.

[40] B. E. A. Saleh, M. C. Teich, Fundamentals of Photonics, 2nd ed., Wiley-Interscience, New York, 2007.

[41] J. D. Joannopoulos, S. G. Johnson, J. N. Winn, R. D. Meade, Photonic Crystals: Molding the Flow of Light, 2nd ed., Princeton University Press, Princeton, N.J., 2008.

[42] H. Wang, K.-Q. Zhang, Photonic crystal structures with tunable structure color as colorimetric sensors, Sensors 13 (2013) 4192-4213.

[43] P. Kurt, D. Banerjee, R. E. Cohen, M. F. Rubner, Structural color via layer-by-layer deposition: layered nanoparticle arrays with near-UV and visible reflectivity bands, J. Mater. Chem. 19 (2009) 8920-8927.

[44] E. Yablonovitch, Inhibited spontaneous emission in solid-state physics and electronics, Phys. Rev. Lett. 58 (1987) 2059-2062.

[45] S. John, Strong localization of photons in certain disordered dielectric superlattices, Phys. Rev. Lett. 58 (1987) 2486-2489.

[46] R. Kashyap, Fiber Bragg Gratings, 2nd ed., Optics and Photonics Series, Academic Press, San Diego, 2009.

[47] I. S. Nikolaev, P. Lodahl, W. L. Vos, Fluorescence lifetime of emitters with broad homogeneous line-widths modified in optical photonic crystals, J. Phys. Chem. C 112 (2008) 7250-7254.

[48] S. Kubo, A. Fujishima, 0. Sato, H. Segawa, Anisotropic accelerated emission of the chromophores in photonic crystals consisting of a polystyrene opal structure, J. Phys. Chem. C 113 (2009) 11704-11711.

[49] R. Badugu, K. Nowaczyk, E. Descrovi, J. R. Lakowicz, Radiative decay engineering 6: fluorescence on one-dimensional photonic crystals, Anal. Biochem. 49 (2013) 83-96.

[50] M. Ballarini, F. Frascella, F. Michelotti, G. Digregorio, P. Rivolo, V. Paeder, V. Musi, F. Giorgis, E. Descrovi, Bloch surface waves-controlled emission of organic dyes grafted on a one-dimensional photonic crystals, Appl. Phys. Lett. 99 (2011) 043302.

[51] J. Homola (Ed.), Surface Plasmon Resonance Based Sensors, Springer, New York, 2006.

[52] M. L. Brongersma, P. G. Kik (Eds.), Surface Plasmon Nanophotonics, Springer, New York, 2007.

[53] I. Tamm, A possible binding of the electrons on a crystal surface, Zh. Eksp Teor. Fiz. 3 (1933) 34-35.

[54] M. Born, E. Wolf, Principles of Optics, Cambridge University Press, Cambridge, UK, 2002.

[55] N. W. Ashcroft, N. David Mermin, Solid State Physics, Brooks/Cole, Belmont, Calif., 1976.

[56] A. V. Kavokin, I. A. Shelykh, G. Malpuech, Lossless interface modes at the boundary between two periodic dielectric structures, Phys. Rev. B 72 (2005) 233102.

[57] M. Kaliteevski, I. Iorsh, S. Brand, R. A. Abram, J. M. Chamberlain, A. V. Kavokin, I. A. Shelykh, Tamm plasmon-polaritons: possible electromagnetic states at the interface of a metal and a dielectric Bragg mirror, Phys. Rev. B 76 (2007) 165415.

[58] J. A. Gaspar-Armenta, F. Villa, Photonic surface-wave excitation: photonic crystal-metal interface, J. Opt. Soc. Am. B 20 (2003) 2349-2354.

[59] Z. Chem, P. Han, C. W. Leung, Y. Wang, M. Hu, Y. Chen, Study of optical Tamm states based on the phase properties of one-dimensional photonic crystals, Opt. Express 20 (2012) 21618-21626.

[60] A. Kavokin, I. Shelykh, G. Malpuech, Optical Tamm states for the fabrication of polariton lasers, Appl. Phys. Lett. 87 (2005) 261005.

[61] M. E. Sasin, R. P. Seisyan, M. A. Kalitteevski, S. Brand, R. A. Abram, J. M. Chamberlain, A. Y. Egorov, A. P. Vasil'ev, V. S. Mikhrin, A. V. Kavokin, Tamm plasmon polaritons: slow and spatially compact light, Appl. Phys. Lett. 92 (2008) 251112.

[62] S. M. Vukovic, Plasmonic Bragg reflector and Tamm plasmon polaritons in metal-dielectric superlattices, Acta Phys. Pol., A 116 (2009) 678-680.

[63] Y.-T. Fang, L.-K. Chen, N. Zhu, J. Zhou, Tamm states of one-dimensional metal-dielectric photonic crystal, IET Optoelectron. 7 (2013) 9-13.

[64] L. Thevenaz, I. Dicaire, S.-H. Chin, Enhancing the light-matter interaction using slow light: towards the concept of dense light, Proc. SPIE 8273 (2012). 8273-1D.

[65] M. E. V. Pedersen, L. S. Rishej, H. Steffensen, S. Xiao, N. A. Mortensen, Slow-light enhanced optical detection in liquid-infiltrated photonic crystals, Opt. Quant. Electron. 39 (2007) 903-911.

[66] P. B. Johnson, R. W. Christy, Optical constants of the noble metals, Phys. Rev. B 6 (1972) 4370-4374.

[67] H. A. Macleod, Thin-Film Optical Filters, Institute of Physics, Philadelphia, 2001.

[68] A. A. R. Elshabini-Riad, F. D. Barlow, Thin Film Technology Handbook, McGraw-Hill, New York, 1997.

[69] O. S. Heavens, Optical Properties of Thin Solid States, Dover, New York, 1955.

[70] I. Gryczynski, J. Malicka, K. Nowaczyk, Z. Gryczynski, J. R. Lakowicz, Effects of sample thickness on the optical properties of surface plasmon-coupled emission, J. Phys. Chem. B 108 (2004) 12073-12083.

[71] A. A. Maradudin (Ed.), Structured Surfaces as Optical Metamaterials, Cambridge University Press, Cambridge, UK, 2011.

[72] M. L. Brongersma, P. G. Kik (Eds.), Surface Plasmon Nanophotonics, Springer, New York, 2008.

[73] S. Brand, M. A. Kaliteevski, R. A. Abram, Optical Tamm states above the bulk plasma frequency at a Bragg stack/metal interface, Phys. Rev. B 79 (2009) 085416.

[74] G. Du, L. Cui, L. Zhang, H. Jiang, Tamm plasmon polaritons in composite structures composed of the metal film and truncated photonic crystals, Appl. Phys. A 109 (2012) 907-911.

[75] S. Feng, J. M. Elson, P. L. Overfelt, Transparent photonic band in metallo-dielectric nanostructures, Phys. Rev. B 72 (2005) 085117.

[76] Y. He, H. Zhou, Y. Jin, S. He, Plasmon induced transparency in a dielectric waveguide, Appl. Phys. Lett. 99 (2011) 043113.

[77] M. Sclaora, M. J. Bioemer, A. S. Pethel, J. P. Dowling, C. M. Bowden, A. S. Manka, Transparent metallo-dielectric one-dimensional, photonic band-gap structures, J. Appl Plys. 83 (1988) 2377-2383.

[78] S. H. Tsang, S. F. Yu, X. F. Li, H. Y. Yang, H. K. Liang, Observation of Tamm plasmon polaritons in visible regime from ZnO/Al2O3 distributed Bragg reflector-Ag interface, Opt. Commun. 284 (2011) 1890-1892.

[79] E. Battal, A. K. Okyay, Metal-dielectric-metal plasmonic resonators for active beam steering in the infrared, Opt. Lett. 38 (2013) 983-985.

[80] I. Iorsh, A. Poddubny, A. Orlov, P. Belov, Y. S. Kivshar, Spontaneous emission enhancement in metal-dielectric metamaterials, Phys. Lett. A 376 (2012) 183-187.

[81] M. S. Jang, H. Atwater, Plasmonic rainbow trapping structures for light localization and spectrum splitting, Phys. Rev. Lett. 107 (2011) 207401.

[82] L. Zhou, C. Huang, S. Wu, X. Yin, Y. Wang, Q. Wang, Y. Zhu, Enhanced optical transmission through metal-dielectric multilayer gratings, Appl. Phys. Lett. 97 (2010) 011905.

[83] M. Tian, P. Lu, L. Chen, D. Liu, N. Peyghambarian, Plasmonic Bragg reflectors based on metal-embedded MIM structure, Opt. Commun. 285 (2012) 5122-5127.

[84] S. D. Choudhury, R. Badugu, K. Nowaczyk, K. Ray, J. R. Lakowicz, Tuning fluorescence direction with plasmonic metal-dielectric-metal substrates, J. Phys. Chem. Lett. 4 (2013) 227-232.

[85] S.D. Choudhury, R. Badugu, K. Ray, J. R. Lakowicz, Steering fluorescence emission with metal-dielectric-metal structures of Au, Ag, and Al, J. Phys. Chem. C 117 (2013) 15798-15807.

[86] J. Erlebacher, M. J. Aziz, A. Karma, N. Dimitrov, K. Sieradzki, Evolution of nanoporosity in dealloying, Nature 410 (2001) 450-456.

[87] Z. Zhang, Y. Wang, Z. Qi, W. Zhang, J. Qin, J. Frenzel, Generalized fabrication of nanoporous metals (Au, Pd, Pt, Ag, and Cu) through chemical dealloying, J. Phys. Chem. C 113 (2009) 12629-12636.

[88] Y. Ding, J. Erlebacher, Nanoporous metals with controlled multimodal pore size distribution, J. Am. Chem. Soc. 125 (2003) 7772-7773.

[89] F. Yu, S. Ahl, A.-M. Caminade, J.-P. Majoral, W. Knoll, J. Erlebacher, Simultaneous excitation of propagating and localized surface plasmon resonance in nanoporous gold membranes, Anal. Chem. 78 (2006) 7346-7350.

[90] I. Abdulhalim, A. Lakhtakia, A. Lahav, F. Zhang, J. Xu, Porosity effect on surface plasmon resonance from metallic sculptured thin films, Proc. SPIE 7041 (2008). 7041-11.

[91] A. Shalabney, A. Lakhtakia, I. Abdulhalim, A. Lahav, C. Patzig, I. Hazek, A. Karabchevsky, B. Rauschenbach, F. Zhang, J. Xu, Surface plasmon resonance from metallic columnar thin films, Photonics Nanostruct. 7 (2009) 176-185.

[92] H. Zhou, G. Yang, K. Wang, H. Long, P. Lu, Multiple optical Tamm states at a metal-dielectric minor interface, Opt. Lett. 35 (2010) 4112-4114.
[93] J. Wenger, D. Gerard, H. Aouani, H. Rigneault, Nano-aperture-enhanced signal-to-noise ratio in fluorescence correlation spectroscopy, Anal. Chem. 81 (2009) 834-839.
[94] C. Genet, T. W. Ebbesen, Light in tiny holes, Nature 445 (2007) 39-46.
[95] J. Eid, A. Fehr, J. Gray, K. Luong, J. Lyle, G. Otto, P. Peluso, D. Rank, P. Baybayan, B. Bettman, et al., Real-time DNA sequencing from single polymerase molecules, Science 323 (2009) 133-138.
[96] M. L. Metzker, Sequencing technologies—the next generation, Nat. Rev. 11 (2010) 32-46.
[97] R. Badugu, K. Nowaczyk, E. Descrovi, J. R. Lakowicz, Radiative decay engineering 6: Fluorescence on one-dimensional photonic crystals, Anal. Biochem. 442 (2013) 83-96.
[98] R. Badugu, E. Descrovi, J. R. Lakowicz, Radiative decay engineering 7: Tamm state-coupled emission using a hybrid plasmonic-photonic structure, Anal. Biochem. 445 (2014) 1-13.

What is claimed is:

1. A substrate for a target optical frequency comprising a metal nanoscale layer deposited on a Bragg grating, wherein:
    the Bragg grating comprises a plurality of dielectric layers including a plurality of high index of refraction layers alternating with a plurality of low index of refraction layers;
    the plurality of dielectric layers are parallel to the metal nanoscale layer;
    the thickness of each layer of the plurality of dielectric layers is about a fourth of a wavelength of the target optical frequency in the layer; and
    the metal nanoscale layer includes a nanoporous metal film to host a fluorophore and is functionalized with a bioactive target molecule that has an affinity for a particular analyte to form a functionalized substrate.

2. A substrate as recited in claim 1, wherein the nanoporous metal film has a pore size large enough to accommodate a molecular complex that includes the fluorophore.

3. A substrate as recited in claim 1, wherein the metal nanoscale layer comprises a plurality of nanoscale holes that expose an adjacent dielectric layer of the plurality of dielectric layers.

4. A substrate as recited in claim 3, wherein each of the plurality of nanoscale holes is large enough to accommodate a molecular complex that includes the fluorophore.

5. A substrate as recited in claim 3, wherein the adjacent dielectric layer comprises a plurality of nanoscale holes that align with at least some of the plurality of nanoscale holes in the metal nanoscale layer.

6. A substrate as recited in claim 1, wherein a first dielectric layer of the plurality of dielectric layers adjacent to the metal nanoscale layer is a high index of refraction layer of the plurality of high index of refraction layers.

7. A substrate as recited in claim 1, wherein for emissions from the fluorophore hosted by the metal nanoscale layer and excited by incident light, there is an emission intensity maximum centered at a non-zero angle independent of the direction of the incident light for a different optical frequency than the target optical frequency.

8. A substrate as recited in claim 7, wherein the emission intensity maximum at the different optical frequency is centered at a non-zero angle less than 30 degrees.

9. A substrate as recited in claim 1, wherein the fluorophore is complexed with the bioactive target molecule during a detection or assay of the particular analyte.

10. A fluorescence affinity assay kit for determining the quantity of a particular analyte, comprising:
    the substrate as recited in claim 1; and
    a reagent comprising at least one plurality of identical detection molecules, wherein the detection molecule comprises the fluorophore, and the detection molecule has affinity for the particular analyte.

11. A fluorescence affinity assay kit as recited in claim 10, wherein for emissions from the fluorophore when hosted by the metal nanoscale layer and excited by incident light, there is an emission intensity maximum centered at a non-zero angle independent of the direction of the incident light for a different optical frequency than the target optical frequency.

12. A fluorescence affinity assay kit as recited in claim 10, wherein the reagent further comprises a different detection molecule for a different analyte, wherein the detection molecule includes a different fluorophore that fluoresces at a different optical frequency from the target optical frequency and the substrate produces an emission intensity maximum centered at a non-zero angle independent of the direction of the incident light for the different optical frequency.

13. A system comprising:
    a source of incident light;
    the substrate as recited in claim 1, to be placed in contact with a mixture of a sample and a reagent, wherein the reagent comprises a detection molecule for the particular analyte wherein the detection molecule includes a fluorophore that fluoresces near the target optical frequency to produce a S polarized emission that propagates out of the substrate;
    an optical coupler to direct incident light onto the substrate; and
    a detector to measure fluorescent emissions from the substrate.

14. A system as recited in claim 13, wherein the detector comprises a photo array to record an image of the fluorescent emissions from the substrate.

15. A system as recited in claim 13, wherein:
    the substrate produces an emission intensity maximum centered at a different non-zero angle independent of the direction of the incident light for each different optical frequency from the target optical frequency; and
    the detector detects fluorescent emissions at a plurality of different angles from the substrate.

16. A system as recited in claim 13, further comprising a polarizer disposed in an optical path between the substrate and the detector, wherein the polarizer passes only S polarized light.

17. A system as recited in claim 13, further comprising:
    at least one processor; and
    at least one memory including one or more sequences of instructions,
    the at least one memory and the one or more sequences of instructions cause the apparatus to perform at least the following,
    determining a calibration curve that relates concentration of the particular analyte to at least one of intensity or direction or polarization of fluorescent emissions at the functionalized substrate in response to the incident light for a plurality of known concentrations of the particular analyte mixed with the reagent; and determining a concentration of the particular analyte in a sample directly from the calibration curve and measurements of at least one of intensity or direction or polarization of fluorescent emissions at the functionalized substrate in contact with the sample and reagent in response to the incident light.

18. A method for determining the presence or quantity of a particular analyte, comprising:
providing a functionalized substrate for a target optical frequency comprising the substrate of claim 1;
providing a reagent comprising a detection molecule for the particular analyte, wherein the detection molecule includes a fluorophore that fluoresces at the target optical frequency;
determining a calibration curve that relates detection or quantity of the particular analyte to at least one of intensity or direction or polarization of fluorescent emissions at the functionalized substrate in response to incident light based on intensity or direction or polarization of fluorescent emissions at the functionalized substrate in response to incident light for a plurality of known concentrations of the particular analyte mixed with the reagent,
contacting a sample and the reagent to the functionalized substrate;
obtaining measurements of at least one of intensity or direction or polarization of fluorescent emissions at the functionalized substrate in contact with the sample and reagent in response to the incident light; and
determining a presence or quantity of the particular analyte in the sample from the calibration curve and the measurements.

19. A method as recited in claim 18, the reagent further comprising a different detection molecule for a different analyte, wherein the different detection molecule includes a different fluorophore that fluoresces at a different optical frequency from the target optical frequency and the substrate produces an emission intensity maximum centered at a non-zero angle independent of the direction of the incident light for the different optical frequency.

20. A method as recited in claim 18, wherein obtaining measurements further comprises directing the incident light to impinge on the sample without passing through the substrate.

21. A method as recited in claim 18, wherein obtaining measurements further comprises directing the incident light normal to the plurality of dielectric layers in the substrate.

22. A method as recited in claim 18, wherein obtaining measurements further comprises directing the incident light to impinge on the sample after passing through the substrate.

23. A method as recited in claim 18, further comprising determining an angle of an emission intensity maximum independent of a direction of the incident light.

24. A method as recited in claim 23, wherein obtaining measurements further comprises collecting fluorescent emissions in a collection cone that includes the angle of the emission intensity maximum.

25. A method as recited in claim 23, wherein the angle of an emission intensity maximum is associated with a Tamm Structure coupled emission (TSCE).

26. A method as recited in claim 18, wherein a distance from the fluorophore to the substrate, when the detection molecule is bound to the bioactive target molecule, is less than a wavelength of the target optical frequency in the sample.

* * * * *